(12) United States Patent
Zeng

(10) Patent No.: US 7,886,577 B2
(45) Date of Patent: Feb. 15, 2011

(54) DEVICES WITH SURFACE BOUND IONIC LIQUIDS AND METHOD OF USE THEREOF

(75) Inventor: Xiangqun Zeng, Rochester, MI (US)

(73) Assignee: Oakland University, Rochester, MI (US)

( * ) Notice: Subject to any disclaimer, the term of this patent is extended or adjusted under 35 U.S.C. 154(b) by 573 days.

(21) Appl. No.: 11/725,637

(22) Filed: Mar. 20, 2007

(65) Prior Publication Data

US 2007/0231918 A1  Oct. 4, 2007

Related U.S. Application Data

(60) Provisional application No. 60/787,594, filed on Mar. 30, 2006.

(51) Int. Cl.
*G01N 29/02* (2006.01)
(52) U.S. Cl. ..................................... 73/24.06; 73/24.01
(58) Field of Classification Search .................. 436/141; 73/24.01, 24.06
See application file for complete search history.

(56) References Cited

U.S. PATENT DOCUMENTS

| | | | |
|---|---|---|---|
| 3,327,519 A * | 6/1967 | Crawford | ................... 73/24.06 |
| 4,236,893 A | 12/1980 | Rice | |
| 4,242,096 A | 12/1980 | Oliveira et al. | |
| 4,246,344 A | 1/1981 | Silver, III | |
| 4,314,821 A | 2/1982 | Rice | |
| 4,735,906 A | 4/1988 | Bastiaans | |
| 4,788,466 A | 11/1988 | Paul et al. | |
| 4,999,284 A | 3/1991 | Ward et al. | |
| 5,117,192 A | 5/1992 | Hurd | |
| 5,201,215 A | 4/1993 | Granstaff et al. | |
| 5,233,261 A | 8/1993 | Wajid | |
| 5,282,925 A | 2/1994 | Jeng et al. | |
| 5,314,830 A | 5/1994 | Anderson et al. | |
| 5,484,626 A | 1/1996 | Storjohann et al. | |
| 5,616,827 A | 4/1997 | Simmermon et al. | |
| 5,622,826 A | 4/1997 | Varma | |

(Continued)

FOREIGN PATENT DOCUMENTS

WO   WO 02079212   * 10/2002

(Continued)

OTHER PUBLICATIONS

Y. Shen, Y. Zhang, Q. Zhang, L. Niu, T. You, and A. Ivaska. "Immobilization of ionic liquid with polyelectrolyte as carrier." Chem. Commun. Jul. 20, 2005: 4193-4195.*

(Continued)

*Primary Examiner*—Lisa M Caputo
*Assistant Examiner*—Punam Roy
(74) *Attorney, Agent, or Firm*—Ian C. McLeod; Steven M. Parks

(57) ABSTRACT

An ionic liquid bound on an exposed surface of a device such as for detecting organic chemicals, preferably a gas sensor is described. The gas sensor can operate at high temperatures with a fast linear response which is also reversible. At high temperatures, the frequency change ($\Delta f$) versus concentration (C) curve mirrors the Henry's gas law, such that the concentration of a gas sample in liquid solvent is proportional to the concentration or partial pressure of the sample in gas phase. A single gas sensor, or an array of sensors, can be used for the detection and quantitative analysis of gas vapors.

23 Claims, 32 Drawing Sheets

U.S. PATENT DOCUMENTS

| | | | |
|---|---|---|---|
| 5,706,840 | A | 1/1998 | Schneider |
| 5,795,993 | A | 8/1998 | Pfeifer et al. |
| 5,885,402 | A | 3/1999 | Esquibel |
| 5,932,953 | A | 8/1999 | Drees et al. |
| 6,087,187 | A | 7/2000 | Wiegand |
| 6,106,149 | A | 8/2000 | Smith |
| 6,190,035 | B1 | 2/2001 | Smith |
| 6,319,674 | B1 | 11/2001 | Fulcrand et al. |
| 6,368,877 | B1 | 4/2002 | Zhang et al. |
| 6,439,765 | B2 | 8/2002 | Smith |
| 6,475,808 | B1 | 11/2002 | Wagner et al. |
| 6,475,809 | B1 | 11/2002 | Wagner et al. |
| 6,492,601 | B1 | 12/2002 | Cain et al. |
| 6,579,343 | B2 * | 6/2003 | Brennecke et al. ............. 95/51 |
| 6,647,764 | B1 | 11/2003 | Paul et al. |
| 6,706,977 | B2 | 3/2004 | Cain et al. |
| 6,848,299 | B2 | 2/2005 | Paul et al. |
| 6,852,229 | B2 | 2/2005 | Mehnert et al. |
| 6,890,486 | B2 | 5/2005 | Penelle |
| 7,464,580 | B2 * | 12/2008 | Zeng et al. ................. 73/24.01 |
| 2002/0094531 | A1 | 7/2002 | Zenhausern |
| 2002/0142477 | A1 | 10/2002 | Lewis et al. |
| 2003/0049204 | A1 | 3/2003 | Leyland-Jones |
| 2003/0053950 | A1 | 3/2003 | Leyland-Jones |
| 2003/0068273 | A1 | 4/2003 | Leyland-Jones |
| 2003/0072710 | A1 | 4/2003 | Leyland-Jones |
| 2003/0073133 | A1 | 4/2003 | Leyland-Jones |
| 2003/0077222 | A1 | 4/2003 | Leyland-Jones |
| 2003/0204041 | A1 | 10/2003 | Laas et al. |
| 2004/0054231 | A1 | 3/2004 | Abbott et al. |
| 2004/0262578 | A1 | 12/2004 | Wasserscheid et al. |
| 2005/0005840 | A1 | 1/2005 | Bonrath et al. |
| 2005/0252273 | A1 * | 11/2005 | Imoto ........................ 73/23.2 |

FOREIGN PATENT DOCUMENTS

| | | | |
|---|---|---|---|
| WO | WO 02094883 | * | 11/2002 |
| WO | WO 03051894 | * | 6/2003 |

OTHER PUBLICATIONS

L. Yu, D. Garcia, and X. Zeng. "Ionic liquid high temperature gas sensors." Chem. Commun. Mar. 10 2005: 2277-2279.*
I. Goubaidouline, G. Vidrich, and D. Johannsmann. "Organic vapor sensing with ionic liquids entrapped in alumina nanopores on quartz crystal resonators." Anal. Chem. vol. 77, No. 2 Jan. 15, 2005: 615-619.*
Decastro, C., et al., J. Catalysis, 196, 86-94 (2000).
Chum, H.L., et al., J. Am. Chem. Soc., 97, 3264 (1975).
Zhao, D.B., et al., Catalysis Today, 74, 157-189 (2002).
Olivier-Bourbigou, H., et al., J. Molecular Catalysis A: Chemical, 182-183, 419-437 (2002).
Bradaric, C.J., et al., in Industrial Preparation of Phosphonium Ionic Liquids, ACS Symposium Series 856; Roger, R.D., et al., Edt. American Chemical Society (2003).
Seddon, K.R., in Ionic Liquids for Clean Technology, J. Chem. Tech. Biotech, 68, 315-316 (1997).
Welton, T, in Room-Temperature Ionic Liquids: Solvents for synthesis and Catalysis, Chem. Rev., 99, 2071-2083(1999).
Visser, A.E., et al., in Task-specific ionic liquids for the extraction of metal ions from aqueous solutions, Chem. Comm. 135 (2001).
Bates, E.D., et al., J. Am. Chem. Soc. 124, 926 (2002).
Baker, G.A., in An Analytical view of ionic liquids, The Analyst, 130, 800-808 (2005).
Handy, S.T., Chem. Eur. J., 9, 2938-2944 (2003).
Ding, J., et al., Chem. Mater., 15, 2392-2398 (2003).
Jensen, M.P., et al., J. Am. Chem. Soc. 125, 15466-15473 (2003).
Yang, C., et al., J. phys. Chem. B, 107, 12981-12988 (2003).
Barisci, J.N., et al., Electrochem. Commun. 6, 22-27 (2004).
Wang, P., et al., J. Phys. Chem. B, 107, 13280-13285 (2003).
Liu, W.M., et al., Tribology Letters, 13, 81-85 (2002).
Wang, H.Z., et al., Wear, 256, 44-48 (2004).
Ye, C.F., et al., Wear, 253, 579-584 (2002).
Tsang et al., J. Phys. Chem. B, 2001, 105, 5737-5742.
Kaltenpoth et al., Anal. Chem., 2003, 75, 4756-4765.
Dutta et al., J. Phys. Chem. B, 1999, 103, 4412-4422.
Zhu et al., Anal. Chem., 2002, 74, 120-124.
Simon et al. J. Comb. Chem., 2002, 4, 511-515.
Hu et al., J. Phys. Chem. B, 2004, 108, 11214-11218.
Wang et al., J. Am. Chem. Soc., 2003, 125, 16176-16177.
Dutta et al., Chem. Mater., 2004, 16, 5198-5204.
Grate et al., Anal. Chem., 1993, 65, 987A.
Jarrett and Finklea, Anal. Chem., 1999, 71, 353.
Shinar et al., Anal. Chem., 2000, 72, 5981.
Zellers et al., Anal. Chem., 1995, 67, 1092.
Patrash and Zellers, Anal. Chem., 1993, 65, 2055.
Yang et al., Nature Materials 1: 253-257 (2002).
Bonhote, P., et al., Inorg. Chem., 35, 1168 (1996).
Hsieh, M., et al., Anal. Chem., 76, 1885-1895 (2004).
Chemical Communication, 2005, 2277-2279.
Zhang, Z., et al., in EPD Congress (2002).
Liang, C., et al., Anal. Chem. 74, 2172-2176 (2002).
Nuzzo, R.G., et al., in Adsorption of bifunctional organic disulfides on gold surfaces, J. Am. Chem. Soc., 105, 4481-4483 (1983).
Nuzzo, R.G., et al., J. Am. Chem. Soc., 109, 2358-2368 (1987).
Aslanoglu, M., et al., Analyst, 123, 753-757 (1998).
Grate, J.W., et al., Faraday Discuss. 107, 259-283 (1997).
Grate, J.W., et al., Anal. Chem. 70, 199-203 (1998).
McQuade, D.T., et al., Chem. Rev., 100, 2537-2574 (2000).
Tatumi, R., et al., Chem. Commun., 83-85 (2005).
Yoshizawa, M., et al., Chem. Commun., 1828-1829 (2004).
Ohno, H., et al., Electrochimica Acta, 48, 2079-2083 (2003).
D.S. Silvester, A.J. Wain, L. Aldous, C. Hardacre, R.G. Compton, Electrochemical reduction of nitrobenzene and 4-nitrophenol in the room temperature ionic liquid [C(4)dmim][N(Tf)(2)], J. Electroanal. Chem. 596 (2006) 131-140.
D.S. Silvester, R.G. Compton, Electrochemistry in room temperature ionic liquids: A review and some possible applications, Zeitschrift Fur Physikalische Chem.-Inter. J. Res. Phys. Chem. Chem. Phys. 220 (2006) 1247-1274.
M.C. Kroon, W. Buijs, C.J. Peters, G.J. Witkamp, Decomposition of ionic liquids in electrochemical processing, Green Chem. 8 (2006) 241-245.
T. Ueki, M. Watanabe, Macromolecules in Ionic Liquids: Progress, Challenges, and Opportunities, Macromolecules 41 (2008) 3739-3749.
D.S. Moore, Recent Advances in Trace Explosives Detection Instrumentation, Sens. Imaging 8 (2007) 9-38.
M. Nambayah, T.I. Quickenden, A quantitative assessment of chemical techniques for detecting traces of explosives at counter-terrorist portals, Talanta 63 (2004) 461-467.
D.S. Moore, Instrumentation for trace detection of high explosives, Review of Scientific Instrumnets 75 (2004) 2499-2512.
S.J. Toal, W.C. Trogler, Polymer sensors for nitroaromatic explosives detection, J. Mater. Chem. 16 (2006) 2871-2883.
A. Cyr, E. Laviron, J. Lessard, Electrochemical-Behavior of Nitrobenzene and Phenylhydroxylamine on Copper Rotating-Disk Electrodies, J. Electroanal. Chem. 263 (1989) 69-78.
X.X. Jin, L. Yu, D. Garcia, R.X. Ren, X.Q. Zeng, Ionic Liquid high-temperature gas sensor array, Anal. Chem. 78 (2006) 6980-6989.
L.J. Nunez-Vergara, M. Bonta, P.A. Navarrete-Encina, J.A. Squella, Electrochemical characterization of ortho and meta-nitrotoluene derivatives in different electrolytic media. Free radical formation, Electrochim. Acta 46 (2001) 4289-4300.
L. Agui, D. Vega-Montenegro, P. Yanez-Sedeno, J.M. Pingarron, Rapid voltammetric determination of nitroaromatic explosives at electrochemically activated carbon-fibre electrodes, Anal. Bioanal. Chem. 382 (2005) 381-387.
J.C. Chen, J.L. Shih, C.H. Liu, M.Y. Kuo, J.M. Zen, Disposable electrochemical sensor for determination of nitroaromatic compounds by a single-run approach, Anal. Chem. 78 (2006) 3752-3757.

S. Hrapovic, E. Majid, Y. Liu, K. Male, J.H.T. Luong, Metallic nanoparticle-carbon nanotube composites for electrochemical determination of explosive nitroaromatic compounds, Anal. Chem. 78 (2006) 5504-5512.

D.L. Lu, A. Cagan, R.A.A. Munoz, T. Tangkuaram, J. Wang, Highly sensitive electrochemical detection of trace liquid peroxide explosives at a Prussian-blue 'artificial-peroxidase' modified electrode, Analyst 131 (2006) 1279-1281.

S.Y. Ly, D.H. Kim, M.H. Kim, Square-wave cathodic stripping voltammetric analysis of RDX using mercury-film plated glassy carbon electrode, Talanta 58 (2002) 919-926.

N. P. Saravanan, S. Venugopalan, N. Senthilkumar, P. Santhosh, B. Kavita, H.G. Prabu, Voltammetric determination of nitroaromatic and nitramine explosives contamination in soil, Talanta 69 (2006) 656-662.

J. Wang, Microchip devices for detecting terrorist weapons, Anal. Chim. Acta 507 (2004) 3-10.

J. Wang, R.K. Bhada, J.M. Lu, D. MacDonald, Remote electrochemical sensor for monitoring TNT in natural waters, Anal. Chim. Acta 361 (1998) 85-91.

J. Wang, S.B. Hocevar, B. Ogorevc, Carbon nanotube-modified glassy carbon electrode for adsorptive stripping voltammetric detection of ultratrace levels of 2,4,6-trinitrotoluene, Electrochem. Commun. 6 (20014) 176-179.

J. Wang, F. Lu, D. MacDonald, J.M. Lu, M.E.S. Ozsoz, K.R. Rogers, Screen-printed voltammetric sensor for TNT, Talanta 46 (1998) 1405-1412.

J. Wang, M. Pumera, Dual conductivity/amperometric detection system for microchip capillary electrophoresis, Anal. Chem. 74 (2002) 5919-5923.

J. Wang, S. Thongngamdee, D.L. Lu, Sensitive voltammetric sensing of the 2,3-dimethyl-2,3-dinitrobutane (Dmnb) explosive taggant, Electroanalysis 18 (2006) 971-975.

H.X. Zhang, A.M. Cao, J.S. Hu, L.J. Wan, S.T. Lee, Electrochemical sensor for detecting ultratrace nitroaromatic compounds using mesoporous SiO2-modified electrode, Anal. Chem. 78 (2006) 1967-1971.

H.X. Zhang, J.S. Hu, C.J. Yan, L. Jiang, L.J. Wan, Functionalized carbon nanotubes as sensitive materials for electrochemical detection of ultra-trace 2,4,6-trinitrotoluene, Phys. Chem. Chem. Phys. 8 (2006) 3567-3572.

X.S. Zhu, C.H. Ahn, On-chip electrochemical analysis system using nanoelectrodes and bioelectronic CMOS chip, Ieee Sensors J. 6 (2006) 1280-1286.

http://en.wikipedia.org/wiki/Trinitrotoluene. (May 15, 2009) pp. 1-5.

M.H. Valkenberg et al., "Immobilisation of Ionic Liquids on Solid Supports," Green Chemistry, vol. 4, p. 88-93 (2002).

C.P. Mehnert et al., "Supported Ionic Liquid Catalysis Investigated for Hydrogenation Reactions," Chem. Comm., p. 3010-3011 (2002).

* cited by examiner

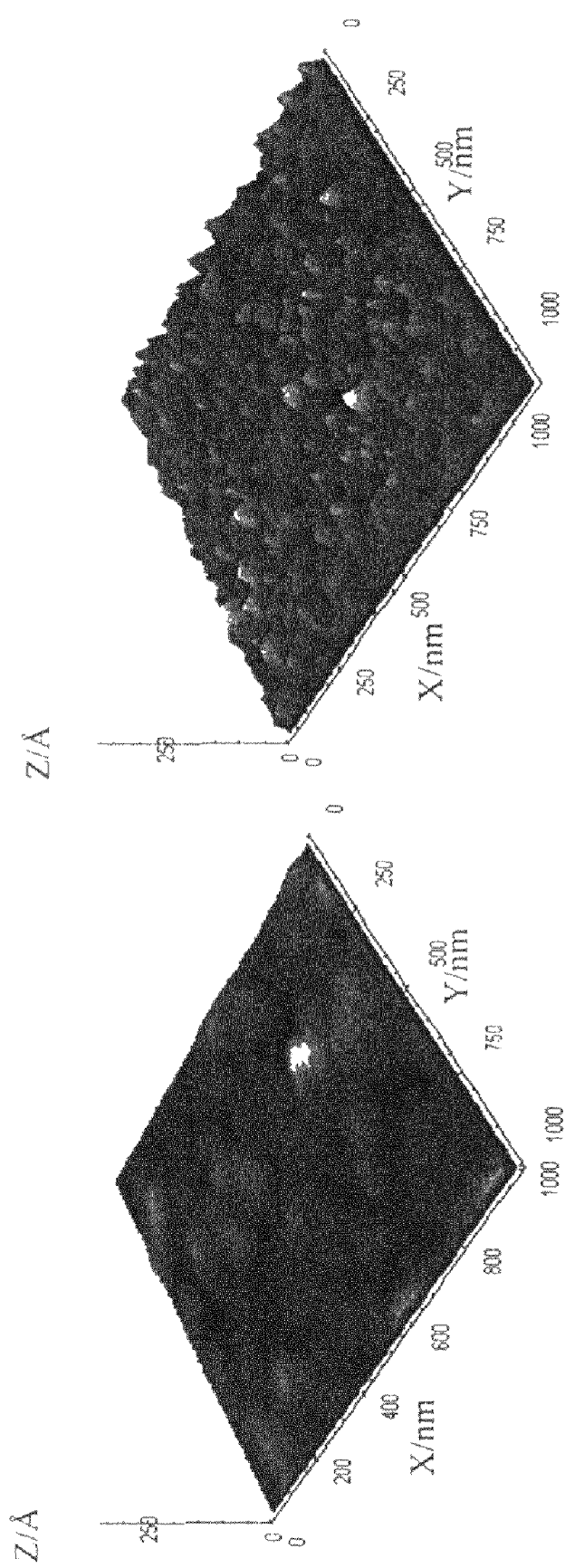

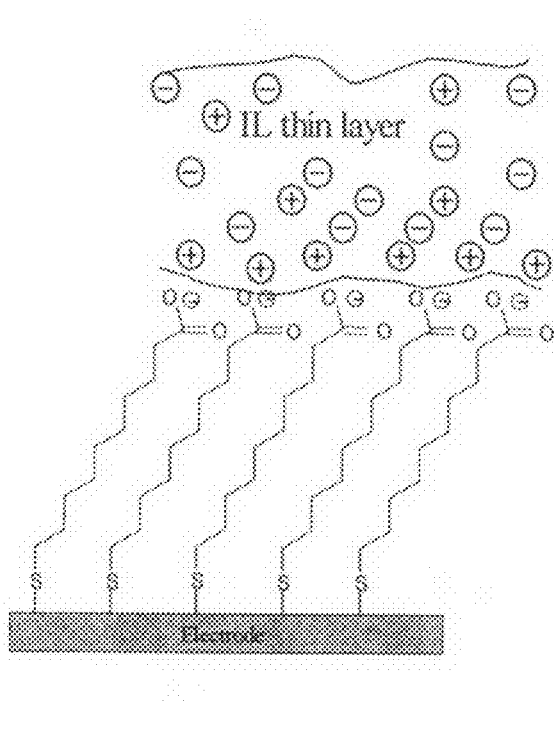
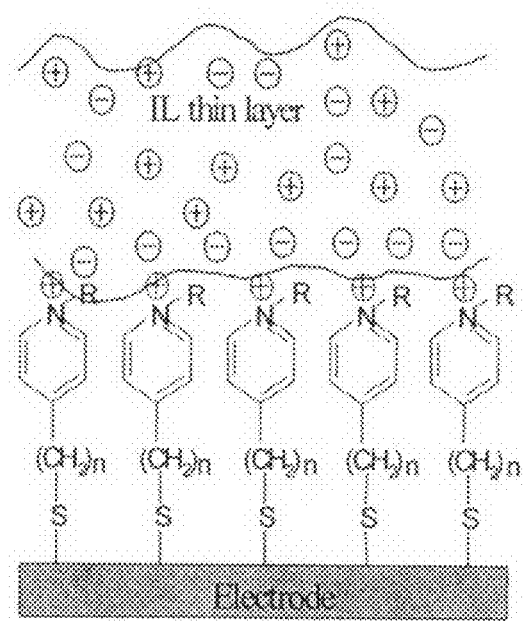
Figure 8A                    Figure 8B

DEVICES WITH SURFACE BOUND IONIC LIQUIDS AND METHOD OF USE THEREOF

CROSS-REFERENCE TO RELATED APPLICATIONS

This application claims benefit of U.S. Provisional Application No. 60/787,594, filed Mar. 30, 2006, which is incorporated herein by reference in its entirety.

STATEMENT REGARDING FEDERALLY SPONSORED RESEARCH OR DEVELOPMENT

This research was partly supported by grants from the National Institutes of Health (NIH R33EB00672 B1). The U.S. government has certain rights to this invention.

BACKGROUND OF THE INVENTION (1) Field of the Invention

The present invention relates generally to devices comprising surface bound ionic liquids for solvating organic compounds. Specifically, the present invention relates to piezoelectric gas sensors with bound films of ionic liquids which are capable of detecting volatile organic compounds such as both polar and nonpolar organic vapors and some inorganic gases such as carbon dioxide at both room and high temperature.

(2) Description of the Related Art

Room-temperature ionic liquids are a relatively new class of compounds containing organic cations and anions, which melt at or close to room temperature. An early group of ionic liquids reported by Osteryoung et al. was composed of a mixture of 1-butylpyridinium chloride and aluminum chloride that was liquid at room temperature (Decastro, C., et al., J. Catalysis, 196, 86-94 (2000); and Chum, H. L., et al., J. Am. Chem. Soc., 97, 3264 (1975)). Soon after, a series of ILs based on the cations of alkylpyridinium or dialkylimidazolium were developed. The anions vary from halides, such as $Cl^-$, $Br^-$ or $AlCl_4^-$ to coordinates, such as $BF_4^-$, $PF_6^-$, $SbF_6^-$, or $NO_3^-$, $SO_4^-$, $CuCl_2^-$, and organics, such as $CH_3SO_3^-$, or $(CF_3SO_2)_2N^-$ (Zhao, D. B., et al., Catalysis Today, 74, 157-189 (2002); and Olivier-Bourbigou, H., et al., J. Molecular Catalysis A: Chemical, 182-183, 419-437 (2002)). In the last decade, ILs based on cations of tetraalkylammonium or tetraalkylphosphonium and anions of phosphinate (Robertson, A. J., et al., WO 2002079212; Bradaric, C. J., et al., in Industrial Preparation of Phosphonium Ionic Liquids, ACS Symposium Series 856; Roger, R. D., et al., Edt. American Chemical Society (2003)), alkanesulfonate and alkylbenzenesulfonate (Wasserscheid, P., et al., in New Ionic Liquids Based on Alkylsulfate and Alkyl Oligoether Sulfate Anions: Synthesis and Applications, ACS symposium Series 856, Ionic Liquids as Green Solvents, Progress and Prospects, R. D. Roger and K. R. Seddon Ed., American Chemical Society (2003)) were developed, which are "pure organic" ILs that are more stable, especially at relatively higher temperatures, less toxic and more hydrophobic. Due to its unique properties and increasing availability, room temperature ionic liquids have attracted significant research interest in the past few years.

In contrast to conventional organic solvents that are composed of molecular entities such as DMSO, DMF, $CH_2Cl_2$, $CHCl_3$, or THF, ionic liquids have unique properties (Seddon, K. R., in Ionic Liquids for Clean Technology, J. Chem. Tech. Biotech, 68, 315-316 (1997)). They have no significant vapor pressure, thus allowing chemical processes to be carried out with essentially zero emission of toxic organic solvents into the environment. Consequently, they have been considered a possibly environmentally friendly, recyclable media for synthetic organic chemistry, separation sciences and other chemical sciences and engineering (Welton, T, in Room-Temperature Ionic Liquids: Solvents for synthesis and Catalysis, Chem. Rev., 99, 20071-2083 (1999)). For example, ionic liquids have been used as solvents for organic reactions (nucleophilic and electrophilic reactions including acid catalyzed reactions), transition metal catalyzed reactions, and biotransformations (Rogers, R. D., et al., Ionic Liquids: Industrial Application of Green Chemistry, ACS Symposium Series 818, (2002); and Rogers, R. D., et al., Ionic Liquids as Green Solvents: Progress and Prospects, ACS Symposium Series 856 (2002)). In addition to enhanced reaction rates and improved chemo- and regioselectivities relative to other organic solvents, ILs also provide potential solutions for biphasic separation of reaction products via extraction, i.e. products can be obtained through distillation from these non-volatile reaction media which eliminates the need for noxious organic solvents (Visser, A. E., et al., in Task-specific ionic liquids for the extraction of metal ions from aqueous solutions, Chem. Comm. 135 (2001); Bates, E. D., et al., J. Am. Chem. Soc. 124, 926 (2002)). Ionic liquids usually have low miscibility with a number of organic solvents (such as ethers, hexane, or ethyl acetate) as well as supercritical carbon dioxide (Blanchard, L. A., et al., Nature 399, 28 (1999). Consequently, organic compounds can be extracted into supercritical carbon dioxide from ionic liquids.

Ionic liquids possess high ion concentration, high heat capacity and good electrochemical stability. They prove to be excellent candidates for highly efficient heat transfer fluids, supporting media for catalysts as well as electrochemical devices including super capacitors, fuel cells, lithium batteries, photovoltaic cells, electrochemical mechanical actuators and electroplating (Seddon, K. R., J. Chem. Tech. Biotech, 68, 315-316 (1997)). Recently, reports for the use of ILs as lubricants for steels joints (Welton, T., Chem. Rev., 99, 2071-2083 (1999); Rogers, R. D., et al., ACS Symposium Series 818 (2002); and Rogers, R. D., et al., ACS Symposium Series 856 (2002)) show that the ILs exhibits excellent friction-reduction, antiwear properties, both in air and in vacuum, which are superior to phosphazene and perfluoropolyether.

Even though significant progresses in the study of ILs have been made in the past decade, the bulk of current research of ILs is focused on their use as solvents for chemical reactions, separations and electrochemistry. Limited efforts have been made to explore ILs potential for analytical applications (Baker, G. A., et al., in An Analytical view of ionic liquids, The Analyst, 130, 800-808 (2005)). Much fundamental research effort is needed to bring forth the benefits of ILs. There is a need to address this issue and explore ionic liquids surface chemistry and its application as gas sensing materials.

Gas sensors are of increasing interest because of their potential for widespread application in ambient air monitoring, occupational health and safety, biomedical diagnostics, industrial process control, and military and civilian counter-terrorism. Sorptive-polymer interface layers have been extensively explored to temporarily concentrate the vapors near the sensor surface and to facilitate detection by whatever transduction mechanism is employed in the sensing devices (Blanchard, L. A., Nature 399, 28 (1999)). It is now generally accepted that the non-bonding vapor-polymer sorption interactions in sensor arrays do not afford sufficient collective selectivity for quantitative determinations of more than a few vapors simultaneously regardless of the number of sensors or the sensor technology employed (Handy, S. T., Chem. Eur. J., 9, 2938-2944 (2003); Ding, J., et al., Chem. Mater., 15, 2392-2398 (2003); Jensen, M. P., et al., J. Am. Chem. Soc. 125, 15466-15473 (2003); Yang, C., et al., J. phys. Chem. B, 107, 12981-12988 (2003); Barisci, J. N., et al., Electrochem. Commun. 6, 22-27 (2004); Wang, P., et al., J. Phys. Chem. B, 107, 13280-13285 (2003)). Ionic liquids with their unique properties could potentially overcome above limitation for gas detection: (1) ILs are excellent solvents that can support many types of solvent-solute interactions (hydrogen bond, π-π, dipolar, ionic., and the like). Many different interaction types may be simultaneously present in ILs, and the resulting properties of the ILs depend on which interactions are dominant. Consequently, surface design of ILs can be used to fit a particular sensing application; (3) ILs have negligible vapor pressure so that there is no drying out of the electrolyte, which is a serious problem for sensors using solid polymer electrolyte films, which reduces hazards, associated with flash points and flammability; (4) ILs possesses high thermal stability (Liu, W. M., et al., Tribology Letters, 13, 81-85 (2002)). Most ILs show typical decomposition temperatures of 350+° C. This remarkable thermal stability has important implications in the use of ILs for high temperature sensing; (5) Ionic liquids suppress conventional salvation and solvolysis phenomena, and provide media capable to dissolve a vast range of organic molecules to very high concentrations. One of the most exiting and impressive potential industrial applications of ionic liquid is their use for the storage and delivery of gases that are highly toxic, flammable, and/or reactive. Air Products has developed a subatmospheric ionic-liquid-based technology for storing and delivering gases that offers a number of advantages over the solid physical-adsorption technology. This indicates great potential in organic volatile sensing. (6) Synthetic flexibility of ionic liquids allowing them to be tailored to be chemically independent; One ion could be use to deliver one function and the second ion to deliver a different, completely independent function (Wang, H. Z., et al., Wear, 256, 44-48 (2004)). Functionalized ionic liquids are being developed that not only act as solvents but also as materials for particular applications (Ye, C. F., et al., Wear, 253, 579-584 (2002)). While there are about 300 organic solvents widely used in the chemical industry, there are potentially many more useful ionic liquids; (7) The unique charge properties allow easy construction of IL on preformed templates which could generate complex chemical selective films. In summary, IL's offer tremendous diversity in structural and chemical properties and their unique properties offer an excellent opportunity to design an array of chemically selective IL films and explore their application in pattern recognition for various analytes.

Many research groups are developing new materials and transducers for gas sensing with particular emphasis on optimizing interface properties among the gas phase, the sensitive materials and the transducer. For example, self-assembled monolayers (SAM) have been used to construct functional organic surfaces (Baker, G. A., et al., The Analyst, 130-800-808 (2005)). They have the advantage of being easily and reproducibly synthesized, and the analysis rate is typically fast since they do not need to penetrate through a diffusion barrier. The disadvantage of SAM is that the chemical selectivity depends only on the terminal groups, making the degree of chemical selectivity that can be engineered into simple SAM not as great as in thicker or more complex materials. Moreover, the total number of receptors incorporated in the film and thus the dynamic range and sensitivity of the sensor, is limited by the surface area of the substrate. In order to overcome the disadvantages of SAM, stepwise self-assembled bilayers were reported (Baker, G. A., et al., The Analyst, 130, 800-808 (2005)), which can produce films of complex molecules and molecular assemblies. However, self-assembled films of complex molecules and molecular assemblies are difficult to prepare.

Thin films made from ILs can perform well as sensor interfaces and provide additional control over selectivity and sensitivity when interacting with analytes in gas phase. Most organic solvents or vapors are soluble in ILs. Therefore, the partition process will reach equilibrium very fast after the sensor is exposed to the vapors. This ensures a fast response and excellent reversibility. At equilibrium, the distribution of organic vapors in the IL phase and the gas phase will depend on the partial pressure of the vapors so quantitative measurement is feasible. ILs have zero vapor pressure and work in a very large temperature range which is ideal for industrial high temperature sensing applications.

ILs possess high ion concentration, high heat capacity and good electrochemical stability. They prove to be excellent candidates for highly efficient heat transfer fluids, supporting media for catalysts as well as electrochemical devices including supercapacitors, fuel cells, lithium batteries, photovoltaic cells, electrochemical mechanical actuators and electroplating (Handy, S. T., Chem. Eur. J. 9 2938-2944 (2003); Ding, J., et al., Chem. Mater. 15 2392-2398 (2003: Jensen, M. P. et al., J. Am. Chem. Soc. 125 15466-15473 (2003); Yang, C., et al., J. Phys. Chem. B, 107 12981-12988 (2003: Barisci, J. N., et al., Electrochem. Commun. 6 22-27 (2004; Wang, P., et al., J. Phys. Chem. B, 107 13280-13285 (2003)). Recently, reports for the use of ILs as lubricants for steels joints (Liu, W. M., et al., Tribology Letters 13 81-85 (2002: Wang, H. Z., et al., Wear 256 44-48 (2004: and Ye, C. F., et al., Wear, 253 579-584 (2002: show that the ILs exhibits excellent friction-reduction, antiwear properties, both in air and in vacuum, which are superior to phosphazene and perfluoropolyether.

Identifying and correcting emissions from high-polluting vehicles requires small sensors working at high temperatures to monitor pollutants in exhaust gas or leaking fuels (Tsang et al., *J. Phys. Chem. B,* 2001, 105, 5737-5742; Kaltenpoth et al., *Anal. Chem.,* 2003, 75, 4756-4765). High temperature gas sensing is conventionally achieved by using semi-conductive metal oxides, such as $SnO_2$ and $TiO_2$ (Dutta et al., *J. Phys. Chem. B,* 1999, 103, 4412-4422; Ikohura and Watson, *The Stannic Oxide Gas Sensor; CRC Press: Boca Raton, Fla.,* 1994; Zhu et al., *Anal. Chem.,* 2002, 74, 120-124). The resistance of metal oxides changes in the presence of organic vapors, CO or $H_2$. It takes relatively a long time to reach equilibrium for the sorption of analytes from gas phase onto the metal oxides, especially for porous materials. The dependency of the resistance of the metal oxides on the vapor concentration is not linear, which reduces the accuracy of quantitative analysis (Simon et al. *J. Comb. Chem.,* 2002, 4, 511-515). Some metal oxides work only at temperatures higher than a "switch on" value, e.g. >700° C. for $SrTiO_3$(Hu et al., *J. Phys. Chem. B,* 2004, 108, 11214-11218; Wang et al., *J. Am. Chem. Soc.,* 2003, 125, 16176-16177; Dutta et al., *Chem. Mater.,* 2004, 16, 5198-5204).

Rubbery polymers with low glass transition temperatures ($T_g$) have been used as coatings for detection of nonpolar or weakly polar organic vapors (Grate et al., *Anal. Chem.,* 1993, 65, 987A). The vapor sorption in rubbery polymers is reversible and equilibrium is attained rapidly (Grate et al., *Anal. Chem.,* 1993, 65, 987A; (a) Jarrett and Finklea, *Anal. Chem.,* 1999, 71, 353; (b) Shinar et al., *Anal. Chem.,* 2000, 72, 5981; (c) Zellers et al., *Anal. Chem.,* 1995, 67, 1092; (d) Patrash and Zellers, *Anal. Chem.,* 1993, 65, 2055). However, the mechanical properties of rubbery polymers strongly depend upon temperature (U. W. Gedde, *Polymer Physics,* Kluwer Academic Publ., Doedrecht, Netherlands, 1999). Most polymer materials with low $T_g$ are not stable at high temperatures. Therefore, applications of polymer materials for high temperature vapor sensing are limited. Furthermore, if the vapors cannot absorb on the materials, the large surface-area to volume ratio sensing materials, such as graphite ((a) Jarrett and Finklea, *Anal. Chem.*, 1999, 71, 353; (b) Shinar et al., Anal. Chem., 2000, 72, 5981; (c) Zellers et al., Anal. Chem., 1995, 67, 1092; (d) Patrash and Zellers, *Anal. Chem.*, 1993, 65, 2055) or oxides (Dutta et al., *J. Phys. Chem. B*, 1999, 103, 4412-4422; Ikohura and Watson, *The Stannic Oxide Gas Sensor*; CRC Press: Boca Raton, Fla., 1994; Zhu et al., *Anal. Chem.*, 2002, 74, 120-124) would not work for high temperature gas sensing.

U.S. Pat. No. 4,236,893 to Rice, U.S. Pat. No. 4,242,096 to Oliveira et al., U.S. Pat. No. 4,246,344 to Silver III, U.S. Pat. No. 4,314,821 to Rice, U.S. Pat. No. 4,735,906 to Bastiaans, and U.S. Pat. No. 6,087,187 to Wiegland et al. each teach using a piezoelectric sensor for the detection of an analyte in a liquid sample. U.S. Patent Application Publication Nos. 2003/0077222, 2003/0073133, 2003/0072710, 2003/0068273, 2003/0053950, and 2003/0049204, all to Leyland-Jones, discloses immunosensors which in particular embodiments have antibodies, Fab fragments, or scFv polypeptides immobilized on the surface thereof.

U.S. Patent Application Nos. 2002/0094531 to Zenhausern teach sensing probes such as a QCM for detecting a biological analyte of interest in gaseous, vapor, or liquid forms. The sensing probes are coated with various materials, such as polymers, ion exchange resins, porous silicon, silanes, thiols, and oxides. However ionic liquids are not taught as a coating for the sensing probes.

U.S. Patent Application Nos. 2002/0142477 to Lewis et al. teach organic vapor measurement using a polymer-coated quartz crystal microbalance. The quartz crystal microbalance crystals are coated with polymers including poly (ethylene-co-vinyl acetate) with 25% acetate (PEVA) and poly(caprolactone) (PCL) polymer films.

There is a need for improved devices which rely upon ILs.

Objects

It is an object of the present invention to provide devices with bound ionic liquid films, particularly for use in piezoelectric gas sensors.

It is further an object of the present invention to provide such piezoelectric gas sensors which are capable of detecting both polar and nonpolar organic vapors.

It is an object of the present invention to provide devices where an ionic liquid film is bound to an exposed surface of a substrate.

It is still further an object of the present invention to provide gas sensors which have a fast linear and reversible response.

These and other objects will become increasingly apparent by reference to the following description.

SUMMARY OF INVENTION

The present invention provides a device which comprises: a substrate with an exposed surface; and an ionic liquid film which is bound to the exposed surface so as to enable the ionic liquid to solvate an organic chemical which would be solvated by an unbound film of the ionic liquid. In further embodiments of the device, the ionic liquid film is phosphonium dodecylbenzene-sulfonate. In still further embodiments, the phosphonium dodecylbenzene-sulfonate is $P_{6,6,6,14}$DBS. In further embodiments, the ionic liquid film is bound to the surface by means of a self-assembled monolayer (SAM). In still further embodiments, the self-assembled monolayer (SAM) comprises carboxylic acid terminal groups or pyridine terminal groups. In further embodiments of the device, the ionic liquid film is bound to the surface by means of one or more polyelectrolyte or conductive polymer on the surface. In some embodiments, the conductive polymer is polyaniline. In still further embodiments, the ionic liquid film is bound to the surface by means of one or more polyionic or zwitterionic liquids. In some embodiments, at least one of the zwitterionic liquids comprise imidazolium, tetraalkylammonium or tetraalkylphosphonium groups. In some embodiments, the zwitterionic liquid further comprises sulfonate groups. In further embodiments, the organic chemical is methane.

The present invention provides a method of solvating an organic sample comprising: providing a device which comprises a substrate with an exposed surface; and an ionic liquid film which is bound to the exposed surface so as to enable the ionic liquid to solvate an organic chemical which would be solvated by an unbound film of the ionic liquid; and providing the organic chemical on the exposed surface of the ionic liquid film so that the film solvates the organic chemical. In further embodiments of the method, the ionic liquid is phosphonium dodecylbenzene-sulfonate. In still further embodiments, the phosphonium dodecylbenzene-sulfonate is $P_{6,6,6,14}$ DBS. In further embodiments, the organic chemical is methane.

The present invention provides a gas sensor for determining the concentration of an organic vapor in a gaseous sample comprising: a quartz crystal microbalance having a transducer surface; and an ionic liquid film bound to the transducer surface of the quartz crystal microbalance, wherein when the organic vapor is present in the gaseous sample it is absorbed in the ionic liquid film on the transducer surface and changes a resonant frequency of the quartz crystal microbalance. In further embodiments, the ionic liquid film is bound to the surface by means of a self-assembled monolayer (SAM). In still further embodiments, the self-assembled monolayer (SAM) comprises carboxylic acid terminal groups or pyridine terminal groups. In further embodiments of the device, the ionic liquid film is bound to the surface by means of one or more polyelectrolyte or conductive polymer on the surface. In some embodiments, the conductive polymer is polyaniline. In still further embodiments, the ionic liquid film is bound to the surface by means of one or more polyionic or zwitterionic liquids. In some embodiments, at least one of the zwitterionic liquids comprise imidazolium, tetraalkylammonium or tetraalkylphosphonium groups. In some embodiments, the zwitterionic liquid further comprises sulfonate groups. In further embodiments, the organic chemical is methane.

The present invention provides a method of determining the concentration of an organic vapor in a gaseous sample comprising: providing a gas sensor for detecting the concentration of an organic vapor in a gaseous sample comprising a quartz crystal microbalance having a transducer surface; and an ionic liquid film bound on the transducer surface of the quartz crystal microbalance, wherein when the organic vapor is present in the gaseous sample it is absorbed in the ionic liquid film on the transducer surface and changes a resonant frequency of the quartz crystal microbalance; providing a reference gas to the transducer surface of the gas sensor; measuring a first reference frequency of the gas sensor; providing the gaseous sample to the transducer surface of the gas sensor; measuring a second resonant frequency of the gas sensor; subtracting the first resonant frequency from the second resonant frequency to provide a frequency change; and determining the concentration of the organic vapor in the gaseous sample by the frequency change. In further embodiments of the method, the ionic liquid is phosphonium dodecylbenzene-sulfonate. In still further embodiments, the phosphonium dodecylbenzene-sulfonate is $P_{6,6,6,14}$ DBS.

The present invention provides a method of determining the concentration of an organic vapor in a gaseous sample comprising: providing a first gas sensor and a second gas sensor, the first and second gas sensors for detecting the concentration of an organic vapor in a gaseous sample, the sensors comprising a quartz crystal microbalance having a transducer surface, and an ionic liquid film bound on the transducer surface of the quartz crystal microbalance, wherein when the organic vapor is present in the gaseous sample it is absorbed in the ionic liquid film on the transducer surface and changes a resonant frequency of the quartz crystal microbalance; providing a reference gas to the first gas sensor; providing the gaseous sample to the second gas sensor; measuring a resonant frequency of the first sensor; measuring a resonant frequency of the second sensor; subtracting the resonant frequency of the first sensor from the resonant frequency of the second sensor to provide a frequency difference; and determining the concentration of the organic vapor in the gaseous sample by the frequency difference. In still further embodiments of the method, the ionic liquid is phosphonium dodecylbenzene-sulfonate. In still further embodiments, the phosphonium dodecylbenzene-sulfonate is $P_{6,6,6,14}$ DBS.

The present invention provides a method of detecting an unknown organic vapor in a gaseous sample comprising: providing an array of gas sensors for detecting an organic vapor in a gaseous sample, each of the sensors comprising a quartz crystal microbalance having a transducer surface, and an ionic liquid film bound on the transducer surface, wherein when the organic vapor is present in the gaseous sample it is absorbed in the ionic liquid film on the transducer surface and changes a resonant frequency of the quartz crystal microbalance; providing a reference gas to the array; measuring a reference frequency of each of the sensors in the array; providing the gaseous sample to the array; measuring a resonant frequency of each of the sensors of the array; subtracting the resonant frequency of each of the sensors from the resonant frequency of each of the sensors to provide a frequency difference for each of the sensors of the array; and detecting the organic vapor in the gaseous sample by the frequency difference for each of the sensors in the array.

The substance and advantages of the present invention will become increasingly apparent by reference to the following drawings and the description.

BRIEF DESCRIPTION OF THE DRAWINGS

FIG. 3A shows Δf as a function of T of ionic liquid $P_{66614}$OMS.

FIGS. 4A and B are AFM images of a polished Au QCM surface (FIG. 4A), and after it was modified with IL thin film (FIG. 4B). Contact mode.

FIGS. 8A and B show immobilization via electrostatic interaction between cations/anions of ILs and SAMs.

DETAILED DESCRIPTION OF THE INVENTION

Figure 1:
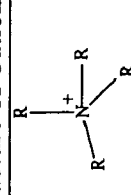
FIG. 1 shows structures and formulas of ILs.

All patents, patent applications, government publications, government regulations, and literature references cited in this specification are hereby incorporated herein by reference in their entirety. In case of conflict, the present description, including definitions, will control.

The term "bound" as used herein means to hold or immobilize in place for the purpose of use of the IL. In some embodiments, the IL is bound to a surface by means of electrostatic charge coupling or hydrogen bonding. In some embodiments, a polymer (including, but not limited to a conductive polymer, such as polyaniline) can be formed from monomer structures having functional side groups. Thus, conductive polymer templates having additional functional groups can be generated for binding the IL to a surface. The functional groups can be used to immobilize ionic liquids with preferred orientation via various molecular interactions (ie. hydrogen bond, p-p, dipolar, ionic. etc.) of ionic liquids and conductive polymer functional groups.

The term "QCM" as used herein refers to a quartz crystal microbalance. The QCM is used to measure a mass that is applied to the QCM by means of the change in resonance frequency of a piezoelectric quartz crystal when biased with an alternating current. Some examples of quartz crystal microbalance devices that can be used in the present invention include QCM devices available from Maxtek Inc. of Santa Fe Springs, Calif. Other QCM devices which can be used in the present invention are described in U.S. Pat. No. 4,236,893 to Rice, U.S. Pat. No. 4,242,096 to Oliveira et al., U.S. Pat. No. 4,246,344 to Silver III, U.S. Pat. No. 4,314,821 to Rice, U.S. Pat. No. 4,735,906 to Bastiaans, U.S. Pat. No. 5,314,830 to Anderson et al., U.S. Pat. No. 5,932,953 to Drees et al., and U.S. Pat. No. 6,087,187 to Wiegland et al., U.S. Pat. No. 6,890,486 to Penelle, U.S. Pat. No. 6,848,299 to Paul et al., U.S. Pat. No. 6,706,977 to Cain et al., U.S. Pat. No. 6,647,764 to Paul et al., U.S. Pat. No. 6,492,601 to Cain et al., U.S. Pat. No. 6,439,765 to Smith, U.S. Pat. No. 6,190,035 to Smith, U.S. Pat. No. 6,106,149 to Smith, U.S. Pat. No. 5,885,402 to Esquibel, U.S. Pat. No. 5,795,993 to Pfeifer et al., U.S. Pat. No. 5,706,840 to Schneider, U.S. Pat. No. 5,616,827 to Simmermon et al., U.S. Pat. No. 5,484,626 to Storjohann et al., U.S. Pat. No. 5,282,925 to Jeng et al., U.S. Pat. No. 5,233,261 to Wajid, U.S. Pat. No. 5,201,215 to Granstaff et al., U.S. Pat. No. 4,999,284 to Ward et al., and U.S. Pat. No. 4,788,466 to Paul et al. Examples of control circuitry for quartz crystal microbalances and methods for detecting materials using piezoelectric resonators are described in U.S. Pat. No. 5,117,192 to Hurd and U.S. Pat. No. 5,932,953 to Drees et al. Some methods which have been used to attach substances to surfaces such as the receptor surfaces of the QCM are described in U.S. Pat. No. 6,475,809 to Wagner et al., U.S. Pat. No. 6,475,808 to Wagner et al., U.S. Pat. No. 6,368,877 to Zhang et al., U.S. Pat. No. 6,319,674 B1 to Fulcrand et al., and U.S. Pat. No. 5,622,826 to Varma, and Yang et al., Nature Materials 1: 253-257 (2002). Each of the above references are hereby incorporated herein by reference in their entirety.

The term "ionic liquid" or "IL" as used herein generally refers to a liquid salt consisting solely of ions. The term encompasses room-temperature ionic liquids which melt at or close to room temperature, and typically they are salts whose melting point is below approximately 100° C. Preferably the ionic liquids have negligible vapor pressure and have high thermal stability. The term ionic liquid (IL) encompasses liquids having organic cations and anions. The ILs typically comprise bulky asymmetric organic cations such as 1-alkyl-3-methylimidazolium, 1-alkylpyridinium, N-methyl-N-alkylpyrrolidinium or ammonium ions and a wide range of anions. Many ionic liquids are phosphonium salts. Phosphonium salts are more thermally stable than the corresponding ammonium salts and imidazolium salts, however any can be used in the present invention. Examples of some ionic liquids useful for the present invention include, but are not limited to, those ILs listed herein and those described in U.S. Pat. No. 6,852,229 to Mehnert et al., U.S. Patent Application Publication No. 2003/0204041 to Laas et al., U.S. Patent Application Publication No. 2004/0054231 to Abbott et al., U.S. Patent Application Publication No. 2004/0262578 to Wasserscheid et al., and U.S. Patent Application Publication No. 2005/0005840 to Bonrath et al. hereby incorporated herein by reference in their entirety.

The term "organic vapor" as used herein refers to gaseous phase organic molecules. The term encompasses both polar organic molecules (including, but not limited to ethanol and dichloromethane) and nonpolar organic molecules (including, but not limited to heptane and benzene).

This invention relates to the design and control of the molecular character of the ionic liquids on electrode surface for their applications in gas sensing, especially their application in sensor arrays and high temperature sensing for volatile organic and automobile tailpipe emission exhaust. High-temperature gas sensors are described in U.S. patent application Ser. No. 11/522,833 to Zeng, which is incorporated herein by reference in its entirety. A great deal of attention has been given to imidazolium ionic liquids which consist of halogen containing anions such as $[AlCl_4]^-$, $[PF_6]^-$, $[BF_4]^-$, $[CF_3SO_3]^-$, or $[N(CF_3SO_2)_2]^-$. For many technical applications, the presence of halogen atoms in the imidazolium ionic liquid can cause concerns if the hydrolytic stability of the anion is poor (e.g. for choloroaluminate and hexaflurophosphate systems) or if a thermal treatment of the spent ionic liquid is desired. The present invention focuses on phosphonium ionic liquids with alkanesulfonate and alkylbenzenesulfonate anions (Robertson, A. J., et al., WO 2002079212; and Bradaric, C. J., et al., in Industrial preparation of Phosphonium Ionic Liquids, ACS symposium Series 856, Ionic Liquids as Green Solvents, Progress and Prospects, R. D. Roger and K. R. Seddon Edt. American Chemical Society (2003); and Wasserscheid, P., et al., in New Ionic Liquids Based on Alkylsulfate and Alkyl Oligoether Sulfate Anions: Synthesis and Applications, ACS symposium Series 856, Ionic Liquids as Green Solvents, Progress and Prospects, R. D. Roger and K. R. Seddon Ed., American Chemical Society, (2003)). They possess high hydrolytic and thermal stability and acceptable viscosity. Very few investigations of this type of ILs have been reported in the literature. Imidazolium ionic liquids with non-halogen anions are provided for gas sensing.

FIG. 1 shows a table with structures and formulas of ILs. BmiBF$_4$, bmiN (SO$_2$CF$_3$)$_2$ and hpPF$_6$ were prepared following literature procedures, which are base on the metathesis of the corresponding imidazolium chlorides with appropriate salts (Wilkes, J. S., et al., J. Chem. Soc., Chem. Commun., 965 (1992); Bonhote, P., et al., Inorg. Chem., 35, 1168 (1996)). Water-immiscible ionic liquids, such as, bbiN (SO$_2$CF$_3$)$_2$ and bbiPF$_6$, were prepared based on a process known as "one-port synthesis of ionic liquids" (Ren, R. X., et al., WO 0294883 (2002); Ren, R. X., in Green synthesis of Ionic Liquids for Green Chemistry, Chapter 6 in the American Chemical Society Symposium Series #865 Ionic Liquids as Green Solvents: Progress and Prospects, American Chemical Society: Washington, D.C., pp. 70-81 (2003)). By mixing aqueous formaldehyde with two equivalent of 1-butylamine, hexafluorophosphoric acid, or bis(trifluoromethanesulfon) imide and aqueous glyoxal solution, the hydrophobic ionic liquid (lower layer) thus formed can be separated directly from the reaction mixture (Ren, R. X., et al., WO 0294883 (2002)). Sulfonate ionic liquids with various cations were all made via alcohol-to-alkyl halide conversion method, which is also a one-pot synthesis of ionic liquids (Ren, R. X., et al., WO 0351894 (2003)). By using primary alcohols (ROH), suitable acids (HA), the 1,3-dialkylimidazolium halides, pyridinium halides, tetraalkylammonium halides and tetraalkylphosphonium halides (all designated as Q$^+$X$^-$) can be converted to the new ionic liquids (Q$^+$A$^-$) with the anions being the conjugated bases of the acids used.

In FIG. 1, N$_{l,m,n,j}$ and P$_{l,m,n,j}$ represent the tetraalkylammonium and the tetraalkylphosphonium respectively. The subscripted numbers, l, m, n and j represent the numbers of carbons in each alkyl substitutes. For example, N$_{7,7,7,7}$ is tetraheptylammonium. The anion, dodecylbenzenesulfonate (SO$_3$—Ph—C$_{12}$H$_{25}$), was also abbreviated as DBS in the text. bmi and bbi are 1-butyl-3-methylimidazolium and 1,3-dibutylimidazolium, respectively. bei and pmi are 1-butyl-3-ethyl-imidazolium and 1-propyl-3-methyl-imidazolium, respectively. hp and bp are hexylpyridinium and butylpyridinium, respectively.

The table of FIG. 1 lists over twenty ionic liquids, which have been synthesized. Besides using traditional metathesis methods for the synthesis of BF$_4^-$, PF$_6^-$, (CF$_3$SO$_2$)$_2$N$^-$ and phosphinate anion-based ILs, a safer, more efficient and more environmentally friendly ("green") method for synthesis of bisulfate, alkanesulfonate and alkylbenzenesulfonate ionic liquids has been developed (Hsieh, M., et al., Anal. Chem., 76, 1885-1895 (2004)). This novel, innovative technology eliminates the shortcomings in the previously widely used methods of making ionic liquids via anion metathesis approaches which utilize conventional organic solvents and generate aqueous and solid wastes, and have technical difficulty in industrial scale-up. The extension of this technology will be directed at the synthesis of functionalized ionic liquids. Ionic liquids in FIG. 1 are now commercially available through IL-TECH. Other vendors for ILs are Cytec Inc., BASF and Degussa's Oligomers & Silicones.

In the present invention, methods are developed to immobilize ionic liquids or ionic liquid on preformed templates on electrode surfaces with controlled configurations so each film exhibits unique chemical and physical properties (e.g. defined surface morphology, porosity, hydrophobicity, wetability). The immobilized ionic liquid films are characterized by electrochemical techniques (QCM, Network Impedance analyzer), ellipsometry, AFM and ATR and reflectance absorption infrared spectroscopy. The thermodynamics and kinetics of the modified IL film interactions are determined with various gas analytes including major vehicle emission pollutants and volatile organic compounds (e.g. CO$_2$, CO, SO$_2$, NO$_x$, benzene, toluene, dichloromethane, ethanol, acetone, THF, DMF, and etc.). IL/QCM sensor array and high temperature gas sensors are developed based on chemical selective IL films, and pattern-recognition algorithms are developed for IL sensor arrays.

System integration and packaging with JADI for the QCM sensor array.

An IL gas sensor at room and high temperatures (*Chemical Communication*, 2005, 2277-2279) has been described. Ionic liquids have high thermal stability (e.g. typical decomposition temperature is about 350° C. (by TGA) (Zhang, Z., et al., in EPD Congress (2002), P. R. Taylor, ed.; TMS, Warrendale Pa., p. 1999 (2002); Ngo, H. L., et al., Thermochim. Acta, 97, 357-358 (2000); Bonhote, P., e6 al., Inorg. Chem. 35, 1168-1178 (1996); Holbrey, J. D., et al., J. Chem. Soc., Dalton Trans. 2133 (1999); Takahashi, S., et al., Plasmas & Ions, 2, 91-105 (1999)). Reports also show that ionic liquids are able to protect the monellin from thermal degradation. The inventors have demonstrated both tetraalkylphosphonium and tetraalkylammonium IL thin films show enhanced sensitivity and selectively to the organic vapors (ethanol, dichloromethane, heptane or benzene) at room temperature and elevated temperatures as high as 200° C. when comparing to a bare gold electrode.

Figure 2:
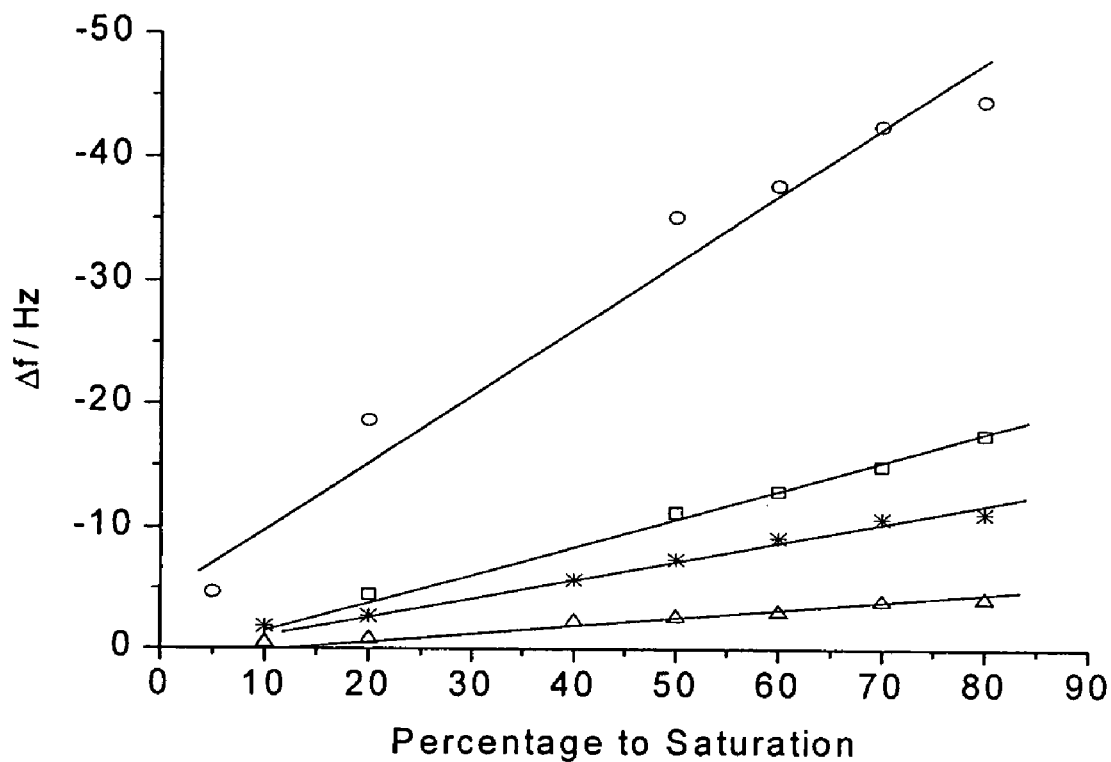
FIG. 2 is a graph showing frequency change vs. concentration of the IL/QCM sensor exposed to ethanol (square), heptane (triangle), benzene (star) and dichloromethane (circle) at 120° C.
Figure 3A:
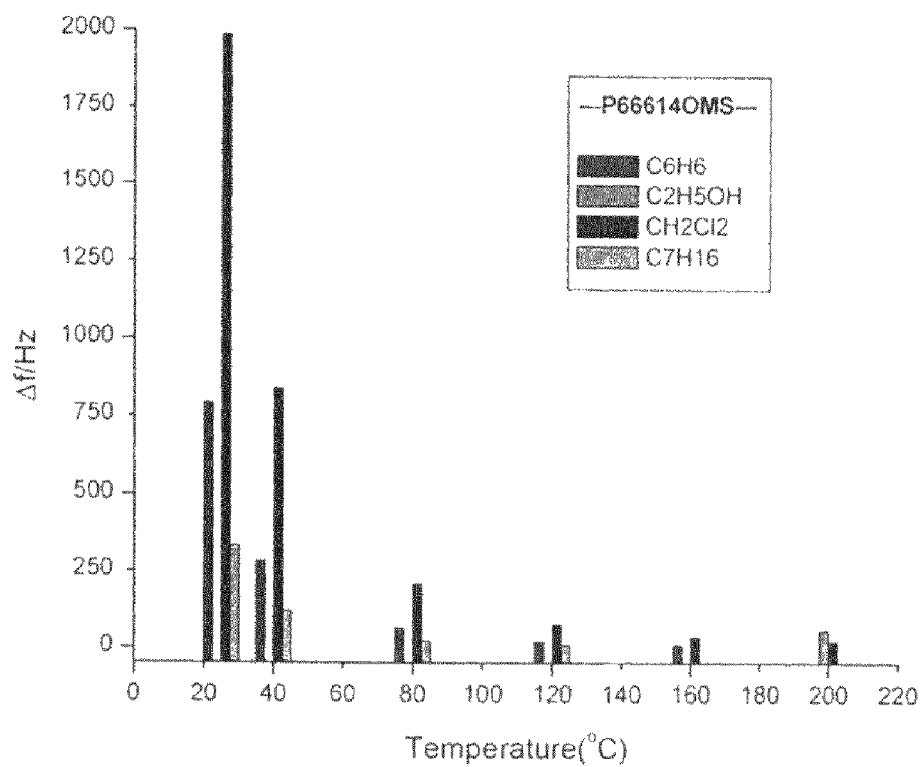
FIGS. 3A and B are graphs showing the frequency changes of the IL/QCM sensors exposed to 80% ethanol, heptane, benzene and dichloromethane at various temperatures.
Figure 3B:
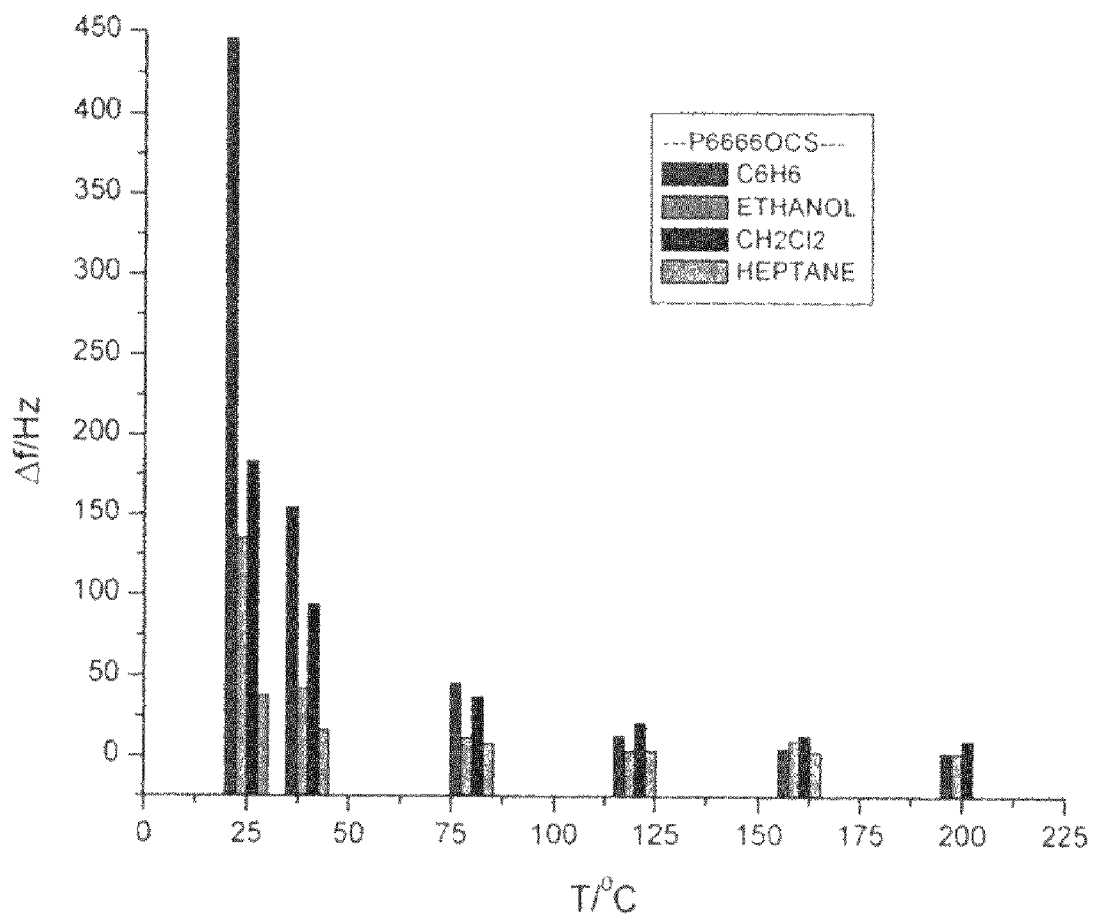
FIG. 3B shows Δf as a function of T of ionic liquid $P_{6666}$OCS.

FIG. 2 shows the linear relationship of the frequency changes and the concentrations of vapor were obtained over the 0% to 100% saturation vapor pressure range at 120° C. for all the organic vapors tested. The detection limit could reach as low as 5% (e.g. 7 mg/L for ethanol). When the system was cooled down to 24° C., the IL/QCM sensor gave reproducible response at 24° C. again indicating high stability and reversibility. This procedure has also been used to remove the volatile impurity in the ionic liquid coatings. IL sensors offer significant advantages over conventional metal oxide sensors for high temperature industrial sensing applications. FIGS. 3A and B show the temperature dependence of the sensors' response to various vapors with two different ILs. The sensitivity reduced with the increase of temperature. However, until 200° C., the sensors kept relative strong sensitivity.

Figure 5:
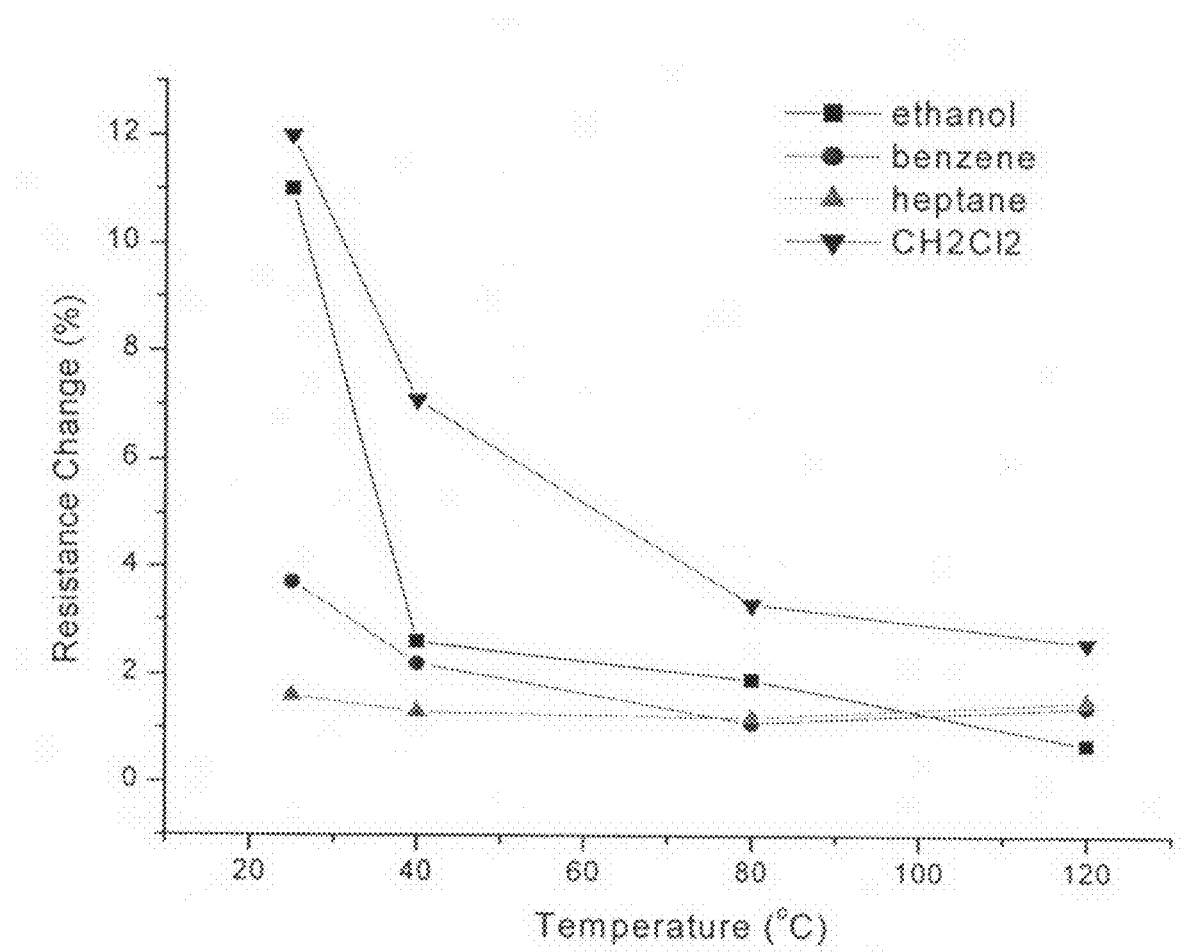
FIG. 5 is a graph showing ΔR % vs. temperature curve.

Early literature of ionic liquid gas sensors quantified the analyte concentration by viscosity induced frequency change (Wilkes, J. S., et al., J. Chem. Soc., Chem. Commun., 965 (1992); Bonhote, P., et al., Inorg. Chem. 35, 1168 (1996)). The sensor response is more complicated and can vary depends on experimental conditions. Mass detection by using Sauerbrey's equation (Ren, R. X., et al., WO 0294883 (2002); Ren, R. X., in Green Synthesis of Ionic Liquids for Green Chemistry, Chapter 6 in the American Chemical Society Symposium Series #865 Ionic Liquids as Green Solvents: Progress and Prospects, American Chemical Society: Washington, D.C., pp. 70-81 (2003)) (i.e. $\Delta f = -2\Delta mnf_0^2/(A(\mu_q \rho_q)^{1/2})$, where n is the overtone number, μq is the shear modulus of the quartz ($2.947 \times 10^{11}$ g/(cm sec$^2$), and $\rho_q$ is the density of the quartz (2.648 g/cm$^3$)) assumes the foreign mass is strongly coupled to the resonator. This condition can be met when the device is operating in the gas or the vacuum phase, the added mass binds tightly to the surface. Thin, rigid IL film was made so that the Sauerbrey equation is valid. Thin IL film was characterized by AFM (FIGS. 4A and B). Its rigidity is characterized by simultaneously measuring the damping resistance and the frequency change during the vapor detection experiments using Maxtek RQC™. Table 1 summarizes the data of damping resistance (R) and its change (ΔR %; FIG. 5) for the four analytes tested at different temperatures. At room temperature, the ΔR % values are relatively large especially for ethanol (11%) and dichloromethane (12%), indicating a viscosity change of the film upon the adsorption of organic vapors. The ΔR % value decreases with increasing temperature. This is consistent with the thermodynamics i.e. the partition coefficient of gas molecules in liquid film reduces with increasing temperature. At 120° C., the ΔR % was less than 2.6% for the four samples tested. This means that the change of viscosity caused by the gas adsorption on the IL film is very small at high temperature. The frequency changes were contributed mainly from the mass loading in the IL film and the Sauerbrey Equation relating frequency change to pure mass loading is valid. This enables qualification of the thermodynamic and kinetic parameters of the interaction of IL film with volatile organic molecules by QCM technique. Table 2 shows the Henry's constants of various vapors in ILs obtained from our experimental results. Ethanol, benzene and heptane have similar vapor pressure but heptane has higher Henry constant. This result indicates that some organic vapors interact strongly with the cations of ILs; while others interact strongly with the anions of ILs. Therefore, by orientating of the immobilized ILs with either cationic terminal or anionic terminal could lead to selective response of IL film to various compounds.

sity of ethanol peaks depends on the thickness of the film and on the concentration of the ethanol vapor in gas phase. ATR-FT-IR alone or by combination with other techniques can be invaluable to obtain information of IL orientation, kinetics, concentration of the vapor and the physicochemical interactions of ILs with the gas analytes to facilitate the configuration of IL on surface.

Figure 7:
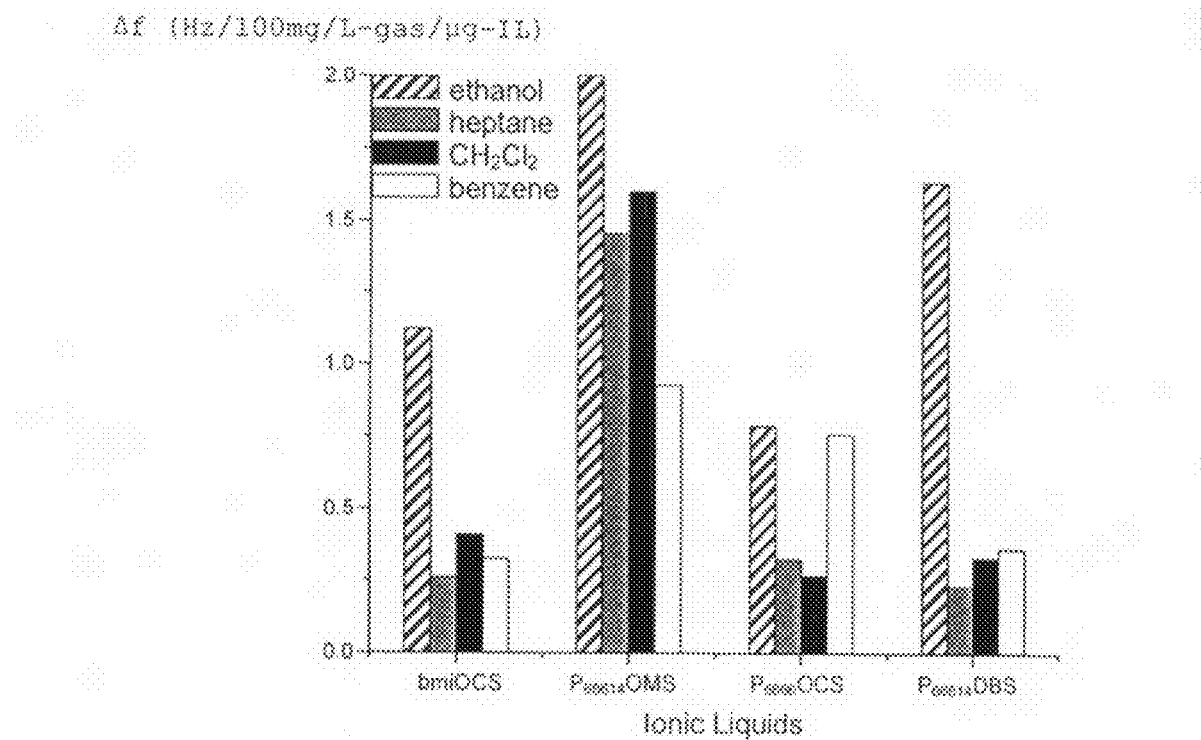
FIG. 7 is a graph showing normalized relative response pattern of IL sensors (coated with bmiOCS, $P_{66614}$ DBS, $P_{66614}$OMS, and $P_{66614}$OCS) for ethanol, heptane, $CH_2Cl_2$, and benzene at 120° C. The signals are normalized by the weight of IL coatings and the vapor pressure of each analyte.

FIG. 7 shows the different patterns when four different coating materials (three ionic liquids and a polyaniline) respond with ethanol, benzene, heptane and dichloromethane vapors by QCM. The preliminary results illustrate the feasibility of IL high temperature gas sensing and sensor arrays. Using various ionic liquids that were successfully prepared during the past four years (FIG. 1) along with those commercial available, the characteristics and techniques for preparation of thin (0.5-50 μm) or ultra thin (5-100 nm) IL films with

TABLE 1

Value of damping resistances and their changes during experiments.

| | Temperature | | | | | | | |
|---|---|---|---|---|---|---|---|---|
| | 24° C. | | 40° C. | | 80° C. | | 120° C. | |
| | Resistance | | | | | | | |
| | R (Ω) | ΔR % | R (Ω) | ΔR % | R (Ω) | ΔR % | R (Ω) | ΔR % |
| Ethanol | 4.7 | ±11% | 3.9 | ±2.6% | 4.0 | ±1.9% | 4.4 | ±0.7 |
| Benzene | 3.3 | ±3.7% | 3.4 | ±2.2% | 3.4 | ±1.1% | 3.6 | ±1.4% |
| Heptane | 3.2 | ±1.6% | 3.1 | ±1.3% | 3.2 | ±1.2% | 3.4 | ±1.5% |
| Dichloromethane | 3.5 | ±12% | 3.5 | ±7.1% | 3.6 | ±3.3% | 3.9 | ±2.6% |

TABLE 2

Henry constant (unit: Pa)

| | Ethanol | Benzene | $CH_2Cl_2$ | Heptane |
|---|---|---|---|---|
| beiOCS | 3.25E5 | 1.05E6 | 1.15E6 | 1.87E6 |
| bmiOCS | 5.57E5 | 2.03E6 | 1.55E6 | 2.58E6 |
| P6666OCS | 5.80E5 | 5.51E5 | 1.31E6 | 1.42E6 |
| P66614OMS | 3.85E4 | 4.33E5 | 2.25E5 | 0.31E6 |
| P66614DBS | 2.00E5 | 8.26E5 | 8.75E5 | 1.26E6 |
| P8888DBS | 7.23E5 | 1.25E6 | 9.71E5 | 1.88E6 |
| N7777DBS | 1.27E6 | 1.37E6 | NA | 2.50E6 |

Figure 6:
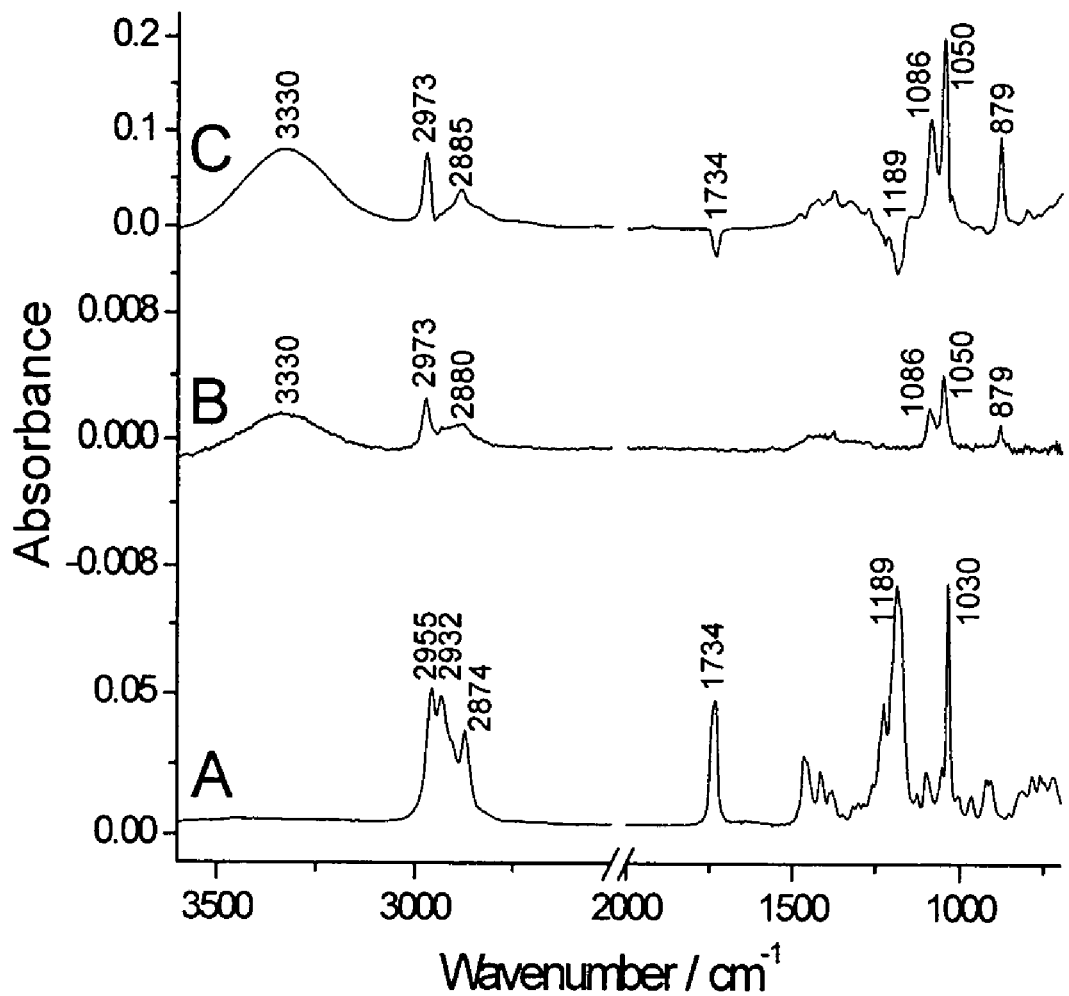
FIG. 6 illustrates three ATR-FTIR spectra, A, B and C, on a single plot. The graphs show the ATR-FTIR spectra of ionic liquid $P_{66614}$OCS film (Spectrum A), ethanol vapor exposed to bare substrate (Spectrum B) and to $P_{66614}$OCS film covered substrate (Spectrum C).

The key to a sensor array is to develop chemically selective interfaces which exhibit high level of chemical independence and structural order. Consequently, the information about which functional groups of an ionic liquid interacts with the organic volatiles is critical for the controlled configuration of IL on surface to generate IL films with a great diversity in structural and chemical properties. ATR FT-IR was used to characterize the gas/IL interaction to guide the surface design of IL selective interfaces. FIG. 6, spectrum A, is the absorbance spectrum of $P_{6666}OCS$ thin film. The peak at 1730 cm$^{-1}$ originates from the C=O (carbonyl) group. Peaks at 1187 cm$^{-1}$ and 1035 cm$^{-1}$ come from the O=S=O (sulfonyl) group. The other peaks come from the alkyl groups. FIG. 6, spectrum B, is the spectrum of ethanol when there is no IL film on the ATR crystal. When the IL film is exposed to ethanol, its absorbance spectrum is shown in FIG. 6, spectrum C. The negative peaks of C=O and O=S=O groups of $P_{6666}OCS$ indicate their interactions with ethanol vapor. Additionally, the intensity of the ethanol peaks were enhanced about fifty fold when interacting with only 10 μg/cm$^2$ IL film. This preliminary study shows that the intencontrolled properties were investigated. Their applications in gas sensing both at room and elevated temperatures were explored. Preliminary work shows that the interface function group of the IL film plays important roles for its interaction with gas phase volatile organics. In the present invention, we take advantage of the broadly defined self-assembly and nano fabrication techniques to prepare orientation-controlled IL or IL/template films to optimize the sensor performance. AFM, FT-IR, elliposometry and electrochemistry are used to study the modified IL film properties. The various combinations of electrochemical and surface techniques provide powerful ways to correlate structure and reactivity of surfaces and interfaces.

Below we have described phosphonium dodecylbenzenesulfonate (i.e. $P_{6,6,6,14}$ DBS) at a gold electrode as the model system to describe our experimental protocol. A similar protocol is applied to other ionic liquids (e.g. imidazolium ionic liquids). This leads to understanding the properties of the modified ionic liquid films on the gold surface. A series of chemically sensitive and selective ionic liquid interfaces can be designed whose responses to a range of vapors and gases are characterized, allowing selection of the best subset of materials for a particular application. Pattern recognition algorithms are developed (with collaboration of Dr. Harvey Qu). A portable QCM sensor array is developed (with collaboration with JADI, Inc.) for environmental monitoring for gas quality and automobile emission. The invention has substantial scientific and practical impacts in surface chemistry, material sciences and sensor technology.

Rigidity of the surface film is important for quantitative analysis by QCM technique. A thick film has a slow response time due to long diffusion pathway, but also its response is complicated by both the mass loading and the viscosity change of the film. A thin film allows fast adsorption equilibrium, short response time and accurate quantification by Sauerbrey equation. Consequently, the invention focuses on developing methods to make rigid IL thin film.

Most of the ILs are soluble in common volatile organic solvents, such as ethanol, acetone and dichloromethane. An IL thin film can be easily prepared from its solution by casting, spin coating or spray coating. The thickness of the film can be controlled by the solution concentration. When spin coating technique is used, the film thickness can also be controlled by the spin velocity. The thickness of an IL film coated by spray coating can be affected by several parameters of the spray gun aperture size and spray pressure. All of these three methods can provide a thin and uniform IL film but they cannot provide controlled molecular orientation. Furthermore, a small degree of "slippage" could occur at high temperature if the film is physically adsorbed on the gold substrate. Electrostatic, hydrophobic interactions, covalent attachment and polymer entrapment methods have been used extensively in the literature to immobilize organic or biological molecules with improved orientation. Covalently immobilizing ILs using their incorporated HS group or $Si(OR)_3$ group were also reported. However, this approach requires synthetic effort to modify each of the IL molecules and is labor intensive.

Owing to ionic liquid unique charge properties, we can immobilize ionic liquid on gold surface based on the electrostatic interactions of ionic liquid and a charged template. The properties of these immobilized films can be compared to those casting, spin coating or spray coating methods. The goal is to prepare a range of immobilized IL thin films with broad chemical diversity so that these interface materials respond sensitively and selectively to a variety of analytes. All developed IL thin films are characterized by an electrochemical technique, elliposometry and AFM, and then are investigated for their interaction with organic vapors by QCM, network impedance analyzer and ATR FT-IR.

The first approach is to take advantage the well established SAM technology. The beauty of SAMs is in their spontaneous association of molecules under equilibrium conditions that gives stable, structurally well-defined two-dimensional aggregates. The vast majority of alkanethiolate SAMs provide simple, reproducible, relatively well-ordered materials platforms with chemically diverse charged terminal groups. By varying the SAM terminal group, the interfacial functionality of the monolayer can be changed. Even though SAM can either have the function of performing some aspect of gas sensing in its own right, using it as a "primer" onto which the ionic liquid will be "grafted" should provide more complex bilayers with additional control over selectivity and sensitivity.

As shown in FIG. 8A, a SAM with carboxylic acid terminal groups and various chain lengths can be used as a surface modifier to change the physical and chemical nature of the Au substrate (for example, an electrode). The surface can then be treated with alkali solution and the carboxylic acid can be converted to carboxylate, rendering the surface negatively charged. Next, the surface can be immersed in an $P_{6,6,6,14}$ DBS solution. The interaction between the carboxylate group and the tetraalkylammonium or tetraalkylphosphonium cations can render some level of preferred orientation of the $P_{6,6,6,14}$ DBS modified electrode surface. The hydrophobic interaction among alkane chains in SAM and ILs should play additional roles for the IL/SAM composite.

Alternatively, as shown in FIG. 8B, the electrode surfaces will be made positively charged using a SAM with pyridine terminal groups, which can be treated with iodoalkane solution (Liang, C., et al., *Anal. Chem.* 74, 2172-2176 (2002)). The pyridine can react with the iodoalkane to produce pyridinium cations (Ohe, www.s-ohe.com). Afterwards, the surface can be immersed in a $P_{6,6,6,14}$ DBS solution. The ILs can be immobilized on the electrode surface via the interaction between the pyridinium groups and the organosulfonate anions.

Other SAMs with charged organic terminal groups, for example ammoniums, phosphate anions, or sulfonates, which can form anions or cations can be used. Ethanol can be used as a solvent for n-alkanethiols up to a chain length of about 18 methylene units (n=18). Above 18 methylenes, the compounds tend to precipitate. In this case hexane, dimethyl ether, or tetrahydrofuran can be used as solvents. For shorter chain thiols, which are water soluble, aqueous solutions will be used.

EXAMPLE 1

Gold beads were prepared by annealing in a methane/$O_2$ flame (Grate, J. W., et al., Sens. Actuators B 3, 85-111 (1991); and Finklea, H. O., in: Encyclopedia of Analytical Chemistry, Ed. R. A. Meyuers, Self-assembled monolayers on Electrodes, John Wiley & Sons, Chichester, 1-26 (1999)) to produce a smooth surface with predominant Au(111) facets. Freshly prepared gold beads were immersed in 1 mM $HS(CH_2)_{10}COOH$/THF solution for 3 days, followed by treatment with 0.1 M KOH solution for 15 min. Finally it was soaked in 5 mM IL ($P_{666,14}$ DBS)/EtOH solution for 2 days. After the above treatment, the gold bead was rinsed in EtOH for 24 hours. Characterization of the gold bead was carried out in 1 mM $Fe(CN)_6^{3-/4-}$ solution containing 0.1 M $NaClO_4$ by Cyclic Voltammetry (CV) and Electrochemical Impedance Spectrometry (EIS) at each step of modification.

Figure 9:
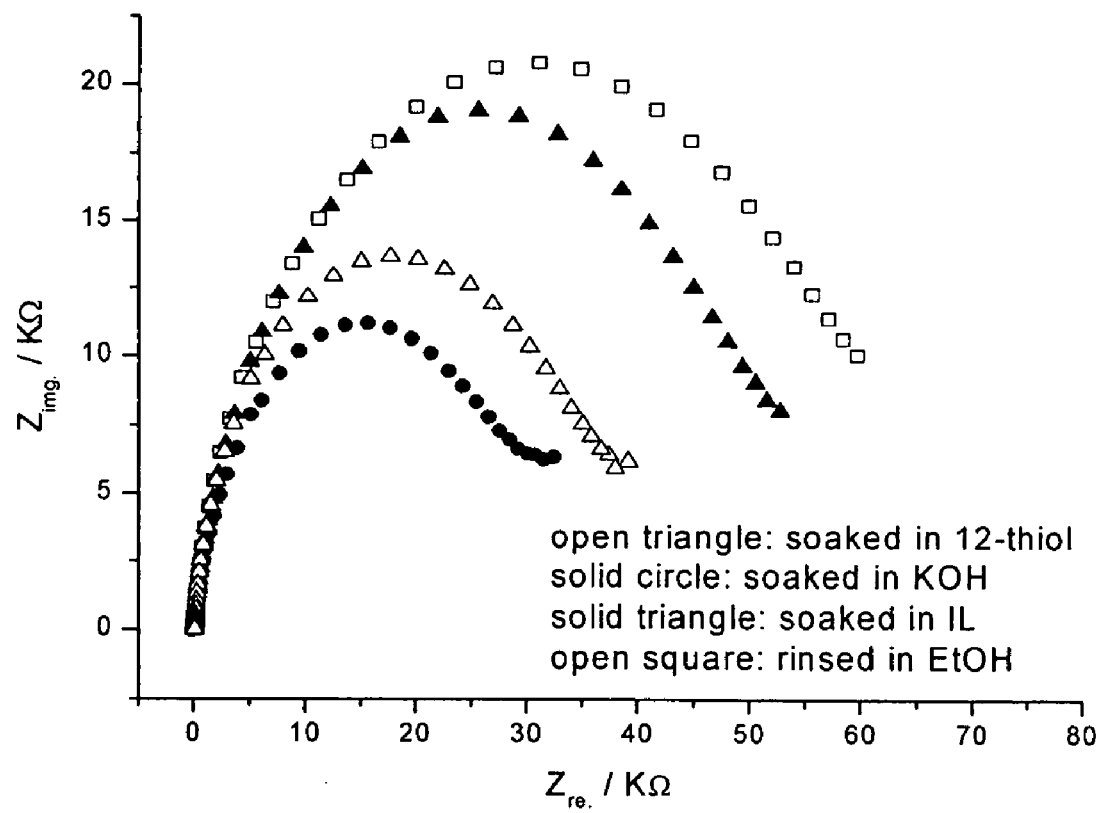
FIG. 9 is a graph showing Nyquist plots of EIS study of 1 mM $Fe(CN)_6^{3-/4-}$ in 0.1 M $NaClO_4$ on a gold electrode modified by soaking sequentially in: 1 mM $HS(CH_2)_{10}COOH$/THF solution for 3 days (open triangle), 0.1 M KOH for 15 min (solid circle), 5 mM IL $P_{66614}$ DBS/EtOH solution for 2 days (solid triangle) solutions and ethanol (open square). The gold electrode was prepared by annealing in a gas/$O_2$ flame, to produce a smooth surface with predominant Au(111) facets. Note: after each treatment, the gold electrode was rinsed in ethanol (EtOH) for 24 hours before EIS study was carried.

FIG. 9 shows that the charge transfer resistance ($R_{et}$) value increases after each step of modification. Immobilization of the ILs results in a more passive surface. After the thiol/IL modified electrodes were rinsed with THF, the $R_{et}$ increased further. This result confirms that a strongly immobilized IL layer was made; otherwise the $R_{et}$ value would have decreased if the solvent removed IL. The thiol/IL modified gold surface may be at its dynamic state when soaking in the solvents, allowing for further organization of the thin film.

Polymers (e.g. poly(dimethysiloxane) or rubbery polymers (Finklea, H. O., in: Electroanalytical chemistry Ed. A. J. Bard, I. Rubinstein, Electrochemistry of Organized monolayers of thiols and related molecules on electrodes, Marcel Dekker, New York, Vol. 19, 109-336 (1996)) are the favorite materials for gas sensing, however they often act as passive supports or structure materials to provide stability for sensing and tend to show very little specificity and are not useful as "stand alone" sensors (Nuzzo, R. G., et al., in Adsorption of bifunctional organic disulfides on gold surfaces, J. Am. Chem. Soc., 105, 4481-4483 (1983)). Conductive polymers and polyelectrolytes have mostly been studied for applications in microelectronics, photo electronics and energy storage. Conductive polymers are often regarded as polyions after they are doped. Their use as gas sensing materials are not well explored. Both polyelectrolyte and conductive polymer have charge which make them ideal materials as a template materials to make IL composite films. The fundamental idea has a much broader scope, and various pairs of conductive polymer/polyelectrolyte and IL composites can be imagined. The value and importance of the wide range electrodes modified by immobilization of a single species (conductive polymer or polyelectrolyte) is widely acknowledged and we believe that using appropriately chosen pairs of immobilized species can produce unique surfaces with valuable chemical properties (e.g. controlled porosity, orientation and tunable thickness).

Figures 10A, 10B:
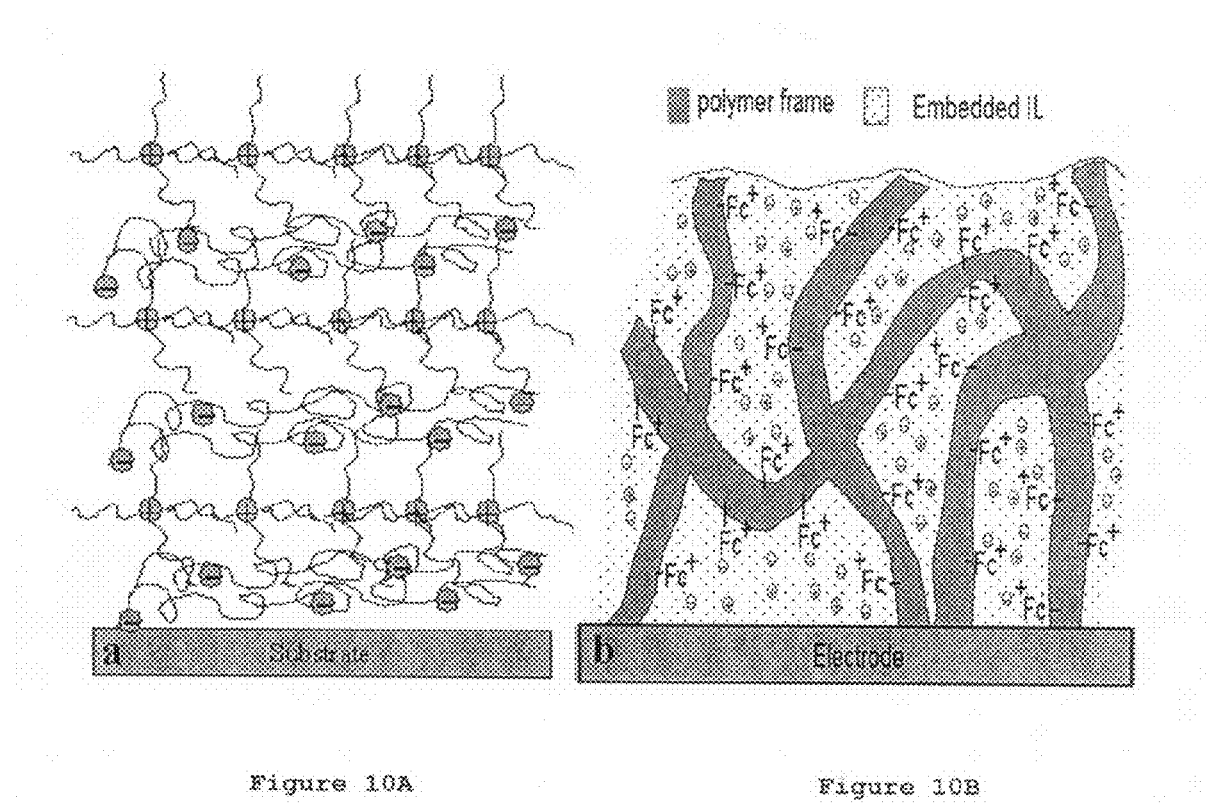
FIG. 10A illustrates layer-by-layer deposition of polysolfonate styrene having negative (−) charges, and ionic liquid having positive charges (+), on a substrate.
FIG. 10B illustrates an electrode having PVF with charged groups ($Fc^+$) as a polymer frame embedded with ionic liquid.

Polysulfonate styrene (polystyrene sulfonate, PSS) and poly(vinylferrocene) (PVF) can be used in the present invention, however other polyelectrolytes can be used to prepare the IL film on the surface. The layer-by layer deposition of polyelectrolytes (ie. ionomers such as polysulfonate styrene) and ionic liquids can be used (FIGS. 10A and B). Two methods can be used for PVF/IL film preparation. One is to deposit it on an electrode electrochemically from ionic liquid bathing electrolyte, the other is by mixing it with ionic liquids in certain organic solvents (e.g. $CH_2Cl_2$) and cast on the gold substrate.

Figure 11:
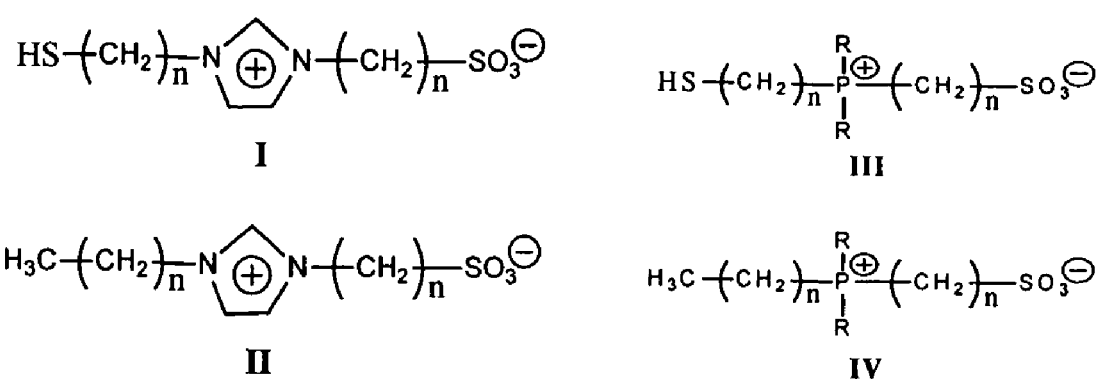
FIG. 11 shows chemical structures of thiolated zwitterionic liquids (I, III) and primary zwitterionic liquids (II, IV).
Figure 12A:
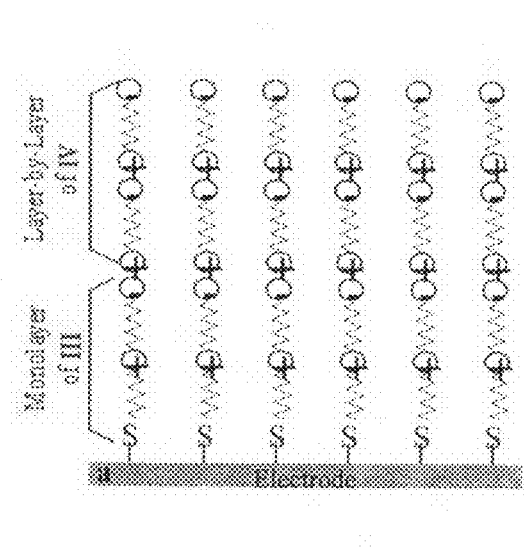
FIGS. 12A and 12B are schematics of the layer-by-layer deposited zwitterionic liquid film structure (FIG. 12A) and polyionic liquid film structure (FIG. 12B).
Figure 12B:
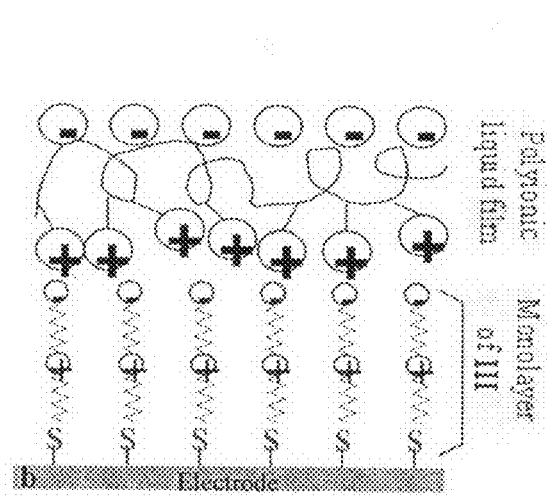

Recently, zwitterionic liquids or polyionic liquids (FIG. 11, compounds I and II), for example based on imidazolium sulfonate, have been synthesized (Nuzzo, R. G., et. al., J. Am. Chem. Soc., 109, 2358-2368 (1987)). In polyionic liquids, one of the ions is attached to a flexible polymer backbone as side groups or is incorporated into the polymer backbone. They are liquid macromolecules at temperatures lower than 100° C. (Christensen, P. A., et al., J. Electroanal. Chem., 318, 407 (1991)). Zwitterionic liquids or polyionic liquids surface assembly can provide additional control and rigidity than those discussed above. Zwitterionic liquids based on tetraalkylammonium or tetraalkylphosphonium, compounds III and IV can be synthesized. A layer-by-layer strategy of immobilization of the zwiterionic liquids can be developed for zwitterionic liquids (FIG. 12A) and polyionic liquids (FIG. 12B). The number of layers and the terminal layers effects on film properties can be considered.

The immobilized (bound) IL thin films can be used for their physical and chemical properties by means of electrochemical methods, QCM, AFM, Ellipsometry and Reflectance Absorption Infrared Spectroscopy (RF-FT-IR) to obtain structural, thickness, rigidity, orientation, stability, and surface coverage information of the immobilized IL thin films. QCM method can be used to study the thermal stability and solubility of the analyte in the IL films and to obtain thermodynamic (e.g. Henry's constant) and kinetic information (e.g. rate constants). Electrochemical methods can be used to develop the interface properties of ILs thin film, for example, the hydrophobicity/hydrophilicity of ILs film, the permeability of water, ions or redox species within the IL films and the ionic conductivity of the IL film. AFM and ellipsometry can be used to study the morphology change of the IL films before and after the exposure to organic vapors. RF-FTIR can be used to study the orientation of ILs and the interactions of IL film with vapor molecules. That information provides important guidance for ILs synthesis and surface immobilization strategies for IL sensor array, and provide invaluable fundamental understanding of the ILs and volatile organics interactions which are essential to the future industrial and laboratory applications.

High temperature gas sensing devices can be provided using IL thin films developed above via QCM transducers and perform a systematic evaluation for the long-term thermal stability of those IL surface assemblies. The target application is emission control and industrial application rather than the trace volatile analysis which is best done by GC-MS. Consequently, the sensitivity is not the limiting factor. But we can improve the sensitivity by controlling film thickness and using high frequency transducer or overtones. AT-cut quartz crystals that exhibit a high frequency stability ($\Delta f/f=10^8$) and almost zero temperature coefficient between 0° C. to 50° C. can be used. Above 50° C., the resonance frequency of QCM can depend on the temperature. If the temperature is very stable, the frequency response can reflect the mass loading and viscosity change on the IL/QCM. In order to ensure an accurate measurement, a dual QCM system (DQCM) can be used at high temperature conditions. The DQCM method includes a cell incorporating two quartz crystals. The reference sensor consists of a bare Au quartz crystal, and the other sensor consists of the IL immobilized Au quartz crystal. While interaction of gas analytes in the DQCM cell, the frequency difference between the reference and sensing crystals can be monitored. This design will improve sensitivity and detection limits.

Preliminary data shows a good linear relationship for IL sensor which suggests low viscosity changes of the IL films upon absorption of organic vapors. At an ideal condition, the frequency change is only caused by the mass loading on the surface. To evaluate mass loading effects experimentally, an equation was derived, from Sauerbrey Equation,[15] relating sensor responses to partition coefficients: $\Delta f_{v\ (mass)} = \Delta f_n\ C_v\ K/\rho$, where $\Delta f_{v(mass)}$, $\Delta f_n$, $C_v$, K and $\rho$ are, respectively, the frequency shift caused by the adsorption of the vapor, the coating thickness in KHz, the vapor concentration in the gas phase, the partition coefficient and the coating material's density. However, reports show that both the mass loading and the viscosity change of the IL film upon the absorption of vapors can cause the frequency change at room temperature. The change of the viscosity or modulus of the coating is reflected by the change of damping resistance fitted by the BVD circuit. At higher temperatures, the viscosity decreases significantly. For example, phosphonium based ionic liquids tend to have viscosities somewhat higher than their ammonium counterparts, especially at or near room temperature. However, on heating from ambient to typical industrial reaction temperatures (e.g. 70-100° C.) their viscosities generally decreased to <1 cPs (Aslanoglu, M., et al., Analyst, 123, 753-757 (1998)). Ionic liquid viscosities are also very sensitive to solutes, and the addition of reactants and or catalysts can be expected to further reduce viscosity. Consequently, the quantitative relationship between frequency change and analyte concentration can be evaluated based on several variables (temperature, viscosity, mass loading). Correlation of these relationships with data on the vapor pressure of ILs at high temperature will also be investigated. An advance technique with Network Impedance Analysis instruments and real-time data fitting software is used to measure both the frequency and the resistance real-time for above study.

The real time sensorgram can provide kinetic and thermodynamic information to reveal the interaction between gas molecules and ionic liquid coating. This information can be used to improve the performance of IL/gas sensors. Some variables need to be considered in the gas sensing kinetics. The most important one is the partial pressure of the gas to be detected. The partial pressure also determines the maximum response or the equilibrium response if the contact time is long enough. Another important variable is the flow rate. Primary results show that the response time not only depends on the nature of the gas and the ILs, but also depends on the flow rate. Theoretically, if the response is rate-limited by the diffusion of gas molecules in gas and liquid phase, increase the flow rate can reduce the thickness of the diffusion layer and thereafter reduce the response time. In addition, the flow rate also generates an extra pressure called dynamic pressure. According to Bernoulli's equation, the total pressure is the sum of static pressure and dynamic pressure.

Bernoulli's equation is:

$$P_t = P_s + \frac{1}{2}\rho v^2,$$

where $P_t$ is the total pressure that determines the association rate and equilibrium amount; $P_s$ is the partial pressure in static gas; $\rho$ is the density of gas and v is the velocity of the gas in meter per second (m/s). The higher flow rate not only speeds up association rate but also increase the equilibrium amount of gas in IL. However, the time to reach equilibrium does not necessarily decrease. Increased amount of gas that can be associated with IL can require more time to reach the equilibrium although the association rate is fast now. An effective kinetic model can be developed to take these important variables into account.

Figure 13:
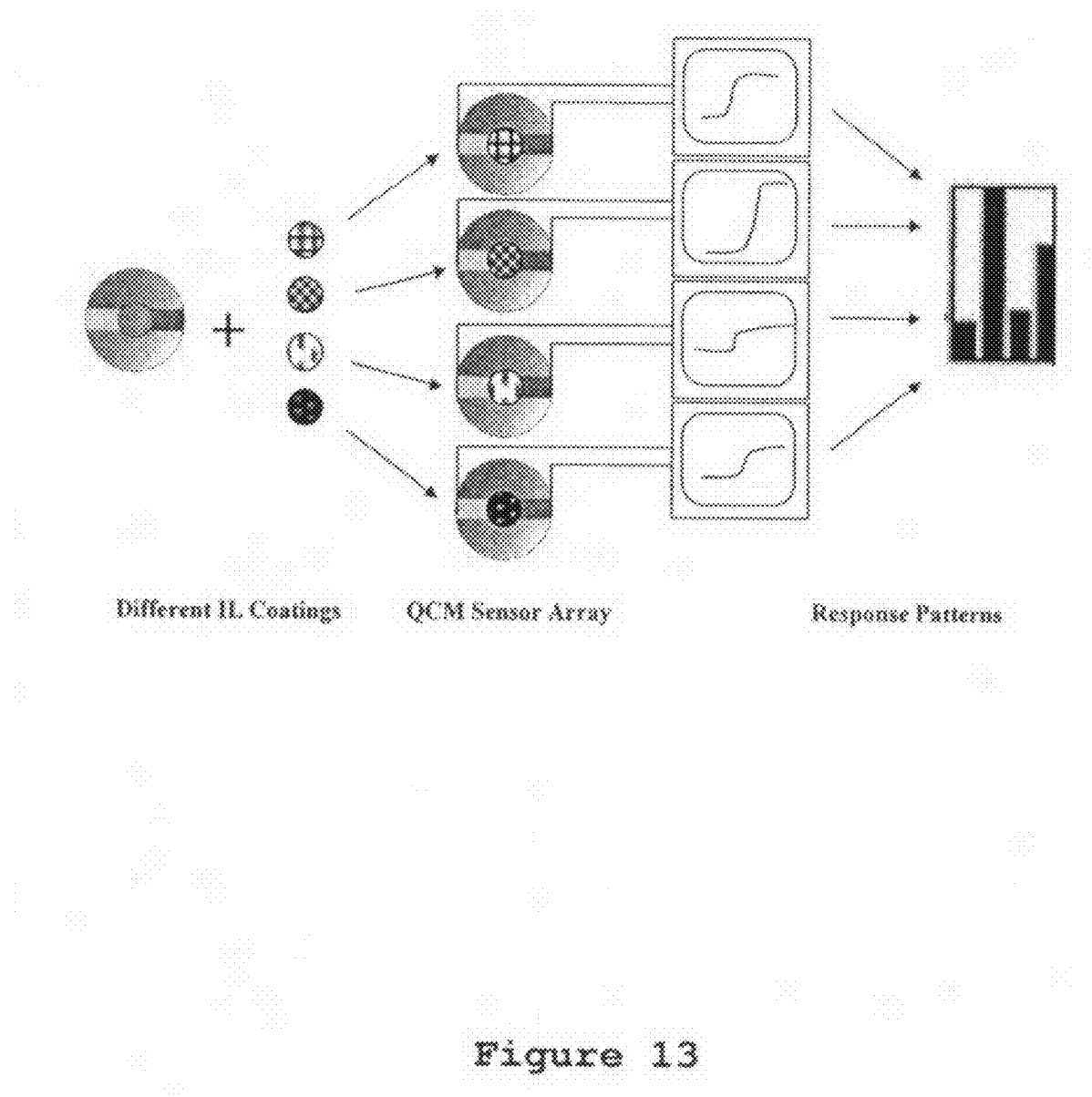
FIG. 13 is a drawing showing a schematic of a sensor array of QCM devices having different ionic liquid (IL) coatings and response pattern reorganization.

The chemical selective ionic liquid films developed can be used to design a QCM sensor array. The chemical selectivity of ILs to volatile organics depends on the interactions of ILs with volatile analyte. Therefore, varying the structure, and hence the properties, of the ILs can enhance the selectivity of the ILs/QCM sensors. For example, increasing the length of the alkyl chain in the cations can increase the sensitivity to olefins vapors; introduction of aromatic rings, such as naphthalene, anthanthrene or phenanthroline, can increase the sensitivity to fragrance vapors; ILs with inorganic anions, such as $BF_4^-$, $PF_6^-$, can have strong absorption to $O_2$ or $CO_2$ (ref); ILs with chloro- or floro-groups can have strong absorption to halogenated hydrocarbon. ILs offer many options for chemical modifications and hence a huge flexibility in tailoring molecular recognition sites by controlled organic synthesis and surface designs. Consequently, surface design and organic synthesis can be combined to modify the properties of each sensitive layer to develop sensors which can generate independent features with the same type of transducer. The signals of these sensors are recorded simultaneously. Due to their partly overlapping sensitivities, instead of a simple calibration function, multicomponent analysis or pattern recognition (Grate, J. W., et al., Faraday Discuss. 107, 259-283 (1997); Grate, J. W., et al., Anal. Chem. 70, 199-203 (1998); Ricco, A. J., Electrochem. Soc. Interface 3(4), 38-44 (1994)) can be developed to obtain the desired analytical information (FIG. 13). For the initial study, a simple gas mixture can be analyzed so to provide information about the limitation and potential of IL sensor arrays.

The vast chemical diversity of selected interfacial materials provides solid database for statistical pattern recognition. Differential interaction among the set of IL layers in the array produces response patterns that can be correlated with the identities, or at least the functional group classes, of the analyte vapors. Based on the response frequency and other characteristics (e.g. damping resistance) from sensor arrays, classification models can be established to identify different classes of compound through a series of supervised learning algorithms such as linear discriminant analysis, classification tree and neural networks etc. These models not only characterize the compound clusters numerically with low misclassification rates but also have good ability of predictability. Unknown volatile organic compounds and urban gas pollutants can be identified by statistical models to classes with same or similar chemical characteristics. Due to the uncertainty of the identification process, false positive and false negative rates can also be calculated through statistical modeling techniques. Sensory arrays with low misclassification rates have high reliability in practical applications. However, if the stand-alone IL sensor arrays run into difficulty meeting the performance requirements of many potential applications. The IL's can be combined with other techniques, such as gas chromatography (GC).

Figure 14:
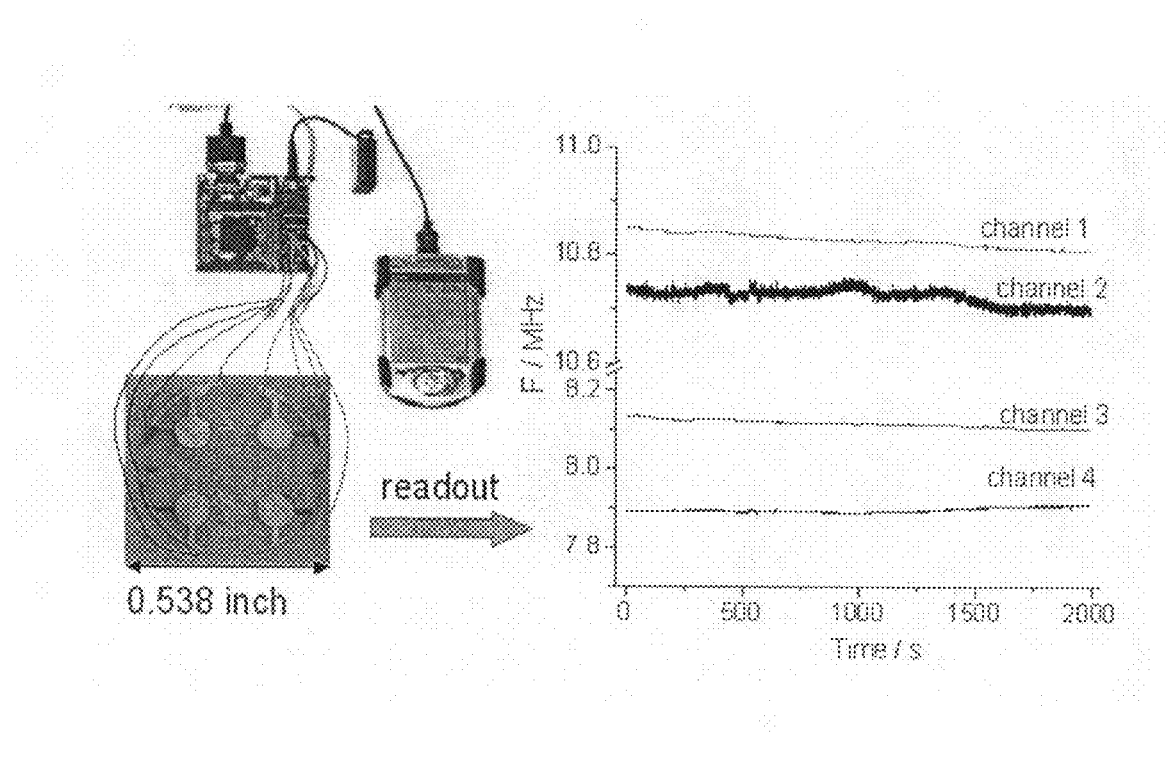
FIG. 14 illustrates a prototype QCM 4 channel device (left) with four QCM sensors in one monolithic quartz (lower left) in air to give a four channel output from the four. QCM sensors set up as an array.

The requirements of various sensors are based to a large extent on their respective applications, but the common stipulations are (1) sensitivity in the range of interest; (2) selectivity for the analyte; (3) broad dynamic range; (4) reversibility; (5) robustness and reliability; (6) lack of frequent calibration; (7) fast response; (8) inertness to sample matrix; (9) unattended operation, robot-compatibility, user friendliness; (10) small size; and (11) low cost (McQuade, D. T., et al., Chem. Rev., 100, 2537-2574 (2000)). The recently designed QCM transducer with state-of-the art high-speed Digital Signal Processing (DSP) hardware and wireless connectivity through UWB/RF (illustrated in FIG. 13) can be used to do field test for organic pollutants, and in FIG. 14 a graph of frequency vs time for four sensors in an array. The IL sensor arrays not only permit measurement of multiple analytes in the same small sample but also reduce the analysis time. With every element in the sensor array chosen to respond to a number of different chemicals or classes of chemicals but not necessarily individually highly selective toward any given analyte, so the difficulty of developing new materials with high chemical specificity for each analyte is reduced. Instead, the collection of sensors can contain as much chemical diversity as possible, so that the array responds to the largest possible cross-section of analytes (Tatumi, R., et al., Chem. Commun., 83-85 (2005); Yoshizawa, M., et al., Chem. Commun., 1828-1829 (2004); and Ohno, H., et al., Electrochimica Acta, 48, 2079-2083 (2003)).

EXAMPLE 2

This example shows ionic liquids immobilized on polyaniline scaffold for methane detection. Flammable gas sensors are essential in ambient air monitoring, occupational health and safety, biomedical diagnostics, industrial process control, and military and civilian counter-terrorism. Among various flammable gases, recent mine explosions showed that current methods for methane detection are not adequate. Methane is the major constituent of natural gas. The lower and upper explosive limits of methane in air are 5% and 15%, respectively. The warning percentage is often set to 0.5-1%. After carbon dioxide, methane is the second most important greenhouse gas that contributes to global warming. Methane is odorless. If inhaled, methane effectively replaces the oxygen in the body, causing suffocation and ultimately death will result. The detection of this potent gas is essential in the environmental, industrial and domestic worlds.

Although methane reacts drastically with chlorine or oxygen, it is in essence a fairly chemically inert gas. This low reactivity therefore makes it difficult to develop strategies that rely upon its chemical interactions for sensing. The physical adsorptions of methane on most solid-state materials are very weak. Since the chemical inertness of methane, commercially available methane sensors on the market so far are based upon either adsorption on semiconductors or optical methods. The most frequently used metal oxide is tin oxide ($SnO_2$). Its conductance or resistance changes upon adsorption of various gases. However, methane cannot be directly absorbed on $SnO_2$ and detected. The present of oxygen is a requirement for the successful detection. The oxygen chemisorbs onto the surface, thereby decreasing the concentration of electrons and increasing the electrical resistance. In the presence of methane, the gas detection mechanism involves the oxidation of methane with adsorbed oxygen to form $CO_2$ and $H_2$. This reaction consumes the oxygen on the surface, thereby increasing the conductance of the material. Due to the chemical inertness of methane, its oxidation has to take place at temperatures above 400° C. to obtain the required sensitivity. In addition, the dependency of the resistance of the metal oxides on the vapor concentration is not linear, which reduce the accuracy of quantitative analysis. Optical based methane sensors that have significant advantages in terms of sensitivity, owing to the very sensitive optical detectors, and of selectivity, as the absorption lines are usually a unique feature of the gas under detection. But they are often expensive and less-portable. Other detection methods are constantly explored, such as amperometric detection, biosensors, and piezoelectric sensors, but commercialization development has been slow.

Three things are needed to support a fire or explosion: a source of fuel (e.g. flammable gas or vapor), air (oxygen) and a source of ignition (e.g. spark, open flame, or high temperature surface). As a result, a sensor for flammable methane gases requires the sensing materials to be non-reactive, of low vapor pressure, have strong physical or chemical interactions with methane and functioning over a broad temperature range. As aforementioned, the chemical inertness of methane makes its absorption on most solid-state materials very weak. Room-temperature Ionic Liquids (ILs) represent a promising material for methane sensing. ILs have negligible vapor pressure at ambient pressure and possess high thermal stability in air. Typical IL decomposition temperature is 350+° C. Furthermore, literature reports show that flammable gases (i.e. $CH_4$, $C_2H_4$, $C_2H_6$, $CO_2$, $O_2$) have wide varying gas solubilities in ILs. For example, it has been reported that methane has a Henry's constant of 1690 bar in ionic liquid $bmiPF_6$ (1-n-butyl-3-methylimmidazolium hexaflorophosphate). The value is much lower than that of nitrogen, >20000 bar and oxygen, 8000 bar indicating a sufficient solubility of methane in $bmiPF_6$.

For all chemical sensors, sensitivity, selectivity, speed of response and reversibility are a consequence of the thermodynamics and kinetics of coating material/analyte interactions. In the past few years, the unique thermal stability of room temperature ionic liquids (ILs) were explored for their applications for high temperature gas sensing and gas chromatography stationary phase. Results from our lab demonstrated that ILs allows fast and reversible mass transfer for gas detection and IL sensor array in conjunction with the real-time, portable, low cost characters of QCM transducer can successfully classify volatile organic compounds at high temperature. The challenge in using ILs as sensing materials lie in their low sensitivity at high temperature since thermodynamics does not favor of gas analyte partition or adsorption on the liquid or solid interface at high temperatures. At high temperatures, when ILs were directly casted on the gold QCM surface, they may dewet from the surface and spread out from the center of gold if the adhesive intermolecular force is not strong enough. This can significantly affect the sensitivity and the reproducibility of the sensor. To achieve high sensitivity and reproducibility, it is essential that ILs can be coated as a smooth, thin and homogenous film that maintains its integrity without forming droplets or spread out when the measurement temperature is increased. Thin film further satisfy mass detection based on Sauerbrey's equation if a QCM transducer is used. The obvious approach to increase the sensitivity is to increase the amount of sensing materials coated. But increasing sensitivity via a thick IL film has several drawbacks such as non-rigid film with significant film viscosity change upon gas adsorption and a slow response time due to long diffusion pass way. An alternative approach is to use a stable, porous solid template that is readily wet by ILs to form IL thin films to achieve high sensitivity but at the same time maintain its thin rigid properties. Alumina nanopores were explored as such template for IL immobilization via QCM. When the nanopores were partially filled with ILs, the viscoelastic effect is absent and good quantitative analysis was achieved. Although the nanopores can hold more IL than a smooth surface, the detection limits were still very high. For two nonpolar examples, the values were 1875 $mg/m^3$ and 7634 $mg/m^3$ for cyclohexane and isooctane, respectively. The ideal template will be a porous solid scaffold that is stable, with large surface area and can be chemically modified or tuned to enhance the wetability of ILs. Owing to the unique charge properties of an IL, a solid template that has various charge states will be preferred so that its wetability can be increased through the electrostatic interactions between the ionic liquid and the charged template.

In this example, conductive polymer polyaniline (PAN) was selected as a template to immobilize ILs for methane detection via QCM transducers. PAN meets most if not all above requirements as an ideal support for IL immobilization. PAN is one of the most well studied conductive polymers. The properties of PAN film including conductivity, thickness, morphology, and oxidation states could be reproducibly controlled by varying the conditions of the polymerization both by chemical or electrochemical oxidation. PAN film possesses excellent stability in conductivity, structure and morphology at a large temperatures range from very low temperature to as high as 250° C. PAN has been explored successfully as a matix or sensing materials for gas sensor. The methods to electrochemically deposit a PAN film on gold with expect properties and morphologies were well established. Most importantly, PAN charge states can be easily controlled by varying the redox potential. Our results show that at its doped state, a positively charged PAN serves as a stable support for IL immobilization. Negatively charged IL anion interacts strongly with the PAN polymer via hydrogen bond. Significantly improvement of sensitivity ((0.1% methane in nitrogen), stability of methane sensors were observed when ILs were immobilized on PAN. Little PAN interaction with the methane analyte was observed indicating excellent wettability of ILs on PAN surface with no complication for the sensing mechanism. Our study fully revealed the advantageous of IL as sensing material through immobilization on PAN templates.

Experimental.

Chemicals: Butylmethylimidazolium camphorsulfonate (BMICS), butylmethylimidazolium methylsulfonate (BMIMS), tetrahexylphosphonium camphorsulfonate (P6666CS), trihexyltetradecylphosphonium methylsulfonate (P66614MS) ILs are synthesized by Dr. Rex Ren, IL-TECH Inc. (Middletown, Conn.) with over 98% purity. Ultra high purity methane (99.99%) in compress cylinder from (AGA Gas Inc., Canton, Mich.) was used as source of methane. Aniline (Merck) is purified by distillation under $N_2$ atmosphere and used immediately after distillation. All other chemicals are analytical grade, and 18 MΩ Millipore purified water is used for all the aqueous solutions.

Preparation of PAN film with IL PAN films were deposited on both sides of the QCM electrodes with an EG&G 273 potentiostat from 0.1 M aniline solution containing 1.0 M $HClO_4$ by controlling the electrode potential at 1.0 V vs SCE for 500 s or dynamically scan the electrode potential between −0.3 V to 1.0V vs SCE for 30 cycles at a scan rate of 100 mV/s. The counter electrode is Pt wire. The electrolyte solution is purged with $N_2$ for thirty minutes prior to experiments. After the polymerization, the PAN film was characterized in a 1.0 M HClO$_4$ solution by cyclic voltammetry. The final potential is set to −0.3 V, 0.35 V and 1.0 V to control the oxidation state of the result PAN film. At −0.3 V, 0.35 V and 1.0 V, the PAN film is at its reduction, partially oxidation, and oxidation states, respectively. The PAN/IL composites are prepared by soaking the PAN film in IL solutions in ethanol with various concentrations overnight. After the soaking, the PAN film is dried in N$_2$ atmosphere without further rinse.

Figure 15:
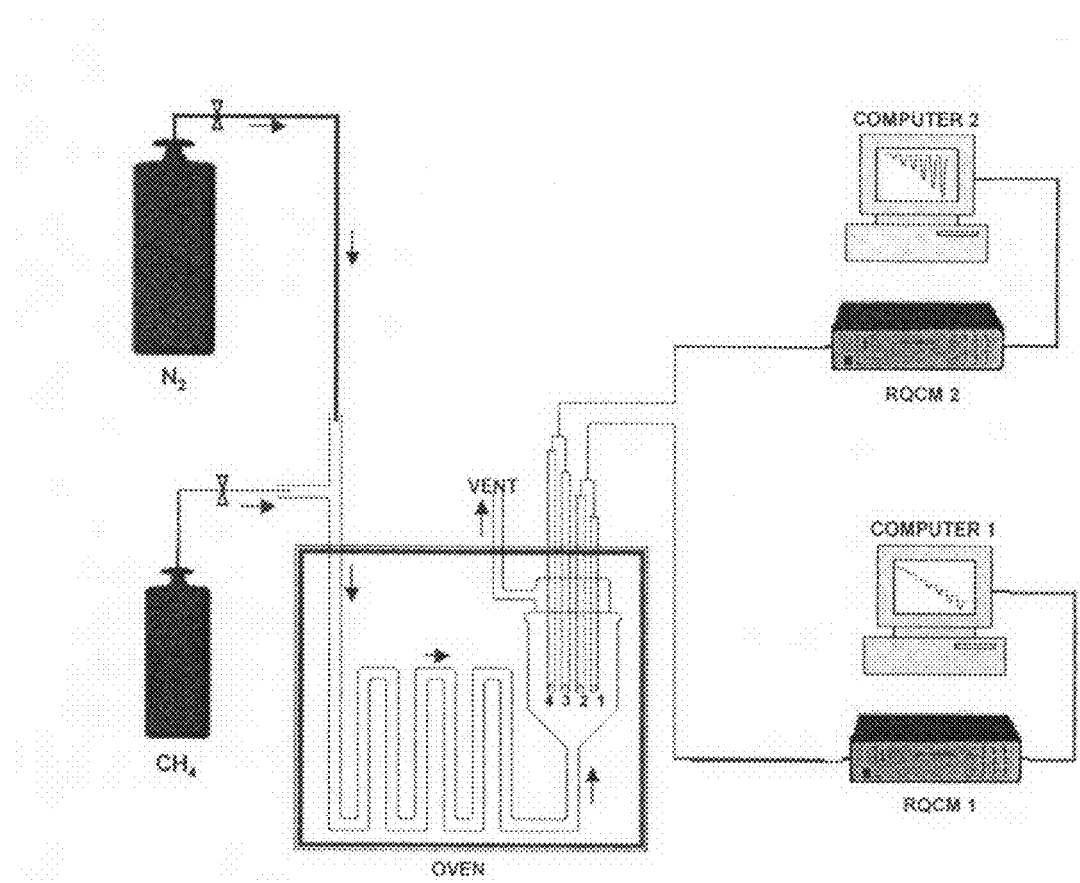
FIG. 15 shows the flow system setup for characterization of the PAN/IL sensors.

Flow system setup and characterization of the PAN/IL sensors: The flow rate of methane and the N$_2$ carrier gas was controlled by digital mass-flow controllers (MKS Instruments Inc.). A total gas flow rate of 200 ml/min was used. The methane flow was diluted by a N$_2$ flow and the final concentration was calculated based on ideal gas laws. The diluted sample gas flowed through tubing, ca. 1 m length, into the sensor chamber. As illustrated in FIG. 15, the tubing and the sensor chamber were located in a GC oven ("oven"), where the temperature was precisely controlled. The long pathway ensured homogeneous mixing of the sample vapor and the carrier gas. All the QCM used are AT-cut 10 MHz (International Instruments Inc., OK). A Mextec® RQCM ("RQCM") instrument was used to measure the resonant frequency and the damping resistance.

FTIR and UV-vis.

Results and Discussion.

IL selections: The criteria for IL selections is to avoid the covalent interaction of ILs with PAN substrate but maximum the Van Der Waal interactions, such as electrostatic and hydrogen bonding interactions between PAN and ILs so that the properties and advantageous of ILs as sensing materials will not compromised upon immobilization on PAN. Four identical PAN films are immersed in four 0.1 M IL solutions. The ILs are bmiCS, bmiOMS, P666140MS, and P6666CS. The PAN–IL films were studied for their response to methane via QCM and results are in Table 6.

TABLE 6

Frequency change after soaked in IL solutions (0.1 M).

| | IL | | | |
|---|---|---|---|---|
| | bmiCS | bmiMS | P$_{66614}$OMS | P$_{6666}$CS |
| Δf (KHz) | 36 | 37 | 22 | 33 |

Figure 16:
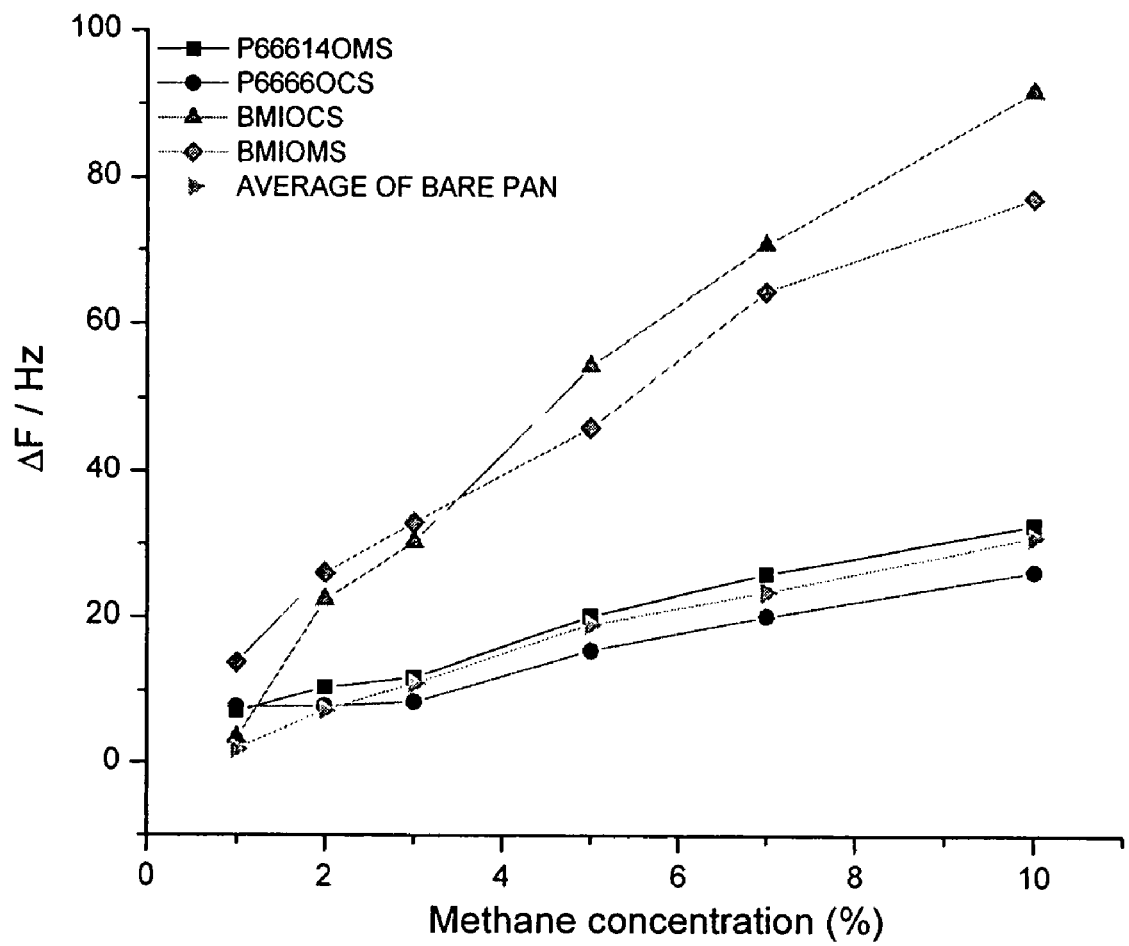
FIG. 16 shows isotherms from different ILs.

Since the PAN film is identical, the total amounts of ILs immobilized on the PAN films should be at the similar order of magnitude. However, the methane sensing signals from PAN/bmiCS and PAN/bmiMS films are much stronger than that from the other two films, see FIG. 16. FIG. 16 shows the isotherms from different ILs. This can be explained by the wetability of PAN. BmiCS and bmiMS are hydrophilic; therefore, they could easily form a very thin film on the interface of a porous PAN film. However, phosphonium based ILs are hydrophobic, they may aggregated to make tiny drops within the PAN film.

Figure 17A:
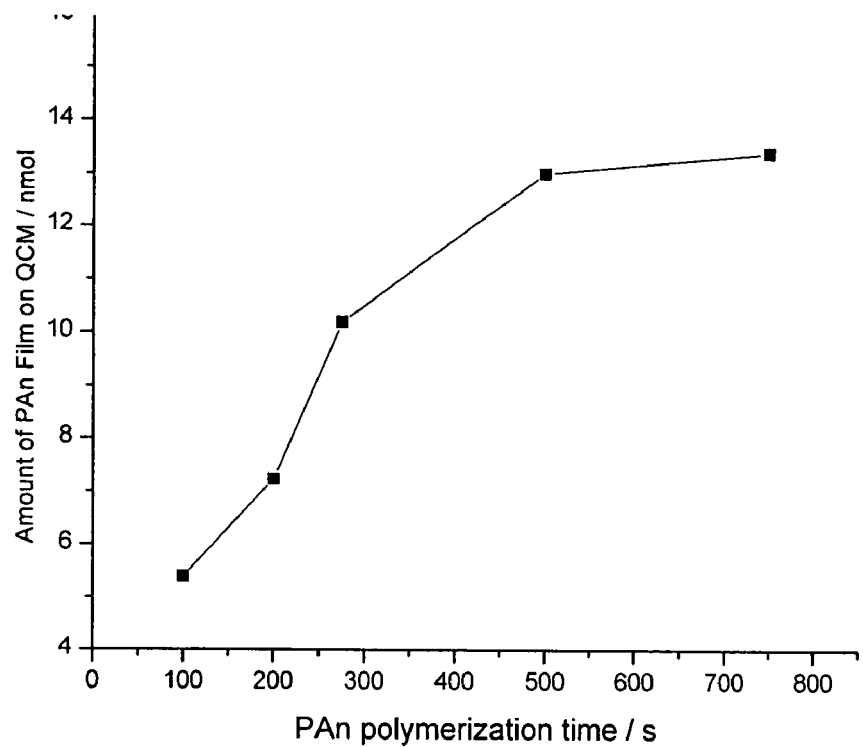
FIG. 17A shows the amount of PAN deposited vs. polymerization time.
Figure 17B:
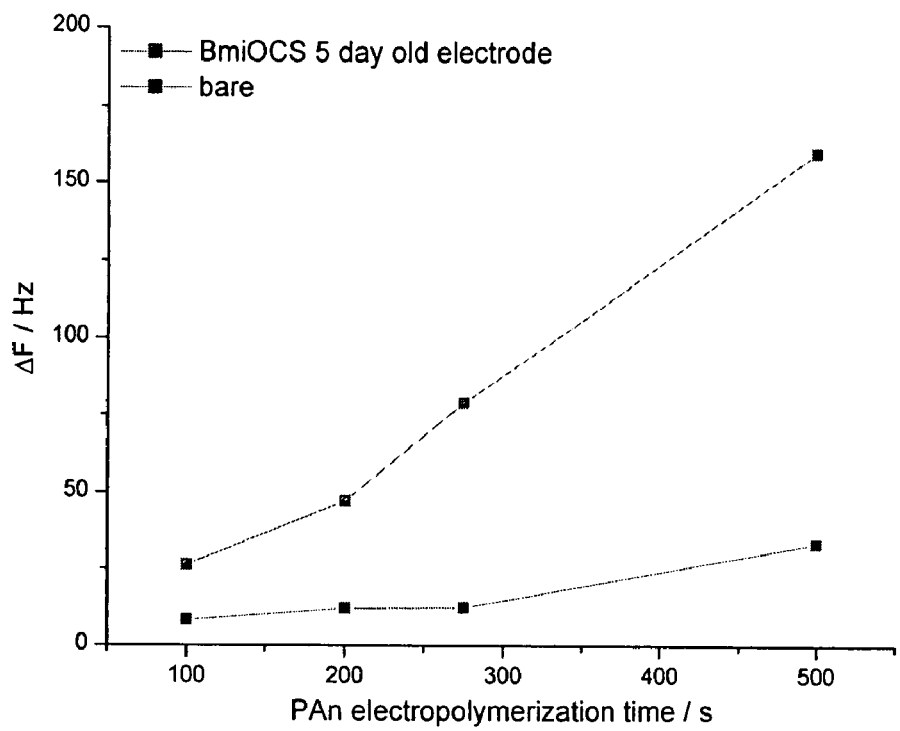
FIG. 17B shows Δf vs. polymerization time.

PAN template thickness effect: PAN film thickness was controlled by varying the time of electrochemcial polymerization at 1.0 V. The resulting films were characterized by Cyclic Voltammetry and the amount of PAN deposited on the electrode was calculated from the CV results using Farady's Law. Assuming the PAN film is homogeneous, the film thickness will be proportional to the amount of PAN at a constant electrode area. FIG. 17 shows the amount of PAN deposited vs. polymerization time (FIG. 17A) and Δf vs. polymerization time (FIG. 17B). All Films soaked in 0.2 M bmiCS solution and tested at methane concentration of 10%. Shown in FIG. 17, the amount of methane adsorbed increased with increasing film thickness for both bare PAN and IL–PAN film but the amount of increase is much more significantly in the PAN–IL film than that of the bare PAN film. This result shows that the PAN template has very low diffusion barrier for IL molecules and the IL is not only immobilized on the surface of the PAN film, but also can diffuse into the PAN film to make a composite. As a result, methane molecules can absorbed not only on the surface but also into the PAN or PAN/IL film.

Figure 18:
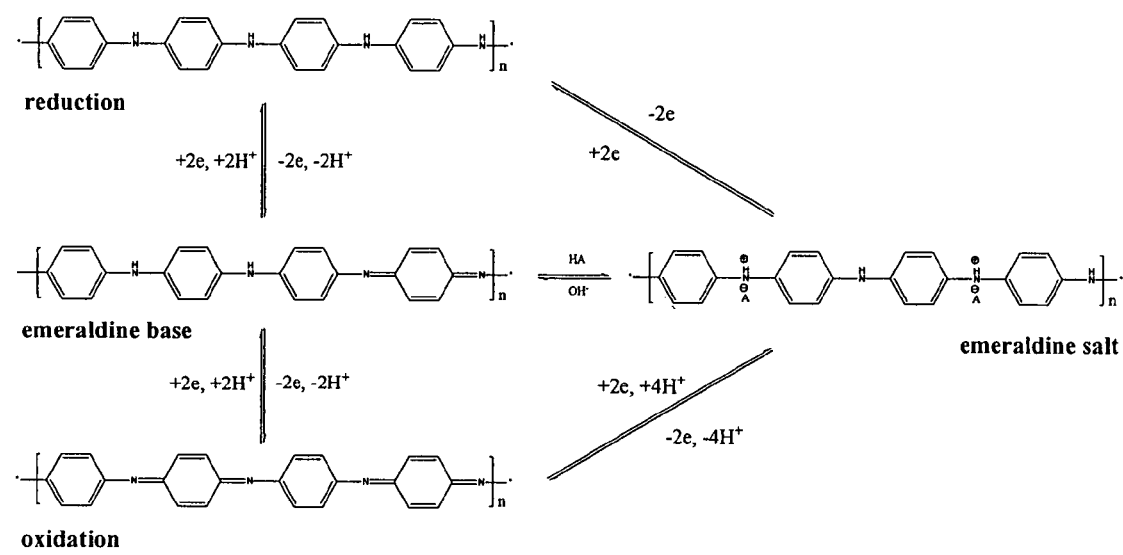
FIG. 18 shows the structures of PAN.
Figure 19:
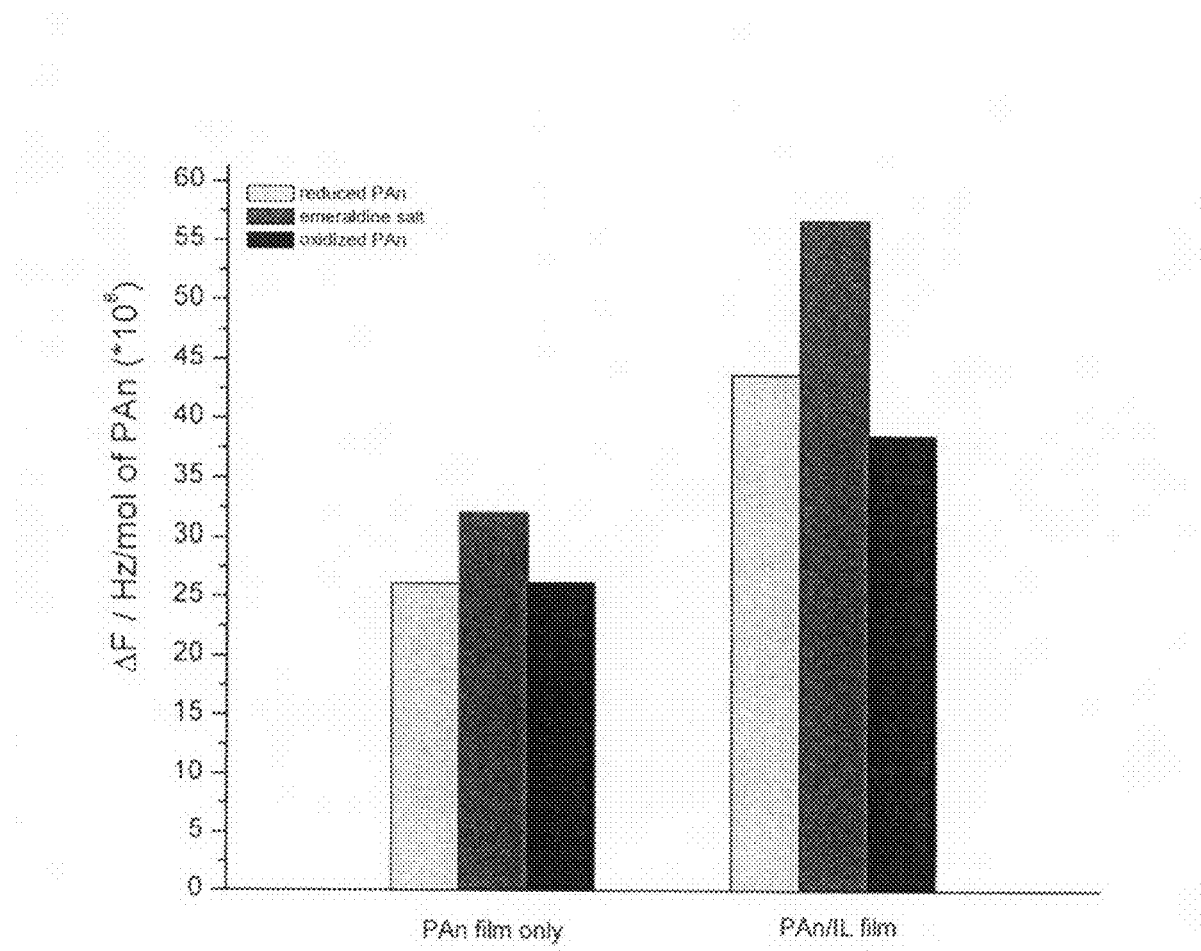
FIG. 19 shows the methane sensing results of the PAN films at different oxidation states before and after the immobilization of IL.

PAN oxidation state effect for IL immobilization: FIG. 18 shows the structures of PAN. As shown in FIG. 18, there are essentially four different redox state of PAN: reduction state, emeraldine base, emeraldine salt, and oxidation state. Oxidation state of PAN will not affect the morphology of the PAN film but it will have different charge. FIG. 19 shows the methane sensing results of the PAN films at different oxidation states before and after the immobilization of IL. Results show that immobilization of IL on the PAN increases the sensitivity of methane detection and the PAN at emeraldine state showed the largest sensitivity for methane. PAN at the emeradine salt state is a charged polymer, the other two states are not. This confirmed our hypothesis that ILs, comprised entirely by ion, will bond favorably with charged PAN and the electrostatic interaction between ILs and charged PAN can facilitate the evenly distribution of IL within a charged polymer resin. To our benefit, the Emeralsine salt and emeraldine base are also more stable than the reduced or oxidized PAN. Therefore, in our work, we used medium oxidized PAN.

Figure 20:
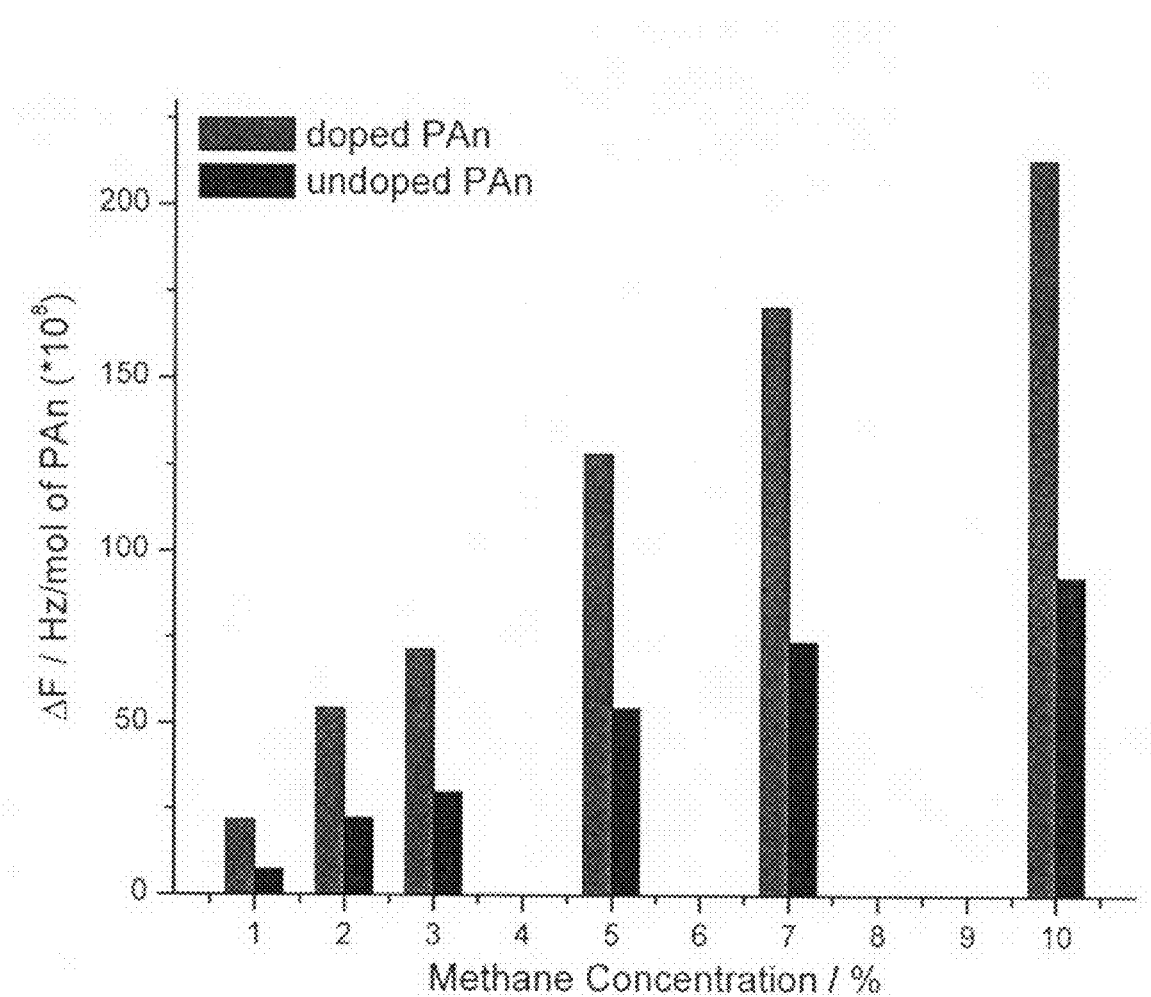
FIG. 20 shows the frequency change of same PAN film at different state: doped and undoped, 10% methane.

We further compared the sensitivity of methane adsorption on both PAN emeraldine salt and emeraldine base states, shown in FIG. 20. FIG. 20 shows the frequency change of same PAN film at different state: doped and undoped, 10% methane. The doped PAN/IL film showed larger sensitivity than the undoped PAN/IL film. This is consistent with our prediction that IL, containing cations and anions, is more efficient to absorb into the charged PAN film (i.e. doped PAN) and can spread evenly within the PAN film.

Figure 21A:
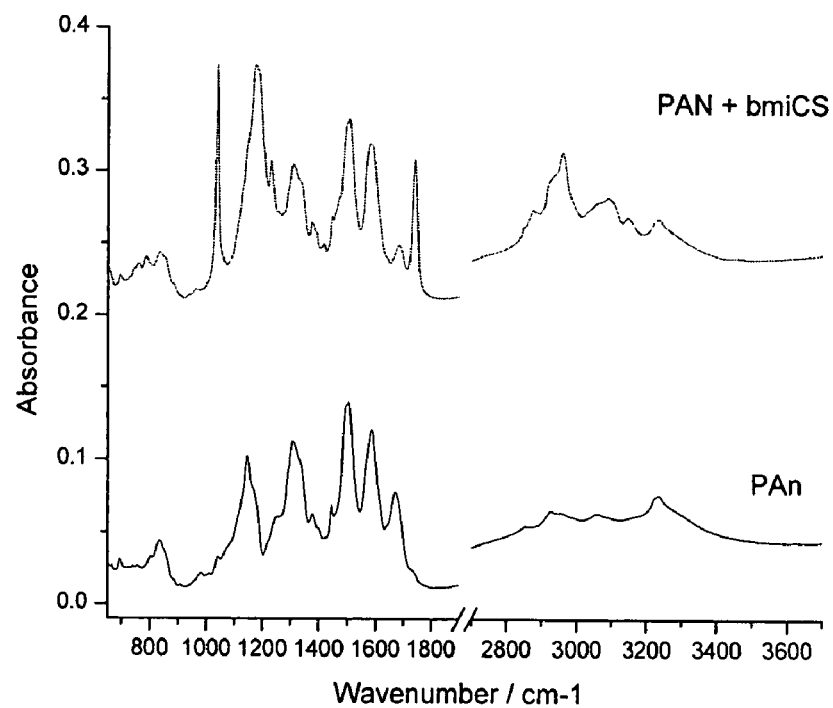
FIG. 21A shows FTIR of PAN and PAN+bmiCS.
Figure 21B:
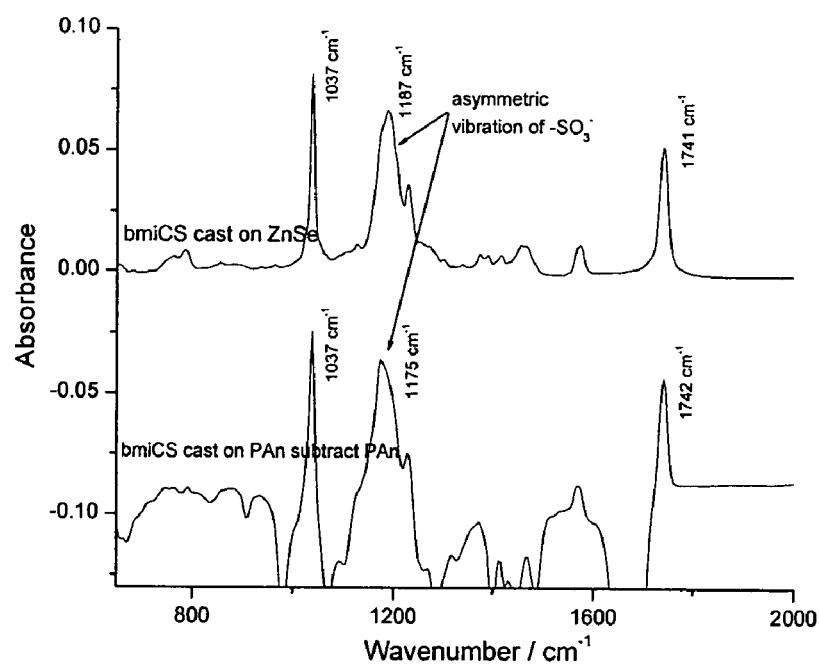
FIG. 21B shows FTIR of bmiCS and PAN+bmiCS subtract PAN.
Figure 22:
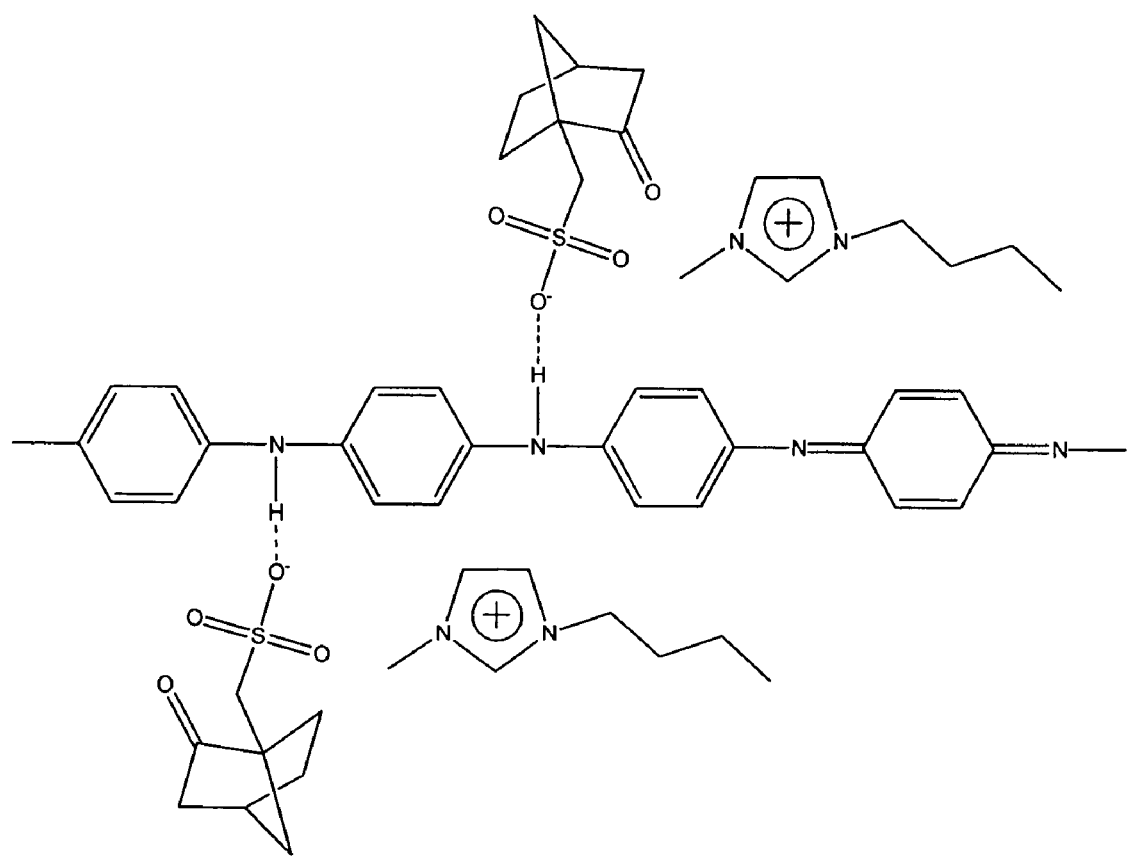
FIG. 22 shows scheme 2.

Characterization of PAN by FTIR and UV: The interaction of PAN and IL bmiCS was further characterized by ATR-FTIR and UV-Vis. A spectrum of undoped PAN cast film was first obtained by ATR method on a ZnSe crystal. All the typical peaks of undoped PAN are showed at 1592, 1495, 1305, 1163, and 833 cm−1, corresponding to the functional groups of PAN (ref). The PAN film was cast from its NMP solution and some of the NMP remained in the PAN film, so that there are peaks at 1688, and 2930 cm−1, which come from the vibration of NMP molecules. When a layer of bmiCS was coated on the PAN film, both the peaks of PAN and the peaks of IL were observed. Since the ATR-FRIT method can only obtain a spectrum of substance within a few microns from the surface of the ZnSe crystal, this result again suggests that the PAN porous structure is wetable by IL and it has little resistance for IL to penetrate through and reach to the surface of ZnSe. Interestingly, when bmiCS was cast on bare ZnSe crystal, the asymmetric vibration of —SO3— group of bmiCS gives a peak at 1187 cm−1. When bmiCS was cast on a PAN/coated ZnSe crystal, this peak shifted to 1175 cm−1. There is no other change in the spectra of bmiCS after interact with PAN. The peaks of PAN did not change. Previously, we have assigned this red shift of the asymmetric vibration of —SO$_3$— group to the formation of hydrogen bond. The hydrogen bond could exist between the —SO3— group and the amine group of PAN, see scheme 2. This is supported by the fact that the peaks of PAN did not change. The N—H vibration peak around 3300 cm−1 of PAN is very broad. The peak position change caused by the formation of the H-bond with —SO3— group is not very significant and hard to observe. FIG. 21A shows the FTIR of PAN and PAN+bmiCS; FIG. 21B shows the FTIR of bmiCS and PAN+bmiCS subtract PAN. FIG. 22 shows scheme 2.

Figure 23A:
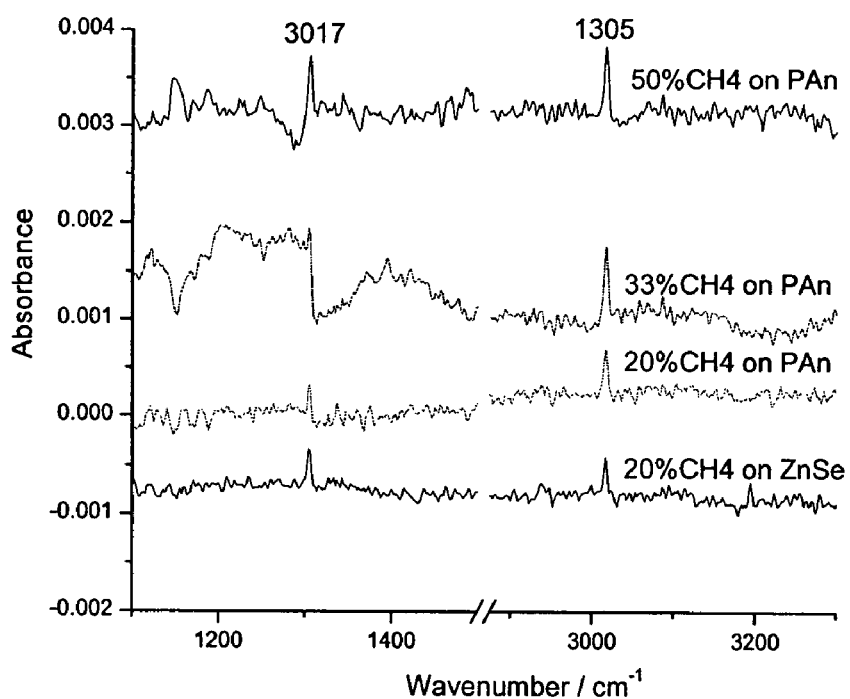
FIG. 23A shows the spectra of methane on ZeSe and on PAN.
Figure 23B:
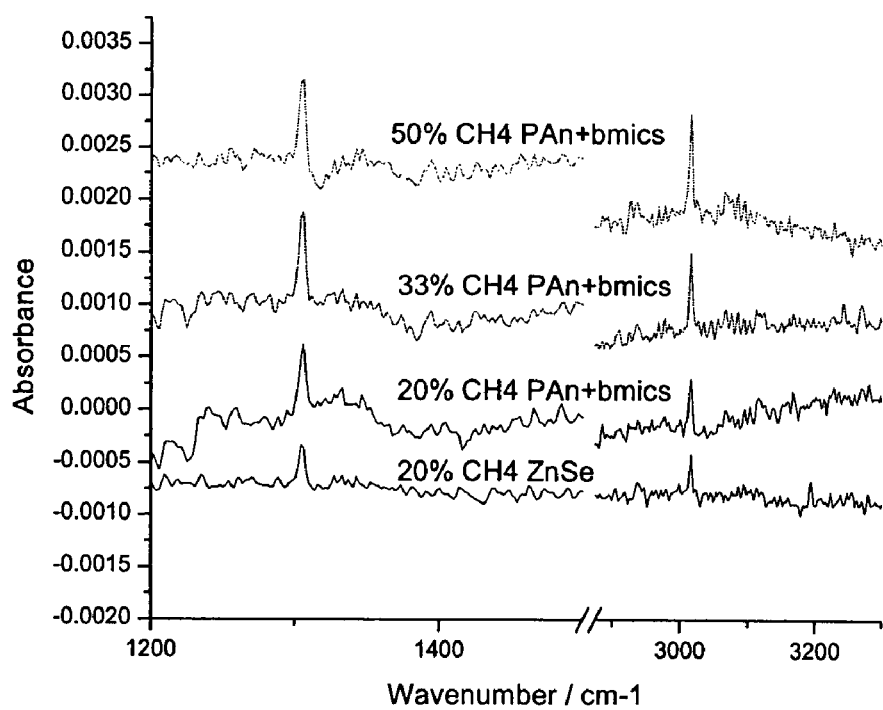
FIG. 23B shows the spectra of methane on ZnSe and on PAN+IL.

The spectroscopy of methane interactions with PAN and PAN–IL films were studied. FIG. 23A shows the spectra of methane on ZeSe and on PAN, FIG. 23B shows the spectra of methane on ZnSe and on PAN+IL. Shown in FIG. 23A, methane has two absorption peaks at 3017 and 1305 cm−1 on bare ZnSe crystal. When a PAN film was cast on ZnSe crystal, there is absorption of methane on PAN. The peak positions did not change. However, the intensities increased slightly by a factor of about 1.23, which is probably due to the porous morphology of PAN that has increased the surface area. Methane is also absorbed into the PAN/IL composite film, FIG. 23B. The peaks position did not changed too. However, if we compare the two lines at the bottom, when IL is applied, the intensity increased by a factor of about 1.5. The applying of IL will not increase the surface area of the film but changed the surface properties. Therefore, the absorption of methane has been enhanced when IL was cast on PAN film and hence a PAN/IL composite film formed. The difference of the two factors (1.23 and 1.5) is not significant because the ATR-FTIR method only record the vibration spectra within a few microns of the ZnSe surface. The overall difference upon methane absorption might be significant if we consider the whole PAN/IL film could be much thicker than microns.

In addition, we can also see that the intensity of the methane peaks increased with the increasing of methane concentration, FIG. 23, which allowed quantitative detection by our sensor. The spectra of methane do not change after adsorption in PAN film and PAN/IL film. Thus the interaction of methane and PAN/IL should be only Van de Waale's interactions. This guaranteed a fast and reversible detection of methane.

Figure 24:
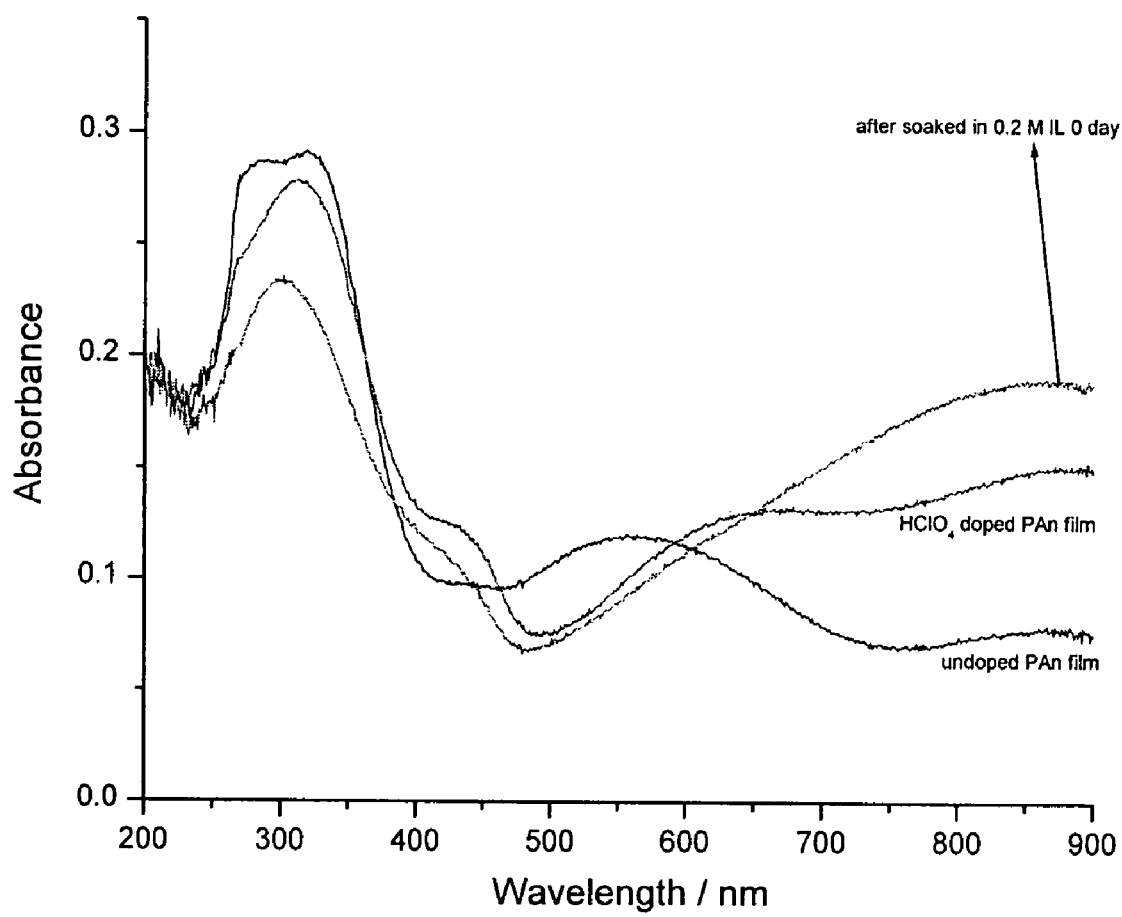
FIG. 24 shows the UV-Vis of PAN film soaked in IL solution.
Figure 25:
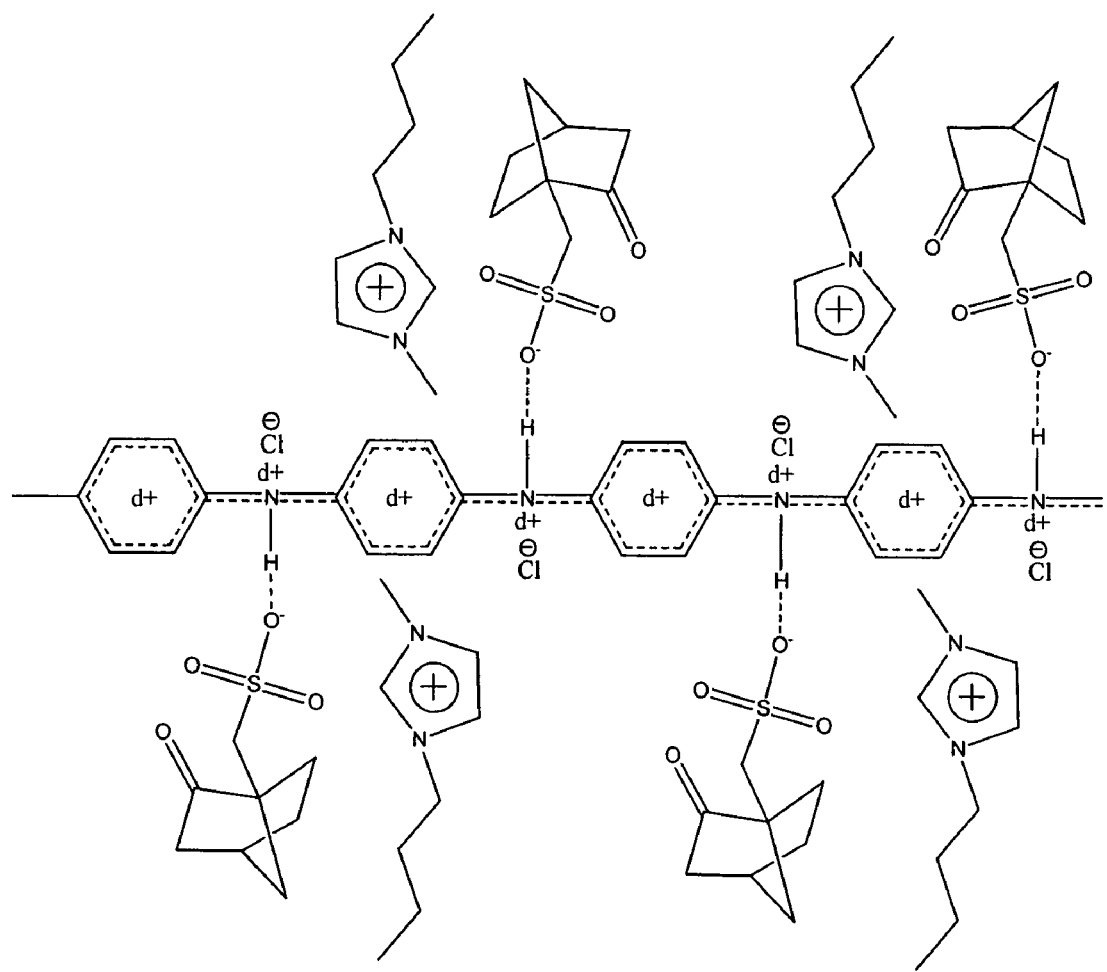
FIG. 25 shows scheme 3.

FIG. 24 shows the UV-Vis of PAN film soaked in IL solution. The UV-vis spectra of three different treated PAN films are shown in FIG. 24. PAN film was electrochemically deposited on an ITO electrode and then dedoped in $NH_4OH$ solution. The UV-vis spectra of dedoped PAN are very typical. There are absorption bands around 300 nm ($\pi_b$–$\pi_b^*$) and 550 nm ($\pi_b$–$\pi_q$). After doped with $HClO_4$ solution, the band around 300 nm became weaker; a shoulder around 415 nm (N–$\pi$) showed up, the band around 550 nm shifted to about 650 nm, and there is high profile absorption beyond 700 nm (long range conjugation). All these characters are come from the doped PAN. After soaking in 0.2 M IL solution, the band around 650 nm totally disappeared, and the absorption between 700 and 900 nm are even higher. These may indicate that the doped PAN interacts with IL and enhance the long-term conjugation of PAN backbone. As we have proposed the formation of H-bond by the FTIR results, this interaction of doped PAN and IL might be described by Scheme 3, as shown in FIG. 25. These FTIR and UV results suggest that there are molecular interactions between IL and PAN which increase the wetability of IL on the PAN film. In each repeat units of PAN, there are two —NH— groups when PAN is dedoped. While there are four —NH+— groups when PAN is doped. Therefore, doped PAN has larger capacity to form H-bond with IL. This may explain why doped PAN has better sensitivity than dedoped PAN when both of them were used to immobilized IL and detect methane.

Sensitivity vs. Amount of IL Loaded.

Figure 26:
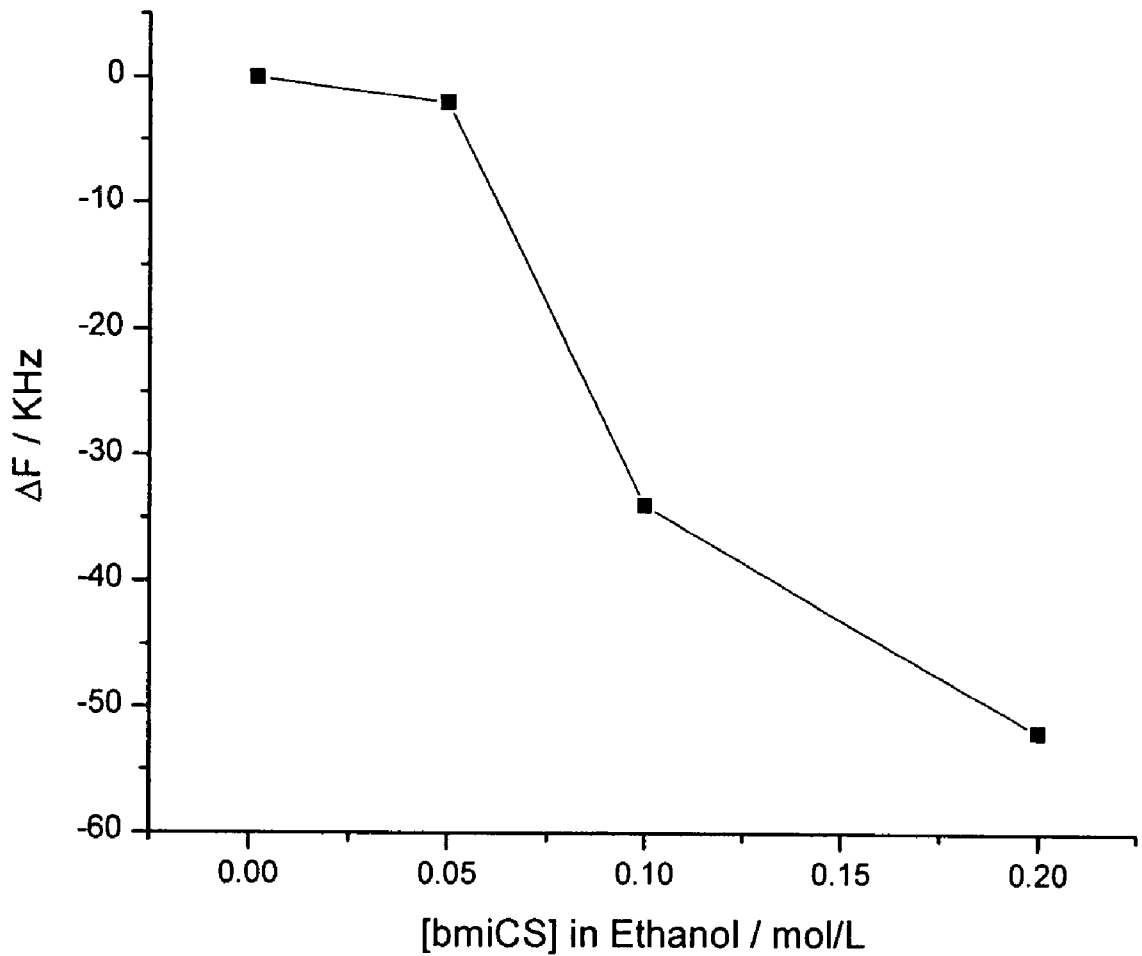
FIG. 26 shows the Δf caused by IL loading as a function of [bmiCS].

The optimum condition for PAN–IL film were used to prepare four identical PAN film (at 1.0 V vs. SCE, 500 seconds) to study IL loading effect on the methane sensitivity. Each of them were soaked overnight in 0.002M, 0.05M, 0.1M and 0.2M bmiCS solutions in ethanol, respectively. FIG. 26 shows the Δf caused by IL loading as a function of [bmiCS]. Shown in FIG. 26, the higher the IL coating concentration, the bigger the frequency shift when methane adsorbed. The resonance frequency of the PAN covered QCM is not significant in the lowest IL coating solution: 0.002 M bmiCS solution but the frequency decrease from 2 KHz (soaked in 0.05 M bmiCS) to 52 KHz (soaked in 0.2 M bmiCS). This indicates the amount of the IL loaded is related to the IL concentration. When the IL solution concentration is 0.5 M or larger, there is too much IL absorbed in the PAN film. Oscillation of the QCM can not be established.

Figure 27A:
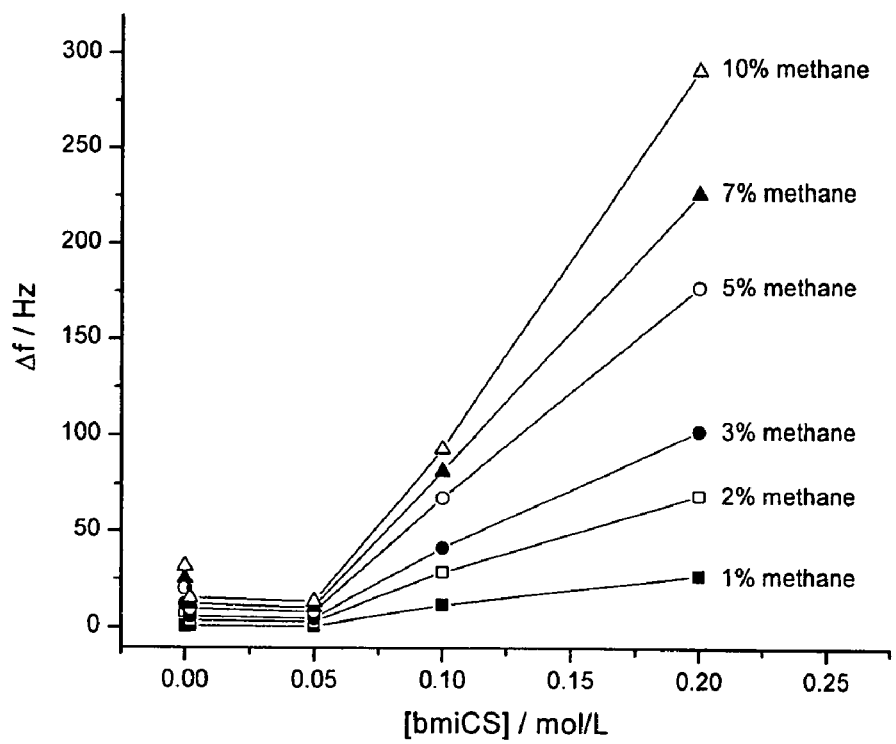
FIG. 27A shows the Δf caused by methane absorption vs. [bmiCS]

FIG. 27A shows the Δf caused by methane absorption vs. [bmiCS], and (b) Δf caused by methane absorption vs. methane concentration of PAN films before and after treated in IL solutions. FIG. 27 showed the quantitative study of the sensitivity of methane vs. bmiCS concentration. In low IL coating solution, i.e. 0.002 M and 0.05 M bmiCS solution, there is no significant change in methane absorption, comparing with that on PAN film itself. However, when higher concentration solutions of bmiCS, e.g. 0.1 M or 0.2 M, were used to coat PAN, the absorption capacity of the PAN/IL film significantly increased. For example, the response is as larger as about 291.5 Hz for 10% methane. In a control experiment, PAN film was modified in pure ethanol overnight; the absorption of methane was similar to the bare PAN film and no enhance sensitivity was observed after the ethanol was dried.

Figure 28A:
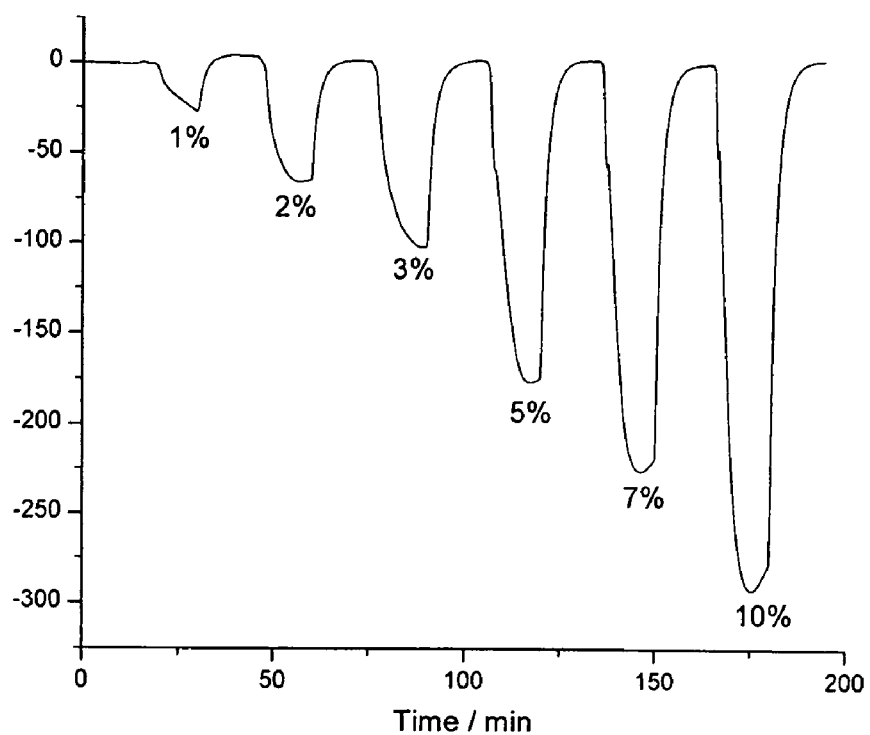
FIGS. 28A and 28B shows the time course response (Δf) curve of PAN/bmiCS (0.2) film response to methane with varied concentration at room temperature.

The PAN–IL film shows not only enhanced sensitivity for methane detection but also excellent reversibility. FIG. 28 shows the time course response (Δf) curve of PAN/bmiCS (0.2) film response to methane with varied concentration at room temperature. FIG. 28 is an representative frequency shift and resistance shift sensorgrams of the PAN/bmiCS film response to methane concentration from 1% to 10%. The adsorption and desorption of methane on PAN/bmiCS film is reversible. Each time the methane gas was switch on or off, the response reaches the equilibrium value in less than 10 min (except at very low concentrations for example 1%). This response time include the time to fill the sensor's chamber, which is about three minutes. In our previous reports with pure IL films the response is faster, about 5 min. The longer response time is because the PAN/IL film is much thicker than the cast IL film in the previous reports. It need more time for the dissolved gas molecules diffuse within the film to reach equilibrium. However, the cost of the response time is worthwhile because the PAN/bmiCS film showed significant improvement for the sensitivity to the methane gas. The lower explosion limit if methane is 5%. At this concentration, the frequency change is about 178 Hz. The response is close to 30 Hz at 1% of methane and 300 Hz at 10% of methane. The base line has about 0.2 Hz noise. Therefore, assuming a detectable signal/noise ratio of ten, we can convincingly detect about a 2 Hz frequency-change, which corresponds to about 0.07% of methane. That means a detection limit of about 400 ppm, or 500 mg/m$^3$. This value is significantly lower than the reported detection limits with QCM/IL sensors. In these reports, the detection limits are larger than thousands ppm for organic vapors with much larger molecular weight than methane. This value is also lower than the occupational exposure limit of methane, which is 1000 ppm.

Figure 27B:
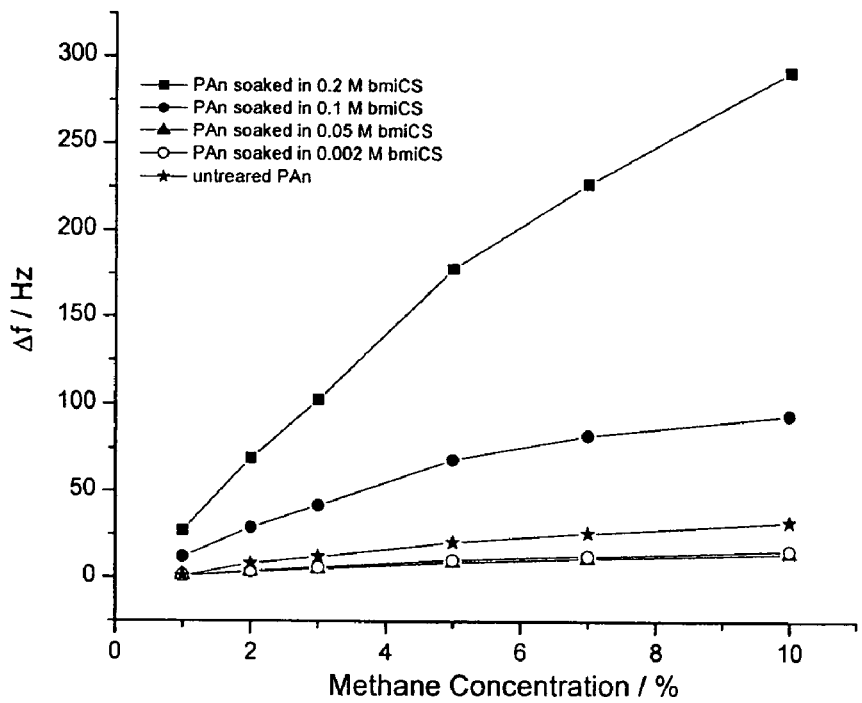
FIG. 27B shows Δf caused by methane absorption vs. methane concentration of PAN films before and after treated in IL solutions.
Figure 28B:
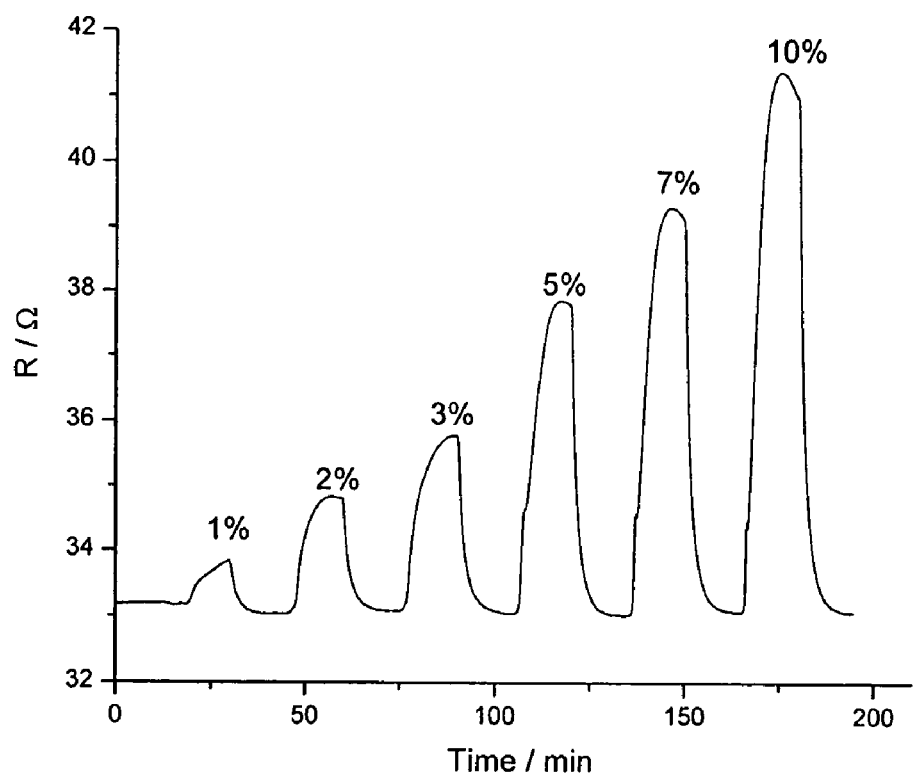
Figure 29A:
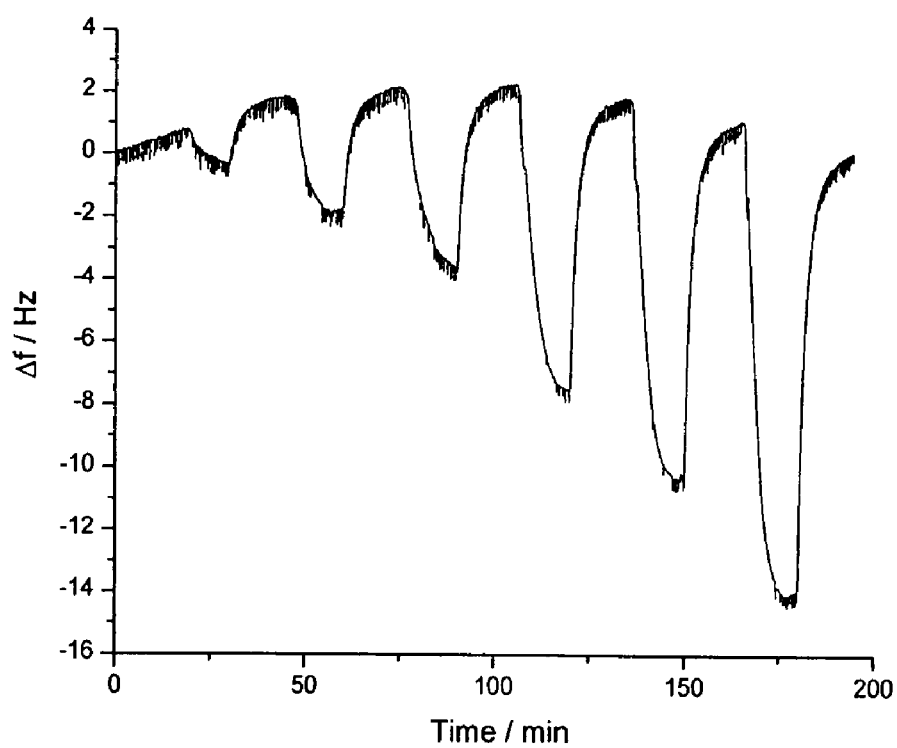
FIGS. 29A and 29B shows the time course response (Δf) curve of PAN/bmiCS (0.002) film response to methane with varied concentration at room temperature.
Figure 29B:
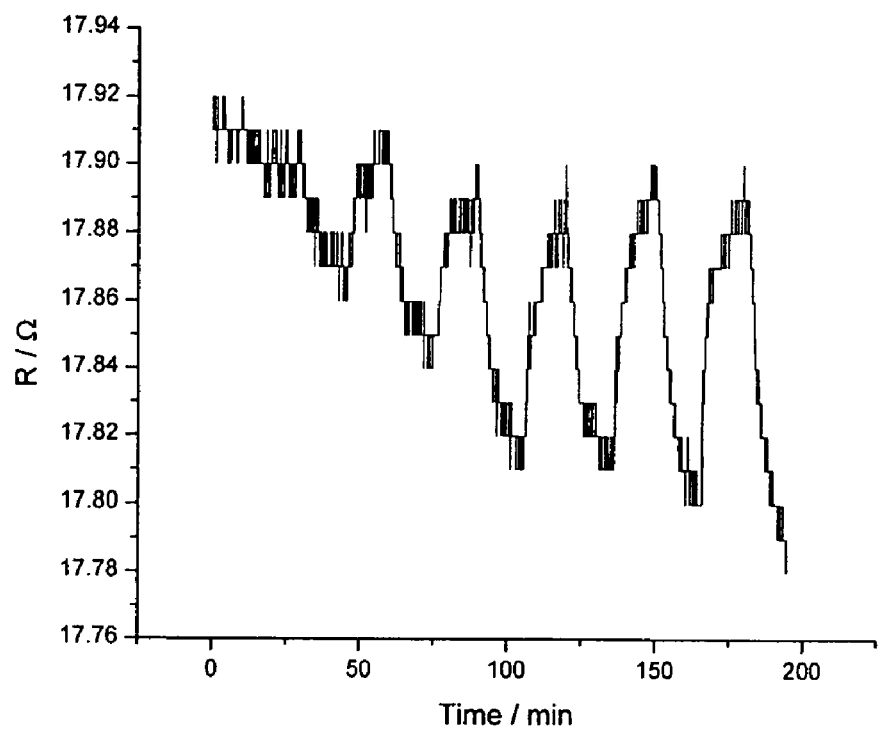

An IL methane gas sensor was successfully developed with an experimental detection limits less than 0.1% and linear range of 0.1% to 20% of methane. 0.1% methane is about 400 ppm which is the best detection limits available with piezoelectric devices. FIG. 27B shows a dynamic linear range of the methane detection to about 5% in which the response is proportional to the methane concentration. At high concentrations, however, the responses deviate from the linear relationship. This may be caused by saturation of the methane with the IL film. The modulus or viscosity change of the PAN/IL film upon absorption of methane could also contribute to the deviations. FIG. 28B shows the damping resistance change vs. methane concentration. When a PAN film is treated in 0.2 M bmiCS solution, the resistance change is as large as 10Ω at 10% of methane. However, when the PAN film is treated in a very dilute bmiCS solution, 0.002 M, the resistance change upon absorption of methane is very small, less than 0.2Ω, see FIG. 29. FIG. 29 also shows the frequency change of the PAN/IL film treated in 0.002 M bmiCS solution. FIG. 29 shows the time course response (Δf) curve of PAN/bmiCS (0.002) film response to methane with varied concentration at room temperature. The sensorgram resembles the features in FIG. 28A, but much smaller in magnitude.

Figure 30A:
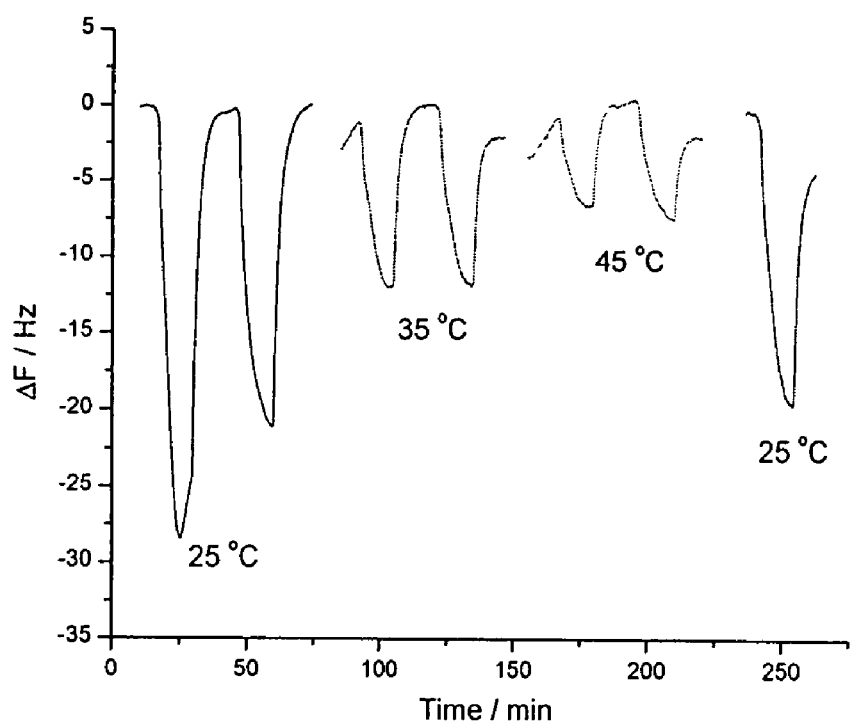
FIG. 30A shows Δf vs. time at various temperatures.
Figure 30B:
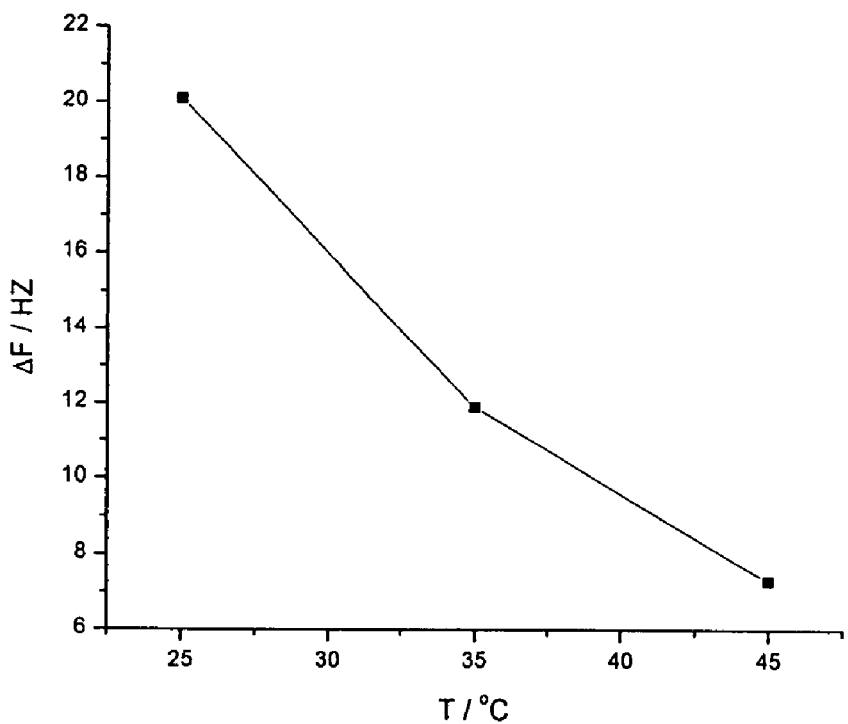
FIG. 30B shows the Δf plotted vs. temperature, at methane concentration of 3%.
Figure 31A:
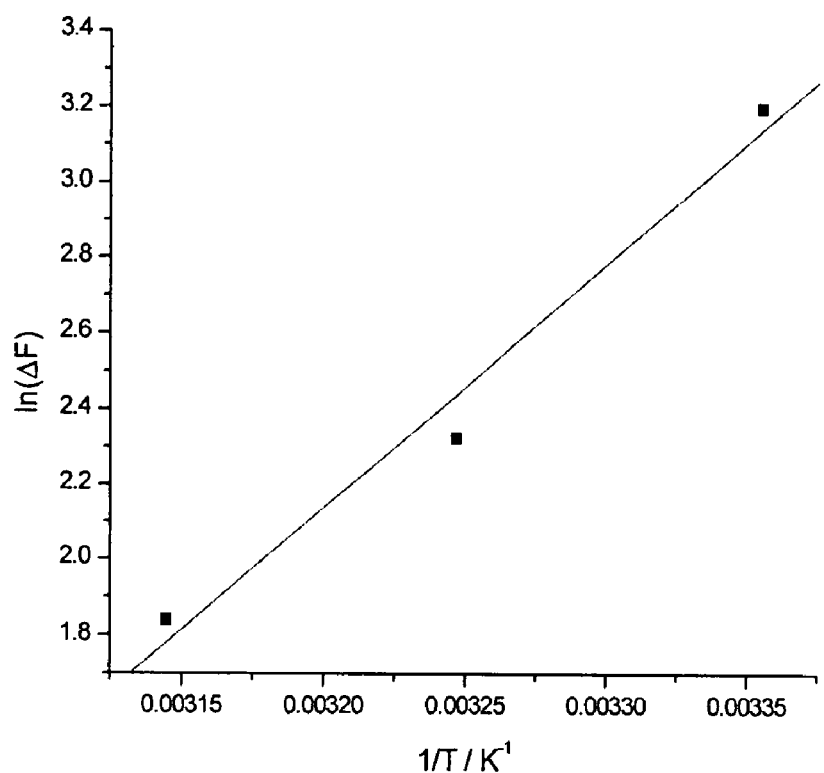
FIG. 31A shows ln(Δf) vs. 1/T.
Figure 31B:
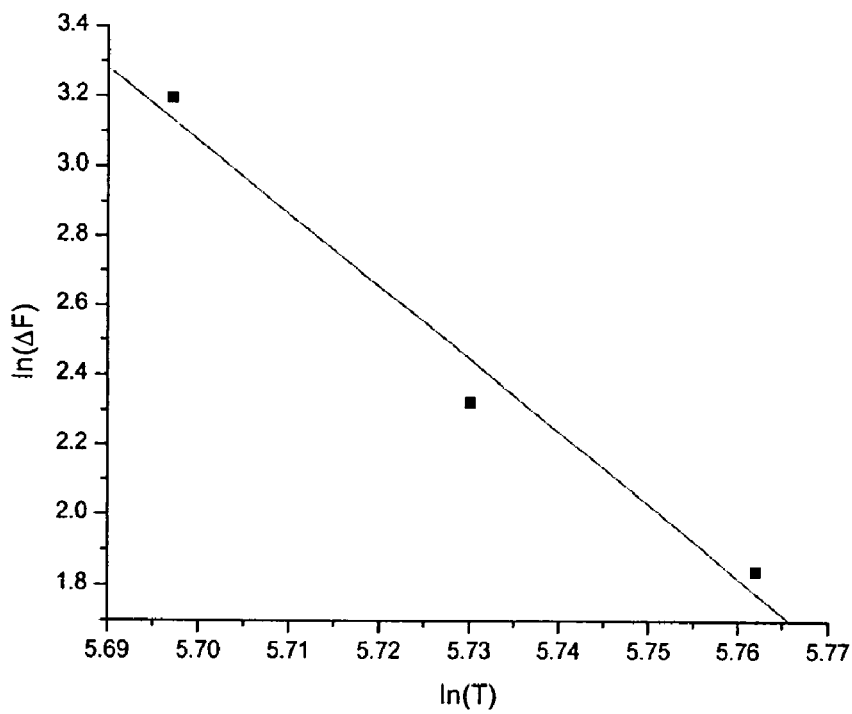
FIG. 31B shows the ln(Δf) vs. ln(T).

Interactions of methane with IL-PAN film at various temperatures: FIG. 30A shows Δf vs. time at various temperatures, and FIG. 30B shows the Δf plotted vs. temperature, at methane concentration of 3%. The results from a doped PAN film soaked in 0.2 M IL solution responses to 3% methane at different temperature are shown in FIG. 30. When the temperature increased from 25° C. to 45° C., the response reduced to about ¼ of the original value. When the temperature was reduced to 25° C. again, we can recover the response. So the PAN/IL film is stable within this temperature range and the temperature effect is reversible. In our previous reports, we have calculated the ΔH and ΔS based on the slopes of ln(Xi) vs 1/T and ln(Xi) vs. ln(T) according to van't Hoff equation. In this work, we cannot calculate the values of the molar fraction, Xi. But the Xi is proportional to the frequency shift, if we still use the Sauerbrey Equation. Therefore, the ln(Δf) vs. 1/T and the ln(xi) vs 1/T should have the same slope but different intercept; the ln(Δf) vs. ln(T) and the ln(xi) vs ln(T) should also have the same slope but different intercept. FIG. 31A shows ln(Δf) vs. 1/T, and FIG. 31B shows the ln(Δf) vs. ln(T). FIG. 31 is used to calculate ΔH and ΔS. FIGS. 31A and B showed the ln(Δf) vs. 1/T and the ln(Δf) vs. ln(T) relationship. We can calculate the ΔH and ΔS according to the slopes. The absorption enthalpy (ΔH) of methane in PAN/bmiCS is −53.5±7.9 KJ/mol. The absorption entropy is 173.7±27.4 J/K.mol. These values are much larger than those reported by groups in the literature.

Selectivity results: Various pairs of conductive polymer/polyelectrolyte and IL composites can be imagined. The value and importance of the wide range electrodes modified by immobilization of a single species (conductive polymer or polyelectrolyte) is widely acknowledged and we believe that using appropriately chosen pairs of immobilized species can produce unique surfaces with valuable chemical properties (e.g. controlled porosity, orientation and tunable thickness).

In some embodiments, a polymer (including, but not limited to a conductive polymer, such as polyaniline) can be formed from monomer structures having functional side groups. Thus, conductive polymer templates having additional functional groups can be generated for binding the IL to a surface. The functional groups can be used to immobilize ionic liquids with preferred orientation via various molecular interactions (ie. hydrogen bond, p-p, dipolar, ionic. etc.) of ionic liquids and conductive polymer functional groups.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

I claim:
1. A device which comprises:
   (a) a substrate with an exposed surface; and
   (b) an ionic liquid film which is bound to the exposed surface so as to enable the ionic liquid to absorb an organic chemical which would be absorbed by an unbound film of the ionic liquid,
   wherein:
   (i) the ionic liquid film is bound to the surface by a force between the ionic liquid film and one or more polyelectrolytes or conductive polymers on the surface, the force comprising one or more of an electrostatic force, a hydrogen bonding force, a van der Waals force, and an ionic force; and
   (ii) the ionic liquid film comprises an ionic liquid selected from the group consisting of ionic liquid ammonium salts, ionic liquid phosphonium salts, ionic liquid imidazolium salts, ionic liquid pyrrolidinium salts, and ionic liquid pyridinium salts.
2. The device of claim 1, wherein the one or more polyelectrolytes or conductive polymers comprises polyaniline.
3. The device of claim 1, wherein the organic chemical is methane.
4. The device of claim 1, wherein the ionic liquid film is bound to the surface by a force between the ionic liquid film and a conductive polymer.
5. The device of claim 4, wherein the ionic liquid is an ionic liquid imidazolium salt.
6. The device of claim 5, wherein the conductive polymer comprises polyaniline.
7. The device of claim 1, wherein the one or more polyelectrolytes or conductive polymers comprises poly(vinylferrocene) (PVF).
8. The device of claim 1, wherein the one or more polyelectrolytes or conductive polymers comprises poly(styrene sulfonate) (PSS).
9. A method of absorbing an organic sample comprising:
   (a) providing a device which comprises a substrate with an exposed surface; and an ionic liquid film which is bound to the exposed surface so as to enable the ionic liquid to absorb an organic chemical which would be absorbed by an unbound film of the ionic liquid, wherein:
   (i) the ionic liquid film is bound to the surface by a force between the ionic liquid film and one or more polyelectrolytes or conductive polymers on the surface, the force comprising one or more of an electrostatic force, a hydrogen bonding force, a van der Waals force, and an ionic force; and
   (ii) the ionic liquid film comprises an ionic liquid selected from the group consisting of ionic liquid ammonium salts, ionic liquid phosphonium salts, ionic liquid imidazolium salts, ionic liquid pyrrolidinium salts, and ionic liquid pyridinium salts; and
   (b) providing the organic chemical on the exposed surface of the ionic liquid film so that the film absorbs the organic chemical.
10. The method of claim 9, wherein the organic chemical is methane.
11. A gas sensor for determining the concentration of an organic vapor in a gaseous sample comprising:
   (a) a quartz crystal microbalance having a transducer surface; and
   (b) an ionic liquid film bound to the transducer surface of the quartz crystal microbalance, wherein:
   (i) the ionic liquid film is bound to the transducer surface by a force between the ionic liquid film and one or more polyelectrolytes or conductive polymers on the trans- ducer surface, the force comprising one or more of an electrostatic force, a hydrogen bonding force, a van der Waals force, and an ionic force;
(ii) when the organic vapor is present in the gaseous sample it is absorbed in the ionic liquid film on the transducer surface and changes a resonant frequency of the quartz crystal microbalance; and
(iii) the ionic liquid film comprises an ionic liquid selected from the group consisting of ionic liquid ammonium salts, ionic liquid phosphonium salts, ionic liquid imidazolium salts, ionic liquid pyrrolidinium salts, and ionic liquid pyridinium salts.

12. The gas sensor of claim 11, wherein the one or more polyelectrolytes or conductive polymers comprises polyaniline.

13. The gas sensor of claim 12, wherein the polyaniline comprises doped polyaniline.

14. The gas sensor of claim 11, wherein the organic vapor is methane.

15. The gas sensor of claim 11, wherein the one or more polyelectrolytes or conductive polymers comprises one or more of poly(styrene sulfonate) (PSS) and poly(vinylferrocene) (PVF).

16. The gas sensor of claim 11, wherein the ionic liquid film is bound to the surface by a force between the ionic liquid film and a conductive polymer.

17. The gas sensor of claim 16, wherein the ionic liquid is an ionic liquid imidazolium salt.

18. The gas sensor of claim 17, wherein the conductive polymer comprises polyaniline.

19. The gas sensor of claim 11, wherein the one or more polyelectrolytes or conductive polymers comprises poly(vinylferrocene) (PVF).

20. The gas sensor of claim 11, wherein the one or more polyelectrolytes or conductive polymers comprises poly(styrene sulfonate) (PSS).

21. A method of determining the concentration of an organic vapor in a gaseous sample, the method comprising:
(a) providing a gas sensor for detecting the concentration of an organic vapor in a gaseous sample comprising a quartz crystal microbalance having a transducer surface; and an ionic liquid film bound on the transducer surface of the quartz crystal microbalance, wherein:
(i) the ionic liquid film is bound to the transducer surface by a force between the ionic liquid film and one or more polyelectrolytes or conductive polymers on the surface, the force comprising one or more of an electrostatic force, a hydrogen bonding force, a van der Waals force, and an ionic force;
(ii) when the organic vapor is present in the gaseous sample it is absorbed in the ionic liquid film on the transducer surface and changes a resonant frequency of the quartz crystal microbalance; and
(iii) the ionic liquid film comprises an ionic liquid selected from the group consisting of ionic liquid ammonium salts, ionic liquid phosphonium salts, ionic liquid imidazolium salts, ionic liquid pvrrolidinium salts, and ionic liquid pvridinium salts;
(b) providing a reference gas to the transducer surface of the gas sensor;
(c) measuring a first reference frequency of the gas sensor;
(d) providing the gaseous sample to the transducer surface of the gas sensor;
(e) measuring a second resonant frequency of the gas sensor;
(f) subtracting the first resonant frequency from the second resonant frequency to provide a frequency change; and
(g) determining the concentration of the organic vapor in the gaseous sample by the frequency change.

22. A method of determining the concentration of an organic vapor in a gaseous sample, the method comprising:
(a) providing a first gas sensor and a second gas sensor, the first and second gas sensors for detecting the concentration of an organic vapor in a gaseous sample, the sensors comprising a quartz crystal microbalance having a transducer surface, and an ionic liquid film bound on the transducer surface of the quartz crystal microbalance, wherein:
(i) the ionic liquid film is bound to the transducer surface by a force between the ionic liquid film and one or more polyelectrolytes or conductive polymers on the surface, the force comprising one or more of an electrostatic force, a hydrogen bonding force, a van der Waals force, and an ionic force;
(ii) when the organic vapor is present in the gaseous sample it is absorbed in the ionic liquid film on the transducer surface and changes a resonant frequency of the quartz crystal microbalance; and
(iii) the ionic liquid film comprises an ionic liquid selected from the group consisting of ionic liquid ammonium salts, ionic liquid phosphonium salts, ionic liquid imidazolium salts, ionic liquid pyrrolidinium salts, and ionic liquid pyridinium salts;
(b) providing a reference gas to the first gas sensor;
(c) providing the gaseous sample to the second gas sensor;
(d) measuring a resonant frequency of the first sensor;
(e) measuring a resonant frequency of the second sensor;
(f) subtracting the resonant frequency of the first sensor from the resonant frequency of the second sensor to provide a frequency difference; and
(g) determining the concentration of the organic vapor in the gaseous sample by the frequency difference.

23. A method of detecting an unknown organic vapor in a gaseous sample, the method comprising:
(a) providing an array of gas sensors for detecting an organic vapor in a gaseous sample, each of the sensors comprising a quartz crystal microbalance having a transducer surface, and an ionic liquid film bound on the transducer surface of the quartz crystal microbalance, wherein:
(i) the ionic liquid film is bound to the transducer surface by a force between the ionic liquid film and one or more polyelectrolytes or conductive polymers on the surface, the force comprising one or more of an electrostatic force, a hydrogen bonding force, a van der Waals force, and an ionic force;
(ii) when the organic vapor is present in the gaseous sample it is absorbed in the ionic liquid film on the transducer surface and changes a resonant frequency of the quartz crystal microbalance; and
(iii) the ionic liquid film comprises an ionic liquid selected from the group consisting of ionic liquid ammonium salts, ionic liquid phosphonium salts, ionic liquid imidazolium salts, ionic liquid pyrrolidinium salts, and ionic liquid pyridinium salts;
(b) providing a reference gas to the array;
(c) measuring a reference frequency of each of the sensors in the array;
(d) providing the gaseous sample to the array;
(e) measuring a resonant frequency of each of the sensors of the array;

(f) subtracting the resonant frequency of each of the sensors from the resonant frequency of each of the sensors to provide a frequency difference for each of the sensors of the array; and (g) detecting the organic vapor in the gaseous sample by the frequency difference for each of the sensors in the array.

* * * * *

UNITED STATES PATENT AND TRADEMARK OFFICE
CERTIFICATE OF CORRECTION

PATENT NO. : 7,886,577 B2  Page 1 of 1
APPLICATION NO. : 11/725637
DATED : February 15, 2011
INVENTOR(S) : Xiangqun Zeng It is certified that error appears in the above-identified patent and that said Letters Patent is hereby corrected as shown below:

Column 17, line 63 "($\Delta f/f=10^8$)" should be -- ($\Delta f/f=10^{-8}$) --.

Column 24, lines 62 & 63 "vibration of $-SO_3$" should be -- vibration of $-SO3$ --.

Column 24, line 50 "ATR-FRIT" should be -- ATR-FTIR --.

Column 25, line 7 "on ZeSe" should be -- on ZnSe --.

Column 29, lines 57 & 58 (Claim 21 (iii)), "liquid pvrrolidinium" should be -- liquid pyrrolidinium --.

Column 29, line 58 (Claim 21 (iii)), "liquid pvridinium salts" should be -- liquid pyridinium salts --.

Signed and Sealed this
Twelfth Day of June, 2012

David J. Kappos
*Director of the United States Patent and Trademark Office*